(12) United States Patent
Keegan et al.

(10) Patent No.: US 7,144,408 B2
(45) Date of Patent: Dec. 5, 2006

(54) EMBOLIC PROTECTION SYSTEM

(75) Inventors: Martin Keegan, Knocknacarra (IE); Eamon Brady, Elphin (IE); Brendan Casey, Barna (IE); David Vale, Clontarf (IE); John Neilan, Gort (IE); Morgan Tierney, Ferbane (IE)

(73) Assignee: Salviac Limited (IE)

( * ) Notice: Subject to any disclaimer, the term of this patent is extended or adjusted under 35 U.S.C. 154(b) by 21 days.

(21) Appl. No.: 10/379,434

(22) Filed: Mar. 5, 2003

(65) Prior Publication Data

US 2003/0212429 A1    Nov. 13, 2003

Related U.S. Application Data

(60) Provisional application No. 60/361,340, filed on Mar. 5, 2002.

(51) Int. Cl.
*A61M 29/00* (2006.01)
(52) U.S. Cl. ............................................. 606/200
(58) Field of Classification Search ............... 606/200
See application file for complete search history.

(56) References Cited

U.S. PATENT DOCUMENTS

| | | | |
|---|---|---|---|
| 2,854,983 A | 10/1958 | Barskin |
| 3,334,629 A | 8/1967 | Cohn |
| 3,435,824 A | 4/1969 | Gamponia |
| 3,540,431 A | 11/1970 | Mebin-Uddin |
| 3,692,029 A | 9/1972 | Adair |
| 3,730,185 A | 5/1973 | Cook et al. |
| 3,952,747 A | 4/1976 | Kimmell, Jr. |
| 4,295,464 A | 10/1981 | Shihata |
| 4,404,971 A | 9/1983 | LeVeen et al. |
| 4,423,725 A | 1/1984 | Baran et al. |
| 4,425,908 A | 1/1984 | Simon |
| 4,445,892 A | 5/1984 | Hussein et al. |
| 4,493,711 A | 1/1985 | Chin et al. |
| 4,512,762 A | 4/1985 | Spears |
| 4,585,000 A | 4/1986 | Hershenson |
| 4,586,919 A | 5/1986 | Taheri |
| 4,610,662 A | 9/1986 | Weikl et al. |
| 4,611,594 A | 9/1986 | Grayhack et al. |
| 4,619,246 A | 10/1986 | Molgaard-Nielsen et al. |
| 4,643,187 A | 2/1987 | Okada |
| 4,650,466 A | 3/1987 | Luther |
| 4,712,551 A | 12/1987 | Rayhanabad |
| 4,723,549 A | 2/1988 | Wholey et al. |
| 4,781,177 A | 11/1988 | Lebigot |
| 4,790,812 A | 12/1988 | Hawkins, Jr. et al. |
| 4,794,928 A | 1/1989 | Kletschka |
| 4,807,626 A | 2/1989 | McGirr |

(Continued)

FOREIGN PATENT DOCUMENTS

DE    3706077    6/1988

(Continued)

OTHER PUBLICATIONS

US 6,348,062, 02/2002, Hopkins et al. (withdrawn)

*Primary Examiner*—(Jackie) Tan-Uyen T. Ho
(74) *Attorney, Agent, or Firm*—Kudirka & Jobse LLP

(57) ABSTRACT

An embolic protection filter system comprises a collapsible embolic protection filter 62 having a collapsed configuration for delivery of the filter, and a deployed configuration and a temporary lumen defining member 60. The lumen defining member 60 is used for loading a filter-containing delivery catheter 63 onto a guidewire 65. After loading, the member 60 can be removed by pulling on a tab 61.

3 Claims, 68 Drawing Sheets

U.S. PATENT DOCUMENTS

| | | | |
|---|---|---|---|
| 4,817,600 A | 4/1989 | Herms et al. | |
| 4,832,055 A | 5/1989 | Palestrant | |
| 4,867,156 A | 9/1989 | Stack et al. | |
| 4,873,978 A | 10/1989 | Ginsburg | |
| 4,926,858 A | 5/1990 | Gifford, III et al. | |
| 4,927,426 A | 5/1990 | Dretler | |
| 4,957,501 A | 9/1990 | Lahille et al. | |
| 4,969,891 A | 11/1990 | Gewertz | |
| 4,990,156 A | 2/1991 | Lefebvre | |
| 5,011,488 A | 4/1991 | Ginsburg | |
| 5,026,377 A | 6/1991 | Burton et al. | |
| 5,053,008 A | 10/1991 | Bajaj | |
| 5,092,839 A | 3/1992 | Kipperman | |
| 5,100,423 A | 3/1992 | Fearnot | |
| 5,108,419 A | 4/1992 | Reger et al. | |
| 5,122,125 A | 6/1992 | Deuss | |
| 5,133,733 A | 7/1992 | Rasmussen et al. | |
| 5,171,233 A | 12/1992 | Amplatz et al. | |
| 5,178,158 A | 1/1993 | de Toledo | |
| 5,192,284 A | 3/1993 | Pleatman | |
| 5,324,304 A | 6/1994 | Rasmussen | |
| 5,329,942 A | 7/1994 | Gunther et al. | |
| 5,336,234 A | 8/1994 | Vigil et al. | |
| 5,354,310 A | 10/1994 | Garnic et al. | |
| 5,370,657 A | 12/1994 | Irie | |
| 5,375,612 A | 12/1994 | Cottenceau et al. | |
| 5,383,887 A | 1/1995 | Nadal | |
| 5,387,219 A | 2/1995 | Rappe | |
| 5,405,329 A | 4/1995 | Durand | |
| 5,421,832 A | 6/1995 | Lefebvre | |
| 5,454,788 A | 10/1995 | Walker et al. | |
| 5,540,707 A | 7/1996 | Ressemann et al. | |
| 5,549,626 A | 8/1996 | Miller et al. | |
| 5,593,394 A | 1/1997 | Kanesaka et al. | |
| 5,658,296 A | 8/1997 | Bates et al. | |
| 5,662,671 A | 9/1997 | Barbut et al. | |
| 5,669,933 A | 9/1997 | Simon et al. | |
| 5,683,451 A | 11/1997 | Lenker et al. | |
| 5,695,519 A | 12/1997 | Summers et al. | |
| 5,709,704 A | 1/1998 | Nott et al. | |
| 5,720,764 A | 2/1998 | Naderlinger | |
| 5,725,519 A | 3/1998 | Penner et al. | |
| 5,766,203 A | 6/1998 | Imran et al. | |
| 5,769,816 A | 6/1998 | Barbut et al. | |
| 5,769,871 A | 6/1998 | Mers Kelly et al. | |
| 5,779,716 A | 7/1998 | Cano et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,823,992 A | 10/1998 | Salmon et al. | |
| 5,827,324 A | 10/1998 | Cassell et al. | |
| 5,834,449 A | 11/1998 | Thompson et al. | |
| 5,836,969 A | 11/1998 | Kim et al. | |
| 5,843,167 A | 12/1998 | Dwyer et al. | |
| 5,846,260 A | 12/1998 | Maahs | |
| 5,848,964 A | 12/1998 | Samuels | |
| 5,876,367 A | 3/1999 | Kaganov et al. | |
| 5,882,329 A | 3/1999 | Patterson et al. | |
| 5,895,398 A | 4/1999 | Wensel et al. | |
| 5,895,410 A | 4/1999 | Forber et al. | |
| 5,897,567 A | 4/1999 | Ressemann et al. | |
| 5,902,334 A | 5/1999 | Dwyer et al. | |
| 5,910,154 A | 6/1999 | Tsugita et al. | |
| 5,911,725 A | 6/1999 | Boury | |
| 5,911,734 A | 6/1999 | Tsugita et al. | |
| 5,928,261 A | 7/1999 | Ruiz | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,968,071 A | 10/1999 | Chevillon | |
| 5,976,172 A | 11/1999 | Homsma et al. | |
| 5,984,947 A | 11/1999 | Smith | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,093 A | 1/2000 | Nott et al. | |
| 6,027,509 A | 2/2000 | Schatz et al. | |
| 6,027,520 A | 2/2000 | Tsugita et al. | |
| 6,042,598 A | 3/2000 | Tsugita et al. | |
| 6,048,645 A | 4/2000 | Saidi et al. | |
| 6,051,014 A | 4/2000 | Jang | |
| 6,053,832 A | 4/2000 | Saito | |
| 6,053,932 A | 4/2000 | Daniel et al. | |
| 6,059,814 A | 5/2000 | Ladd | |
| 6,063,173 A | 5/2000 | Torii et al. | |
| 6,066,149 A | 5/2000 | Samson et al. | |
| 6,074,357 A | 6/2000 | Kaganov et al. | |
| 6,083,239 A | 7/2000 | Addis | |
| 6,086,577 A | 7/2000 | Ken et al. | |
| 6,086,605 A | 7/2000 | Barbut et al. | |
| 6,090,097 A | 7/2000 | Barbut et al. | |
| 6,096,053 A | 8/2000 | Bates | |
| 6,099,534 A | 8/2000 | Bates et al. | |
| 6,099,549 A | 8/2000 | Bosma et al. | |
| 6,123,715 A | 9/2000 | Amplatz | |
| 6,129,739 A | 10/2000 | Khosravi | |
| 6,132,458 A | 10/2000 | Staehle et al. | |
| 6,142,987 A | 11/2000 | Tsugita | |
| 6,146,404 A | 11/2000 | Kim et al. | |
| 6,152,946 A | 11/2000 | Broome et al. | |
| 6,165,200 A | 12/2000 | Tsugita et al. | |
| 6,168,579 B1 | 1/2001 | Tsugita | |
| 6,168,604 B1 | 1/2001 | Cano | |
| 6,171,327 B1 | 1/2001 | Daniel et al. | |
| 6,171,328 B1 | 1/2001 | Addis | |
| 6,176,849 B1 | 1/2001 | Yang et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,238,412 B1 | 5/2001 | Dubrul et al. | |
| 6,241,746 B1 | 6/2001 | Bosma et al. | |
| 6,245,012 B1 | 6/2001 | Kleshinski | |
| 6,245,087 B1 | 6/2001 | Addis | |
| 6,245,088 B1 | 6/2001 | Lowery | |
| 6,245,089 B1 | 6/2001 | Daniel et al. | |
| 6,251,122 B1 | 6/2001 | Tsukernik | |
| 6,254,563 B1 | 7/2001 | Macoviak et al. | |
| 6,258,115 B1 | 7/2001 | Dubrul | |
| 6,258,120 B1 | 7/2001 | McKenzie et al. | |
| 6,264,663 B1 | 7/2001 | Cano | |
| 6,264,672 B1 | 7/2001 | Fisher | |
| 6,267,776 B1 | 7/2001 | O'Connell | |
| 6,267,777 B1 | 7/2001 | Bosma et al. | |
| 6,270,513 B1 | 8/2001 | Tsugita et al. | |
| 6,273,901 B1 | 8/2001 | Whitcher et al. | |
| 6,277,138 B1 | 8/2001 | Levinson et al. | |
| 6,277,139 B1 | 8/2001 | Levinson et al. | |
| 6,290,710 B1 | 9/2001 | Cryer et al. | |
| 6,295,989 B1 | 10/2001 | Connors, III | |
| 6,306,163 B1 | 10/2001 | Fitz | |
| 6,319,242 B1 | 11/2001 | Patterson et al. | |
| 6,325,815 B1 | 12/2001 | Kusleika et al. | |
| 6,336,934 B1 | 1/2002 | Gilson et al. | |
| 6,340,364 B1 | 1/2002 | Kanesaka | |
| 6,346,116 B1 | 2/2002 | Brooks et al. | |

| | | | | | | |
|---|---|---|---|---|---|---|
| 6,348,056 B1 | 2/2002 | Bates et al. | | 6,589,265 B1 | 7/2003 | Palmer et al. |
| 6,355,051 B1 | 3/2002 | Sisskind et al. | | 6,592,546 B1 | 7/2003 | Barbut et al. |
| 6,361,545 B1 | 3/2002 | Macoviak et al. | | 6,592,606 B1 | 7/2003 | Huter et al. |
| 6,361,546 B1 | 3/2002 | Khosravi | | 6,592,616 B1 | 7/2003 | Stack et al. |
| 6,364,895 B1 | 4/2002 | Greenhalgh | | 6,596,011 B1 | 7/2003 | Johnson et al. |
| 6,371,935 B1 | 4/2002 | Macoiviak et al. | | 6,599,307 B1 | 7/2003 | Huter et al. |
| 6,371,969 B1 | 4/2002 | Tsugita et al. | | 6,602,269 B1 | 8/2003 | Wallace et al. |
| 6,371,970 B1 | 4/2002 | Khosravi et al. | | 6,602,271 B1 | 8/2003 | Adams et al. |
| 6,371,971 B1 | 4/2002 | Tsugita et al. | | 6,602,272 B1 | 8/2003 | Boylan et al. |
| 6,375,670 B1 | 4/2002 | Greenhalgh | | 6,605,102 B1 | 8/2003 | Mazzocchi et al. |
| 6,383,206 B1 | 5/2002 | Gillick et al. | | 6,605,111 B1 | 8/2003 | Bose et al. |
| 6,391,044 B1 | 5/2002 | Yadav et al. | | 6,610,077 B1 | 8/2003 | Hancock et al. |
| 6,394,978 B1 | 5/2002 | Boyle et al. | | 6,616,679 B1 | 9/2003 | Khosravi et al. |
| 6,395,014 B1 | 5/2002 | Macoviak et al. | | 6,616,680 B1 | 9/2003 | Thielen |
| 6,395,017 B1 | 5/2002 | Dwyer et al. | | 6,616,681 B1 | 9/2003 | Hanson et al. |
| 6,398,756 B1 | 6/2002 | Peterson et al. | | 6,616,682 B1 | 9/2003 | Joergensen et al. |
| 6,402,771 B1 | 6/2002 | Palmer et al. | | 6,620,148 B1 | 9/2003 | Tsugita |
| 6,406,471 B1 | 6/2002 | Jang et al. | | 6,620,182 B1 | 9/2003 | Khosravi et al. |
| 6,423,032 B1 | 7/2002 | Parodi | | 6,623,450 B1 | 9/2003 | Dutta |
| 6,425,909 B1 | 7/2002 | Dieck et al. | | 6,632,236 B1 | 10/2003 | Hogendijk |
| 6,428,559 B1 | 8/2002 | Johnson | | 6,632,241 B1 | 10/2003 | Hancock et al. |
| 6,432,122 B1 | 8/2002 | Gilson et al. | | 6,635,070 B1 | 10/2003 | Leeflang et al. |
| 6,436,121 B1 | 8/2002 | Blom | | 6,638,294 B1 | 10/2003 | Palmer |
| 6,443,926 B1 | 9/2002 | Kletschka | | 6,645,220 B1 | 11/2003 | Huter et al. |
| 6,443,971 B1 | 9/2002 | Boylan et al. | | 6,645,223 B1 | 11/2003 | Boyle et al. |
| 6,443,979 B1 | 9/2002 | Stalker et al. | | 6,645,224 B1 | 11/2003 | Gilson et al. |
| 6,447,530 B1 | 9/2002 | Ostrovsky et al. | | 6,652,480 B1 | 11/2003 | Imran et al. |
| 6,458,139 B1 | 10/2002 | Palmer et al. | | 6,652,505 B1 | 11/2003 | Tsugita |
| 6,461,370 B1 | 10/2002 | Gray et al. | | 6,652,554 B1 | 11/2003 | Wholey et al. |
| 6,468,291 B1 | 10/2002 | Bates et al. | | 6,652,557 B1 | 11/2003 | MacDonald |
| 6,482,222 B1 | 11/2002 | Bruckheimer et al. | | 6,656,202 B1 | 12/2003 | Papp et al. |
| 6,485,497 B1 | 11/2002 | Wensel et al. | | 6,660,021 B1 | 12/2003 | Palmer et al. |
| 6,485,500 B1 | 11/2002 | Kokish et al. | | 6,663,650 B1 | 12/2003 | Sepetka et al. |
| 6,485,501 B1 | 11/2002 | Green | | 6,663,652 B1 | 12/2003 | Daniel et al. |
| 6,485,502 B1 | 11/2002 | Don Michael et al. | | 2001/0000799 A1 | 5/2001 | Wessman et al. |
| 6,494,895 B1 | 12/2002 | Addis | | 2001/0001315 A1 | 5/2001 | Bates et al. |
| 6,506,203 B1 | 1/2003 | Boyle et al. | | 2001/0007947 A1 | 7/2001 | Kanesaka |
| 6,506,205 B1 | 1/2003 | Goldberg et al. | | 2001/0012951 A1 | 8/2001 | Bates et al. |
| 6,511,492 B1 | 1/2003 | Rosenbluth et al. | | 2001/0020175 A1 | 9/2001 | Yassour et al. |
| 6,511,496 B1 | 1/2003 | Huter et al. | | 2001/0025187 A1 | 9/2001 | Okada |
| 6,511,497 B1 | 1/2003 | Braun et al. | | 2001/0031982 A1 | 10/2001 | Peterson et al. |
| 6,511,503 B1 | 1/2003 | Burkett et al. | | 2001/0039431 A1 | 11/2001 | De Vries et al. |
| 6,514,273 B1 | 2/2003 | Voss et al. | | 2001/0041908 A1 | 11/2001 | Levinson et al. |
| 6,517,550 B1 | 2/2003 | Konya et al. | | 2001/0044632 A1 | 11/2001 | Daniel et al. |
| 6,517,559 B1 | 2/2003 | O'Connell | | 2002/0002384 A1 | 1/2002 | Gilson et al. |
| 6,520,978 B1 | 2/2003 | Blackledge et al. | | 2002/064667 A1 | 1/2002 | Adams et al. |
| 6,527,746 B1 | 3/2003 | Oslund et al. | | 2002/0022858 A1 | 2/2002 | Demond et al. |
| 6,530,939 B1 | 3/2003 | Hopkins et al. | | 2002/0022860 A1 | 2/2002 | Borillo et al. |
| 6,530,940 B1 | 3/2003 | Fisher | | 2002/0026211 A1 | 2/2002 | Khosravi et al. |
| 6,533,800 B1 | 3/2003 | Barbut | | 2002/0026213 A1 | 2/2002 | Gilson et al. |
| 6,537,294 B1 * | 3/2003 | Boyle et al. ............... 606/200 | | 2002/0032460 A1 | 3/2002 | Kusleika et al. |
| 6,537,295 B1 | 3/2003 | Petersen | | 2002/0045916 A1 | 4/2002 | Gray et al. |
| 6,537,296 B1 | 3/2003 | Levinson et al. | | 2002/0045918 A1 | 4/2002 | Suon et al. |
| 6,537,297 B1 | 3/2003 | Tsugita et al. | | 2002/0049467 A1 | 4/2002 | Gilson et al. |
| 6,540,722 B1 | 4/2003 | Boyle et al. | | 2002/0049468 A1 | 4/2002 | Streeker et al. |
| 6,540,767 B1 | 4/2003 | Walak et al. | | 2002/0052626 A1 | 5/2002 | Gilson et al. |
| 6,540,768 B1 | 4/2003 | Diaz et al. | | 2002/0052638 A1 | 5/2002 | Zadno-Azizi |
| 6,544,279 B1 | 4/2003 | Hopkins et al. | | 2002/0055747 A1 | 5/2002 | Cano et al. |
| 6,544,280 B1 | 4/2003 | Daniel et al. | | 2002/0055767 A1 | 5/2002 | Forde et al. |
| 6,547,760 B1 | 4/2003 | Samson et al. | | 2002/0058911 A1 | 5/2002 | Gilson et al. |
| 6,551,341 B1 | 4/2003 | Boylan et al. | | 2002/0058963 A1 | 5/2002 | Vale et al. |
| 6,551,342 B1 | 4/2003 | Shen et al. | | 2002/0062133 A1 | 5/2002 | Gilson et al. |
| 6,558,405 B1 | 5/2003 | McInnes | | 2002/0062135 A1 | 5/2002 | Mazzocchi et al. |
| 6,562,058 B1 | 5/2003 | Seguin et al. | | 2002/0065507 A1 | 5/2002 | Zadno-Azizi |
| 6,565,591 B1 | 5/2003 | Brady et al. | | 2002/0068954 A1 | 6/2002 | Foster |
| 6,569,184 B1 | 5/2003 | Huter | | 2002/0068955 A1 | 6/2002 | Khosravi |
| 6,575,995 B1 | 6/2003 | Huter et al. | | 2002/0072730 A1 | 6/2002 | McGill et al. |
| 6,575,996 B1 | 6/2003 | Denison et al. | | 2002/0072765 A1 | 6/2002 | Mazzocchi et al. |
| 6,575,997 B1 | 6/2003 | Palmer et al. | | 2002/0082525 A1 | 6/2002 | Oslund et al. |
| 6,582,447 B1 | 6/2003 | Patel et al. | | 2002/0082639 A1 | 6/2002 | Broome et al. |
| 6,582,448 B1 | 6/2003 | Boyle et al. | | 2002/0091408 A1 | 7/2002 | Sutton et al. |
| 6,585,756 B1 | 7/2003 | Strecker | | 2002/0091409 A1 | 7/2002 | Sutton et al. |
| 6,589,263 B1 | 7/2003 | Hopkins et al. | | 2002/0095141 A1 | 7/2002 | Belef et al. |

| | | | | | | |
|---|---|---|---|---|---|---|
| 2002/0095170 A1 | 7/2002 | Krolik et al. | | 2003/0100917 A1 | 5/2003 | Boyle et al. |
| 2002/0095171 A1 | 7/2002 | Belef | | 2003/0100918 A1 | 5/2003 | Duane |
| 2002/0095172 A1 | 7/2002 | Mazzocchi et al. | | 2003/0105484 A1 | 5/2003 | Boyle et al. |
| 2002/0095173 A1 | 7/2002 | Mazzocchi et al. | | 2003/0109824 A1 | 6/2003 | Anderson et al. |
| 2002/0095174 A1 | 7/2002 | Tsugita et al. | | 2003/0114879 A1 | 6/2003 | Euteneuer et al. |
| 2002/0099407 A1 | 7/2002 | Becker et al. | | 2003/0114880 A1 | 6/2003 | Hansen et al. |
| 2002/0103501 A1 | 8/2002 | Diaz et al. | | 2003/0120303 A1 | 6/2003 | Boyle et al. |
| 2002/0107541 A1 | 8/2002 | Vale et al. | | 2003/0125764 A1 | 7/2003 | Brady et al. |
| 2002/0111648 A1 | 8/2002 | Kusleika et al. | | 2003/0130680 A1 | 7/2003 | Russell |
| 2002/0111649 A1 | 8/2002 | Russo et al. | | 2003/0130681 A1 | 7/2003 | Ungs |
| 2002/0115942 A1 | 8/2002 | Stanford et al. | | 2003/0130682 A1 | 7/2003 | Broome et al. |
| 2002/0120286 A1 | 8/2002 | DoBrava et al. | | 2003/0130684 A1 | 7/2003 | Brady et al. |
| 2002/0120287 A1 | 8/2002 | Huter | | 2003/0130685 A1 | 7/2003 | Daniel et al. |
| 2002/0121472 A1 | 9/2002 | Gamer et al. | | 2003/0130686 A1 | 7/2003 | Daniel et al. |
| 2002/0123720 A1 | 9/2002 | Kusleika et al. | | 2003/0130687 A1 | 7/2003 | Daniel et al. |
| 2002/0123755 A1 | 9/2002 | Lowe et al. | | 2003/0130688 A1 | 7/2003 | Daniel et al. |
| 2002/0128679 A1 | 9/2002 | Turovskiy et al. | | 2003/0135162 A1 | 7/2003 | Deyette, Jr. et al. |
| 2002/0128680 A1 | 9/2002 | Pavlovic | | 2003/0135232 A1 | 7/2003 | Douk et al. |
| 2002/0128681 A1 | 9/2002 | Broome et al. | | 2003/0139764 A1 | 7/2003 | Levinson et al. |
| 2002/0133092 A1 | 9/2002 | Oslund et al. | | 2003/0144670 A1 | 7/2003 | Pavcnik et al. |
| 2002/0138094 A1 | 9/2002 | Borillo et al. | | 2003/0144685 A1 | 7/2003 | Boyle et al. |
| 2002/0138095 A1 | 9/2002 | Mazzocchi et al. | | 2003/0144686 A1 | 7/2003 | Martinez et al. |
| 2002/0143360 A1 | 10/2002 | Douk et al. | | 2003/0144687 A1 | 7/2003 | Brady et al. |
| 2002/0143361 A1 | 10/2002 | Douk et al. | | 2003/0144688 A1 | 7/2003 | Brady et al. |
| 2002/0151927 A1 | 10/2002 | Douk et al. | | 2003/0144689 A1 | 7/2003 | Brady et al. |
| 2002/0156456 A1 | 10/2002 | Fisher | | 2003/0150821 A1 | 8/2003 | Bates et al. |
| 2002/0156457 A1 | 10/2002 | Fisher | | 2003/0153942 A1 | 8/2003 | Wang et al. |
| 2002/0161390 A1 | 10/2002 | Mouw | | 2003/0153943 A1 | 8/2003 | Michael et al. |
| 2002/0161392 A1 | 10/2002 | Dubrui | | 2003/0158574 A1 | 8/2003 | Esch et al. |
| 2002/0161393 A1 | 10/2002 | Demond et al. | | 2003/0163064 A1 | 8/2003 | Vrba et al. |
| 2002/0161395 A1 | 10/2002 | Douk et al. | | 2003/0171770 A1 | 9/2003 | Kusleika et al. |
| 2002/0165576 A1 | 11/2002 | Boyle et al. | | 2003/0171771 A1 | 9/2003 | Anderson et al. |
| 2002/0169414 A1 | 11/2002 | Kletschka | | 2003/0171803 A1 | 9/2003 | Shimon |
| 2002/0169458 A1 | 11/2002 | Connors, III | | 2003/0176884 A1 | 9/2003 | Berrada et al. |
| 2002/0169472 A1 | 11/2002 | Douk et al. | | 2003/0176885 A1 | 9/2003 | Brome et al. |
| 2002/0169474 A1 | 11/2002 | Kusleika et al. | | 2003/0176886 A1 | 9/2003 | Wholey et al. |
| 2002/0173815 A1 | 11/2002 | Hogendijk et al. | | 2003/0181942 A1 | 9/2003 | Sutton et al. |
| 2002/0173817 A1 | 11/2002 | Kletschka et al. | | 2003/0181943 A1 | 9/2003 | Daniel et al. |
| 2002/0183873 A1 | 12/2002 | Miura et al. | | 2003/0187474 A1 | 10/2003 | Keegan et al. |
| 2002/0188313 A1 | 12/2002 | Johnson et al. | | 2003/0187475 A1 | 10/2003 | Tsugita et al. |
| 2002/0188314 A1 | 12/2002 | Anderson et al. | | 2003/0187495 A1 | 10/2003 | Cully et al. |
| 2002/0193825 A1 | 12/2002 | McGuckin, Jr. et al. | | 2003/0191493 A1 | 10/2003 | Epstein et al. |
| 2002/0193826 A1 | 12/2002 | McGuckin, Jr. et al. | | 2003/0195555 A1 | 10/2003 | Khairkhahan et al. |
| 2002/0193827 A1 | 12/2002 | McGuckin, Jr. et al. | | 2003/0199819 A1 | 10/2003 | Beck |
| 2002/0193828 A1 | 12/2002 | Griffin et al. | | 2003/0204168 A1 | 10/2003 | Bosma et al. |
| 2003/0004536 A1 | 1/2003 | Boylan et al. | | 2003/0208224 A1 | 11/2003 | Broome |
| 2003/0004537 A1 | 1/2003 | Boyle et al. | | 2003/0208225 A1 | 11/2003 | Goll et al. |
| 2003/0004539 A1 | 1/2003 | Linder et al. | | 2003/0208226 A1 | 11/2003 | Bruckhaimer et al. |
| 2003/0004540 A1 | 1/2003 | Linder et al. | | 2003/0208227 A1 | 11/2003 | Thomas |
| 2003/0004541 A1 | 1/2003 | Linder et al. | | 2003/0208228 A1 | 11/2003 | Gilson et al. |
| 2003/0009188 A1 | 1/2003 | Linder et al. | | 2003/0212361 A1 | 11/2003 | Boyle et al. |
| 2003/0009189 A1 | 1/2003 | Gilson et al. | | 2003/0212429 A1 | 11/2003 | Keegan et al. |
| 2003/0015206 A1 | 1/2003 | Roth et al. | | 2003/0212431 A1 | 11/2003 | Brady et al. |
| 2003/0018354 A1 | 1/2003 | Roth et al. | | 2003/0212434 A1 | 11/2003 | Thielen |
| 2003/0023265 A1 | 1/2003 | Forber | | 2003/0216774 A1 | 11/2003 | Larson |
| 2003/0028238 A1 | 2/2003 | Burkett et al. | | 2003/0220665 A1 | 11/2003 | Eskuri et al. |
| 2003/0032941 A1 | 2/2003 | Boyle et al. | | 2003/0225418 A1 | 12/2003 | Eskuri et al. |
| 2003/0032977 A1 | 2/2003 | Brady et al. | | 2003/0229295 A1 | 12/2003 | Houde et la. |
| 2003/0040772 A1 | 2/2003 | Hyodoh et al. | | 2003/0229374 A1 | 12/2003 | Brady et al. |
| 2003/0042186 A1 | 3/2003 | Boyle et al. | | 2003/0233117 A1 | 12/2003 | Adams et al. |
| 2003/0045898 A1 | 3/2003 | Harrison et al. | | 2004/0010282 A1* | 1/2004 | Kusleika ............ 606/200 |
| 2003/0057156 A1 | 3/2003 | Peterson et al. | | | | |
| 2003/0060782 A1 | 3/2003 | Bose et al. | | FOREIGN PATENT DOCUMENTS | | |
| 2003/0060843 A1 | 3/2003 | Boucher | | | | |
| 2003/0060844 A1 | 3/2003 | Borillo et al. | | EP | 0256683 | 2/1988 |
| 2003/0065354 A1 | 4/2003 | Boyle et al. | | EP | 0533511 | 3/1993 |
| 2003/0069596 A1 | 4/2003 | Eskuri | | EP | 0596172 | 5/1994 |
| 2003/0069597 A1 | 4/2003 | Petersen | | EP | 0655228 | 5/1995 |
| 2003/0078519 A1 | 4/2003 | Salahieh et al. | | EP | 0743046 | 11/1996 |
| 2003/0078614 A1 | 4/2003 | Salahieh et al. | | EP | 0759287 | 2/1997 |
| 2003/0083692 A1 | 5/2003 | Vrba et al. | | EP | 0791340 | 8/1997 |
| 2003/0083693 A1 | 5/2003 | Daniel et al. | | EP | 0827756 | 3/1998 |
| 2003/0093106 A1 | 5/2003 | Brady et al. | | EP | 1123688 | 8/2001 |

| | | | | | | |
|---|---|---|---|---|---|---|
| EP | 1127556 | 8/2001 | | WO | WO 00/67666 | 11/2000 |
| EP | 1149566 | 10/2001 | | WO | WO 00/67667 | 11/2000 |
| EP | 1172073 | 1/2002 | | WO | WO 00/67668 | 11/2000 |
| EP | 1181900 | 2/2002 | | WO | WO 00/67669 | 11/2000 |
| FR | 2 580 504 | 10/1986 | | WO | WO 00/67670 | 11/2000 |
| FR | 2 616 666 | 12/1988 | | WO | WO00/67671 | 11/2000 |
| FR | 2 768 326 | 3/1999 | | WO | WO 00/67829 | 11/2000 |
| GB | 2020557 | 11/1979 | | WO | WO 00/76390 | 12/2000 |
| GB | 2200848 | 8/1988 | | WO | WO 01/05329 | 1/2001 |
| WO | WO 88/09683 | 12/1988 | | WO | WO 01/08595 | 2/2001 |
| WO | WO 89/07422 | 8/1989 | | WO | WO 01/08596 | 2/2001 |
| WO | WO 94/24946 | 11/1994 | | WO | WO 01/08742 | 2/2001 |
| WO | WO 95/34254 | 12/1995 | | WO | WO 01/08743 | 2/2001 |
| WO | WO 95/34339 | 12/1995 | | WO | WO 01/10343 | 2/2001 |
| WO | WO 96/01591 | 1/1996 | | WO | WO 01/12082 | 2/2001 |
| WO | WO 96/39998 | 12/1996 | | WO | WO 01/15629 | 3/2001 |
| WO | WO 97/03810 | 2/1997 | | WO | WO 01/15630 | 3/2001 |
| WO | WO 97/17021 | 5/1997 | | WO | WO 01/21077 | 3/2001 |
| WO | WO 97/17100 | 5/1997 | | WO | WO 01/21100 | 3/2001 |
| WO | WO 97/17914 | 5/1997 | | WO | WO 01/35857 | 5/2001 |
| WO | WO 97/27808 | 8/1997 | | WO | WO 01/35858 | 5/2001 |
| WO | WO 97/42879 | 11/1997 | | WO | WO 01/43662 | 6/2001 |
| WO | WO 98/24377 | 6/1998 | | WO | WO 01/45590 | 6/2001 |
| WO | WO 98/30265 | 7/1998 | | WO | WO 01/45591 | 6/2001 |
| WO | WO 98/33443 | 8/1998 | | WO | WO 01/45592 | 6/2001 |
| WO | WO 98/38920 | 9/1998 | | WO | WO 01/49208 | 7/2001 |
| WO | WO 98/39053 | 9/1998 | | WO | WO 01/49209 | 7/2001 |
| WO | WO 98/46297 | 10/1998 | | WO | WO 01/49215 | 7/2001 |
| WO | WO 98/49952 | 11/1998 | | WO | WO 01/50982 | 7/2001 |
| WO | WO 98/50103 | 11/1998 | | WO | WO 01/52768 | 7/2001 |
| WO | WO 98/51237 | 11/1998 | | WO | WO 01/72205 | 10/2001 |
| WO | WO 99/16382 | 4/1999 | | WO | WO 01/80776 A1 | 11/2001 |
| WO | WO 99/20335 | 4/1999 | | WO | WO 01/80777 A2 | 11/2001 |
| WO | WO 99/22673 | 5/1999 | | WO | WO 01/82830 | 11/2001 |
| WO | WO 99/23976 | 5/1999 | | WO | WO 01/82831 | 11/2001 |
| WO | WO 99/25252 | 5/1999 | | WO | WO 01/87183 | 11/2001 |
| WO | WO 99/44510 | 9/1999 | | WO | WO 01/89413 | 11/2001 |
| WO | WO 99/44542 | 9/1999 | | WO | WO 01/97714 | 12/2001 |
| WO | WO 99/51167 | 10/1999 | | WO | WO 02/043595 | 6/2002 |
| WO | WO 99/55236 | 11/1999 | | WO | WO 02/022325 | 10/2002 |
| WO | WO 00/07521 | 2/2000 | | WO | WO 02/083225 | 10/2002 |
| WO | WO 00/07656 | 2/2000 | | WO | WO 03/047648 | 6/2003 |
| WO | WO 00/16705 | 3/2000 | | WO | WO 03/084434 | 10/2003 |
| WO | WO 00/21604 | 4/2000 | | WO | WO 03/084435 | 10/2003 |
| WO | WO 00/44428 | 8/2000 | | WO | WO 03/084436 | 10/2003 |
| WO | WO 00/49970 | 8/2000 | | WO | WO 03/088805 | 10/2003 |
| WO | WO 00/56390 | 9/2000 | | WO | WO 03/088869 | 10/2003 |
| WO | WO 00/66031 | 11/2000 | | | | |
| WO | WO 00/67664 | 11/2000 | | * cited by examiner | | |
| WO | WO 00/67665 | 11/2000 | | | | |

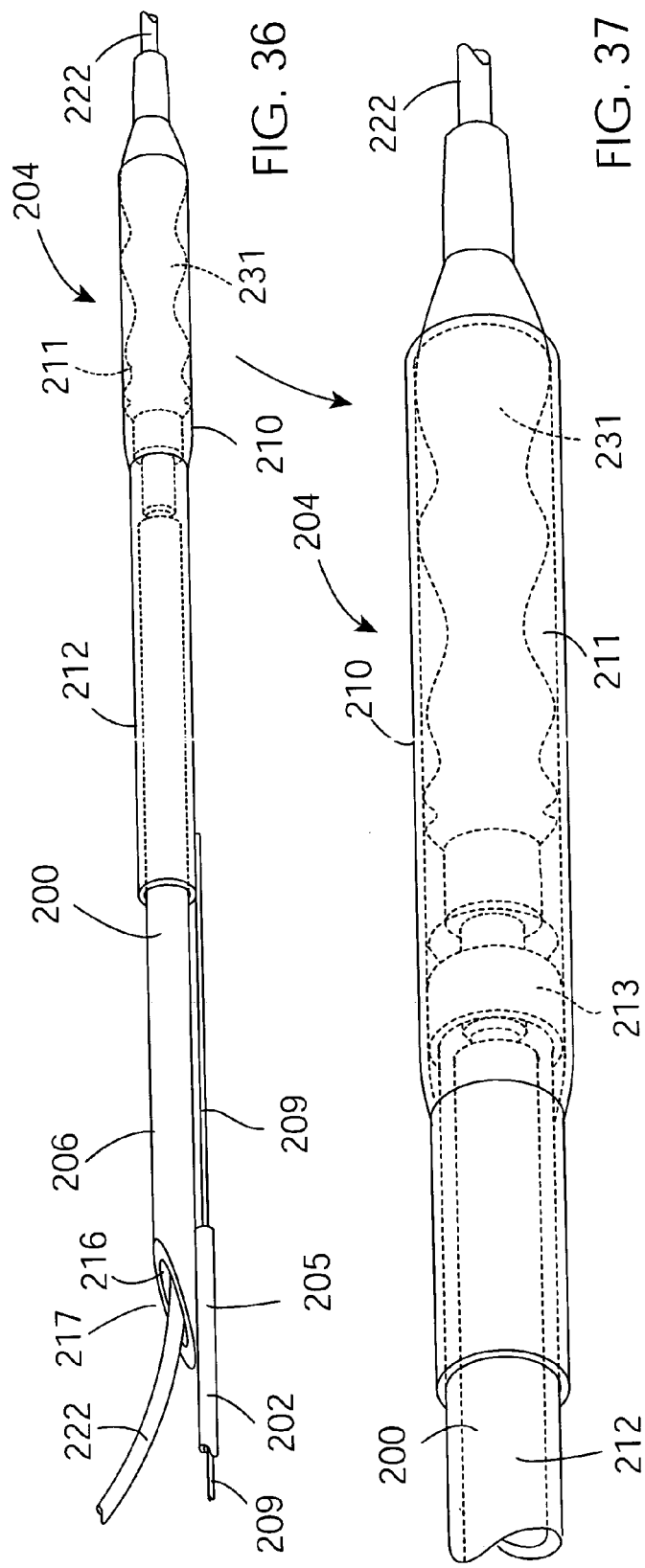
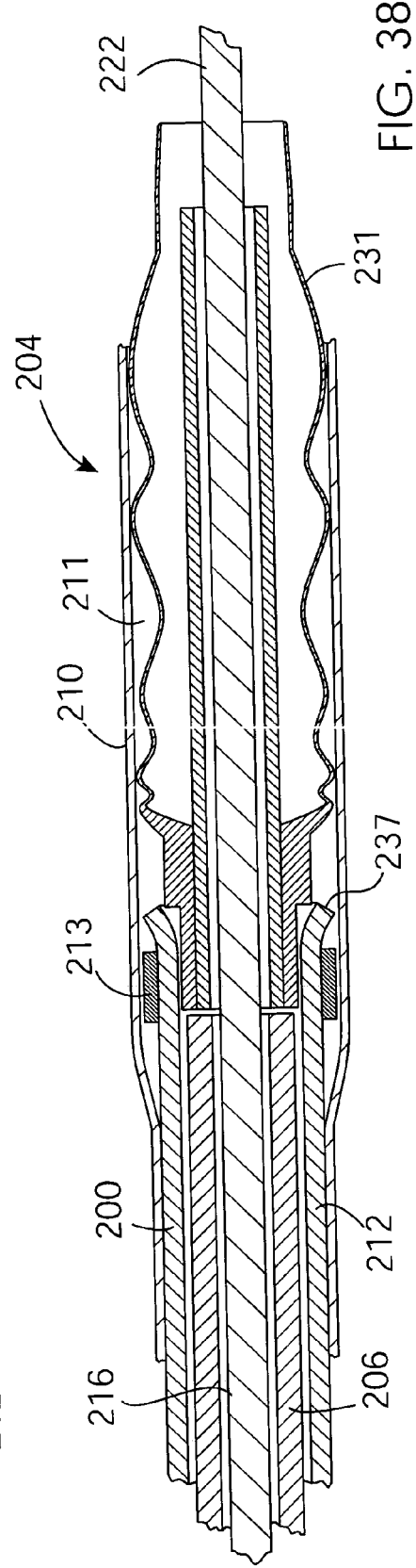
FIG. 36
FIG. 37
FIG. 38

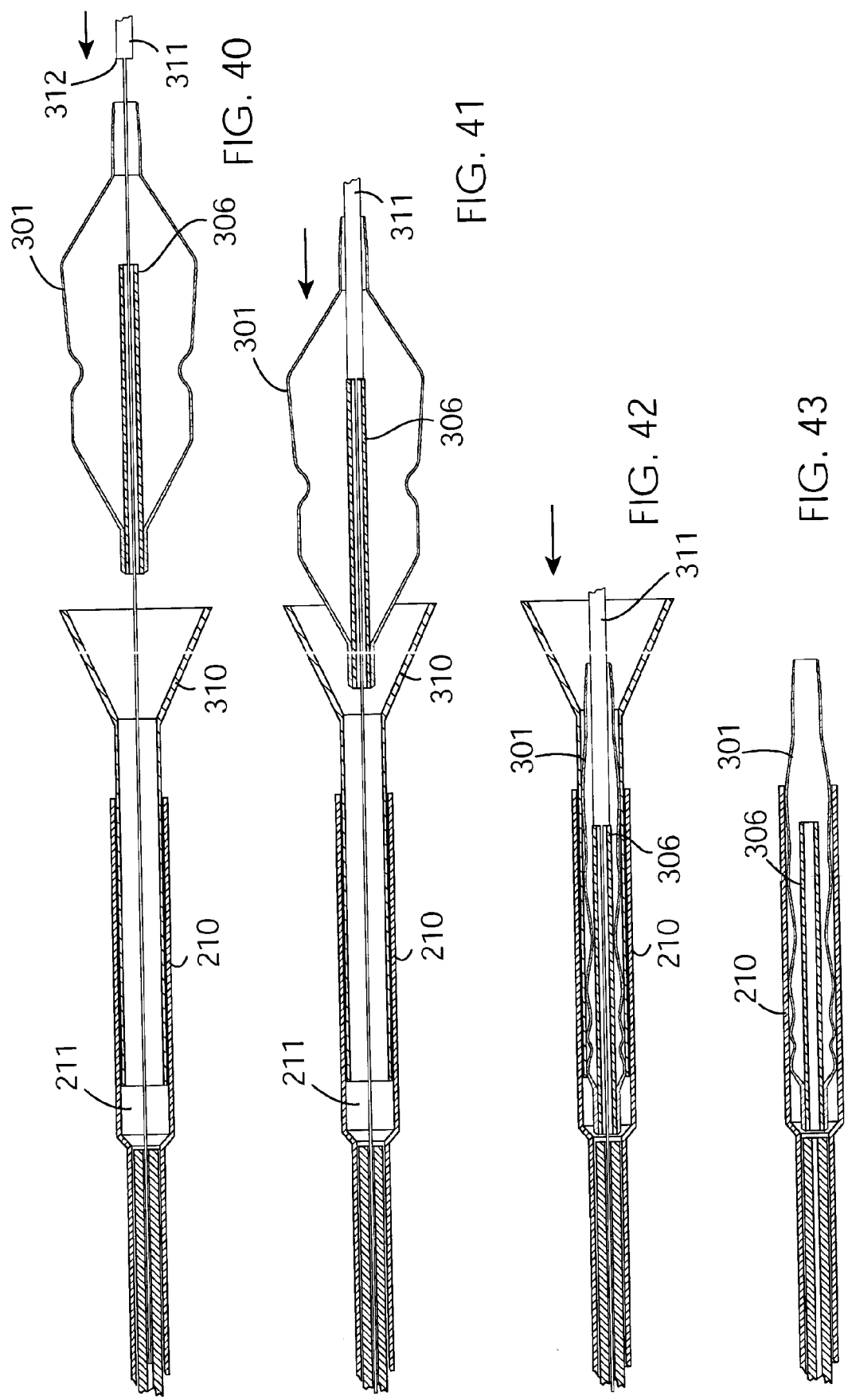

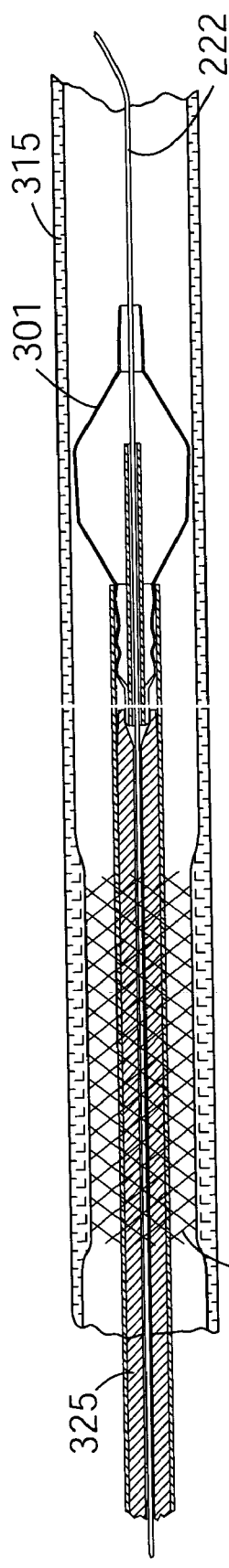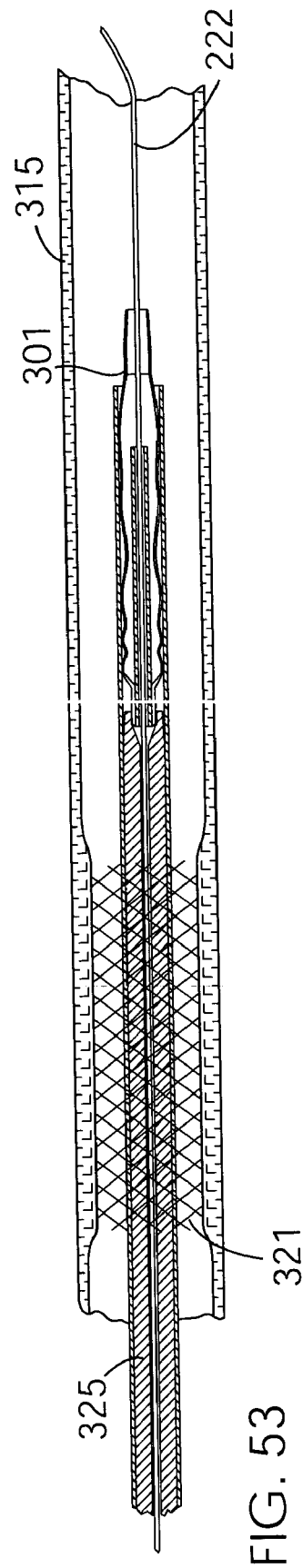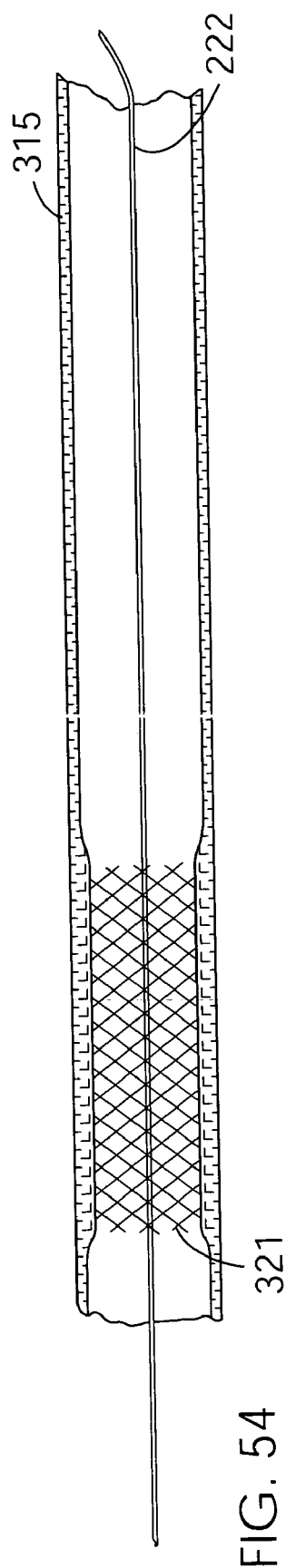

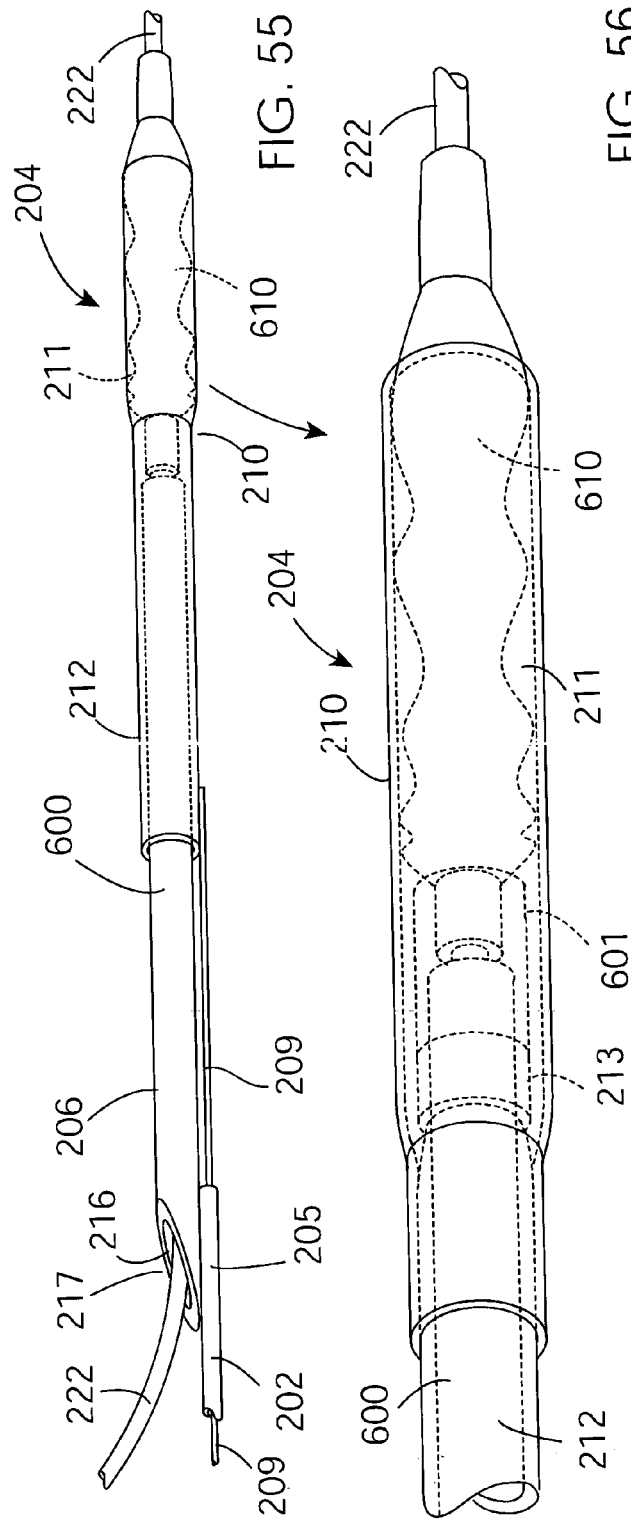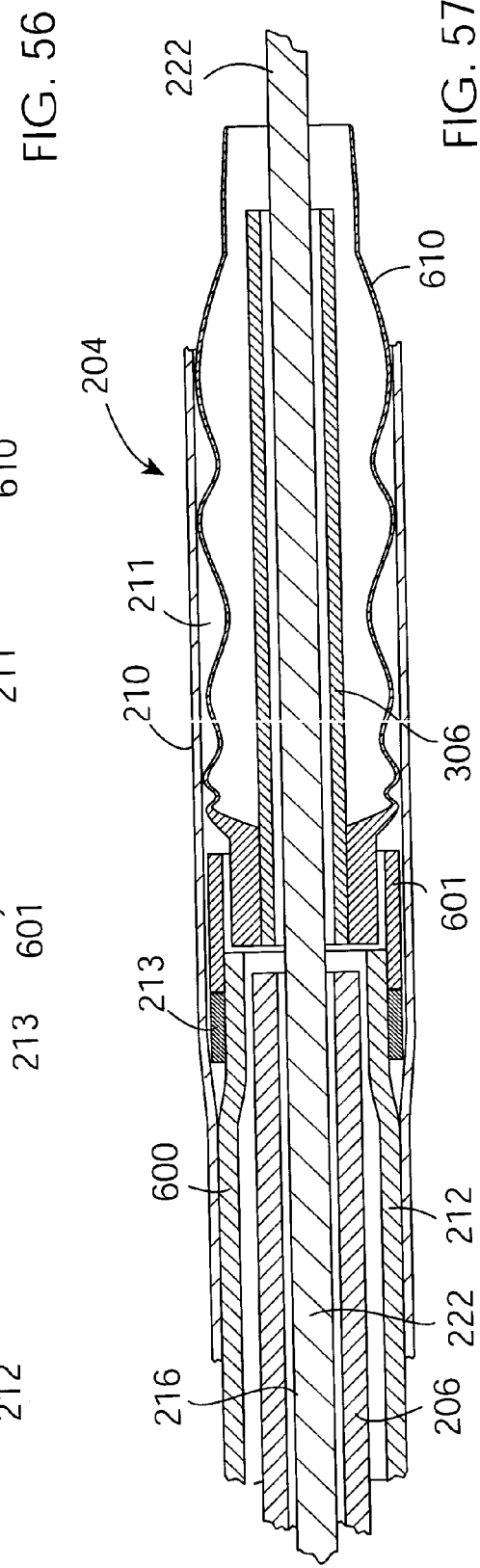

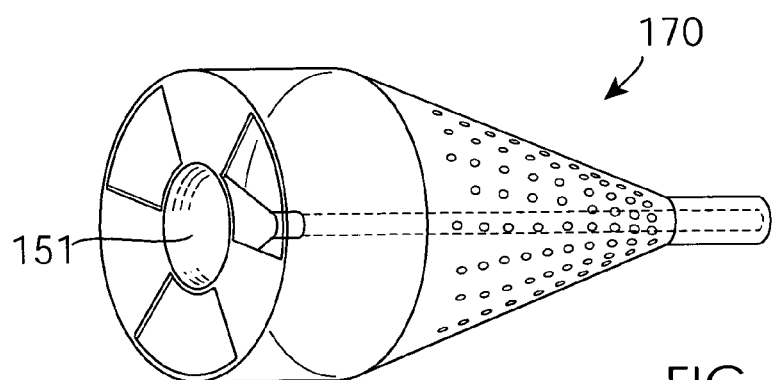
FIG. 115
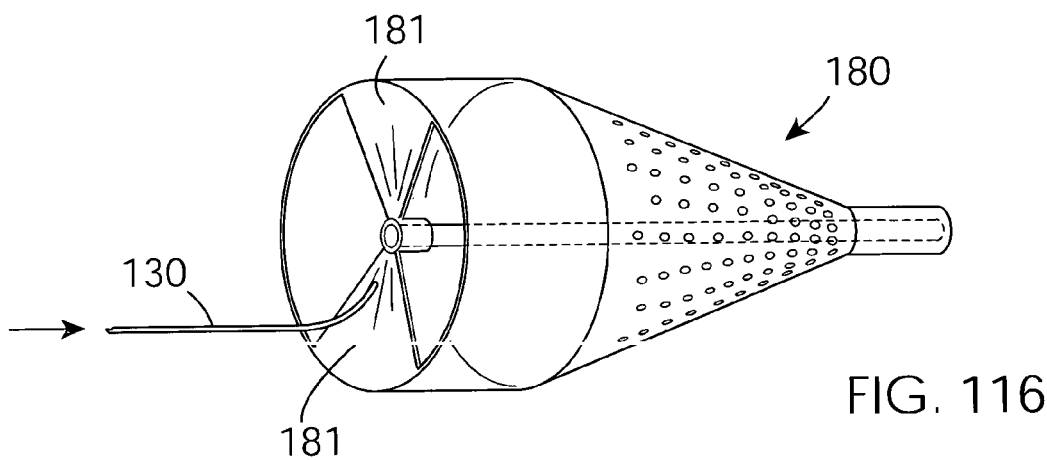
FIG. 116
FIG. 117
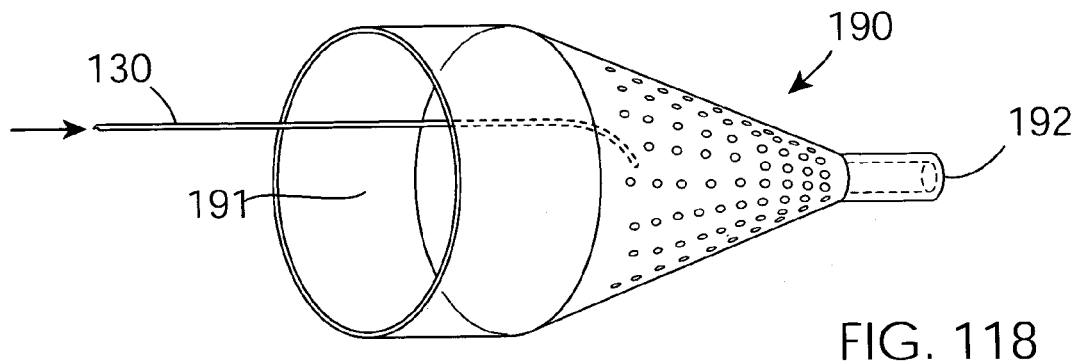
FIG. 118

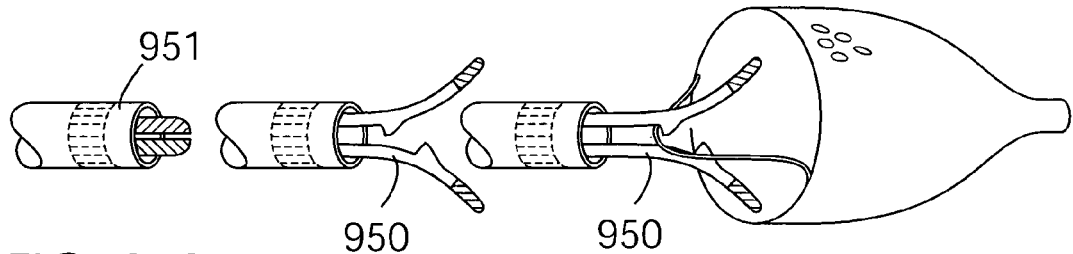
FIG. 213   FIG. 214
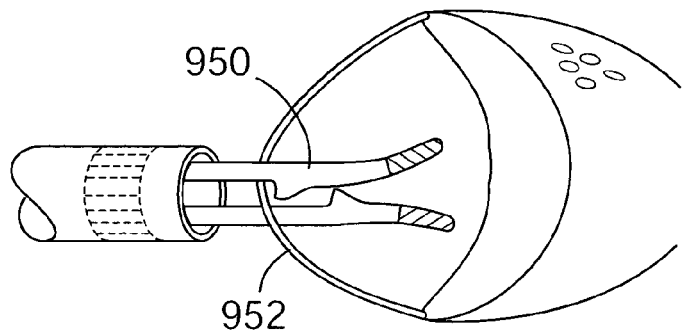
FIG. 215
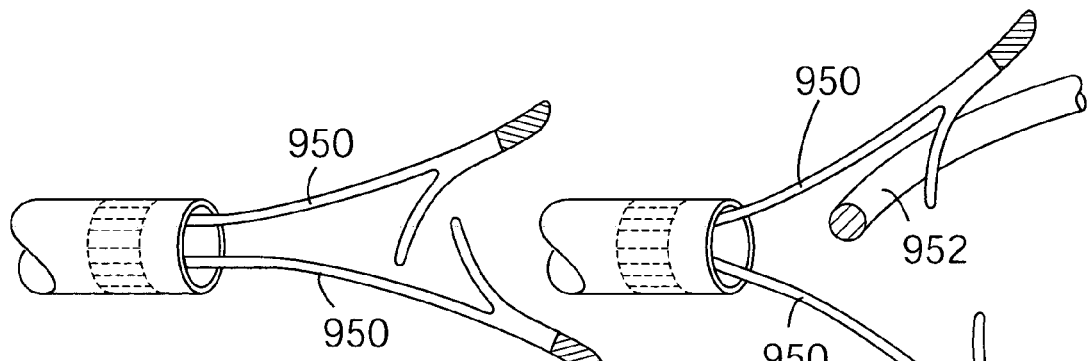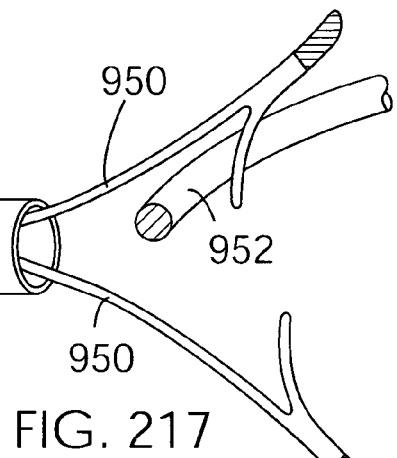
FIG. 216   FIG. 217
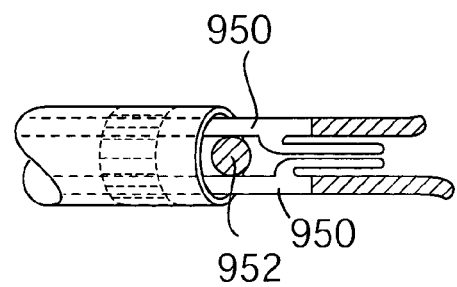
FIG. 218

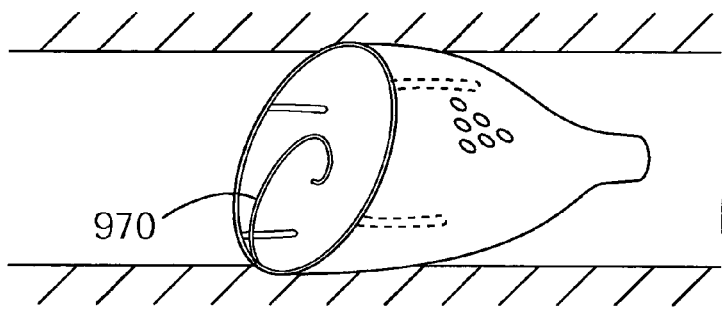
FIG. 225
FIG. 226
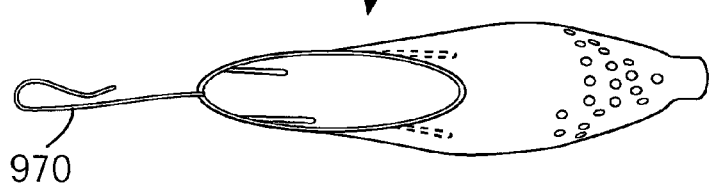
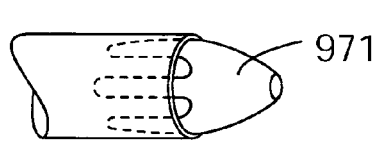
FIG. 227
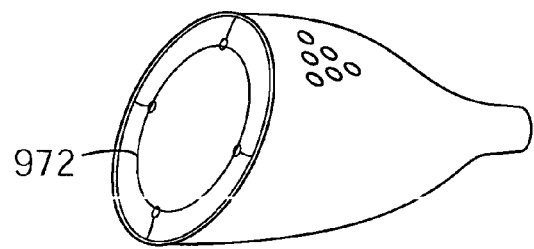
FIG. 228
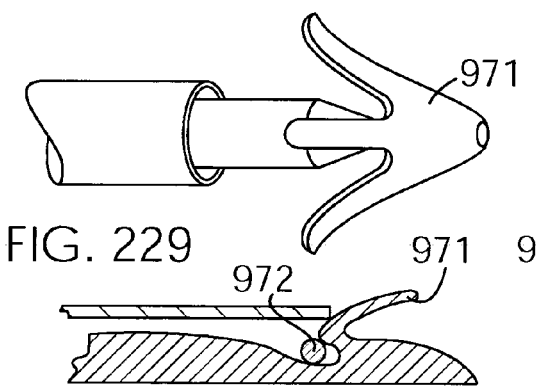
FIG. 229
FIG. 229A
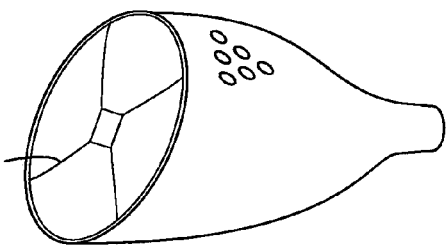
FIG. 230
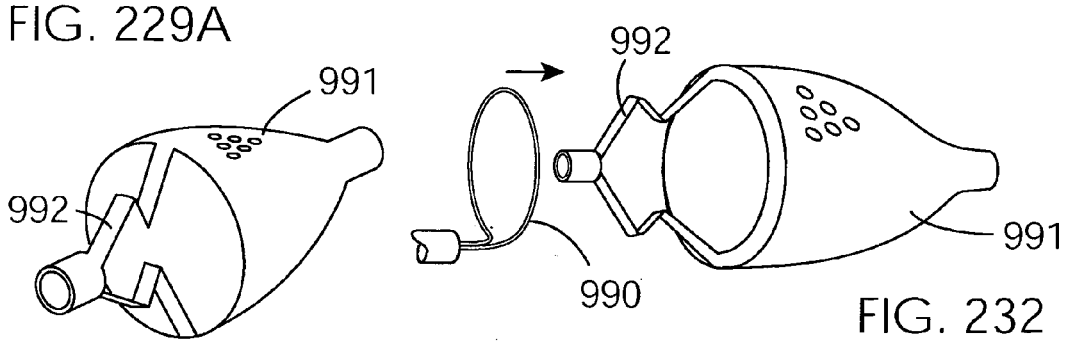
FIG. 231
FIG. 232

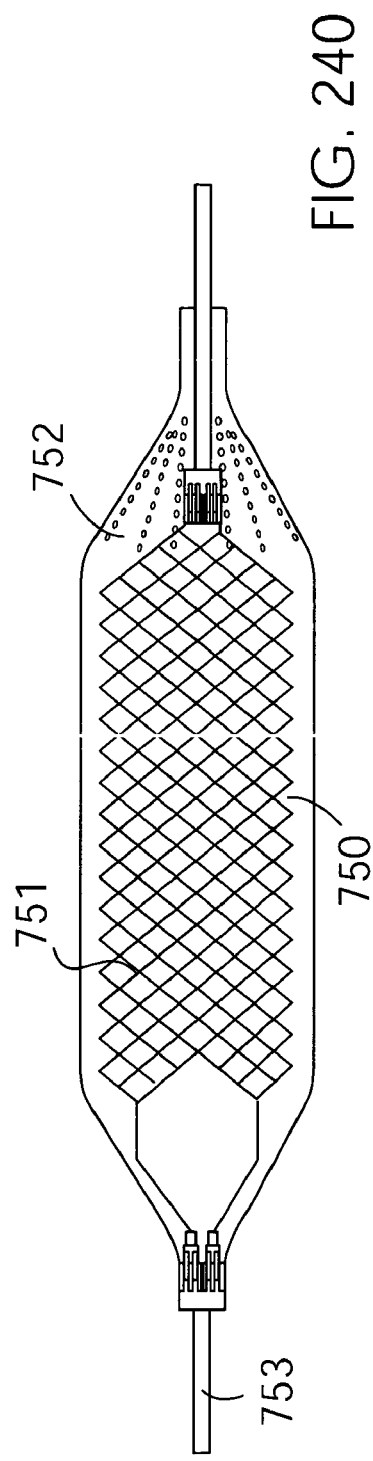
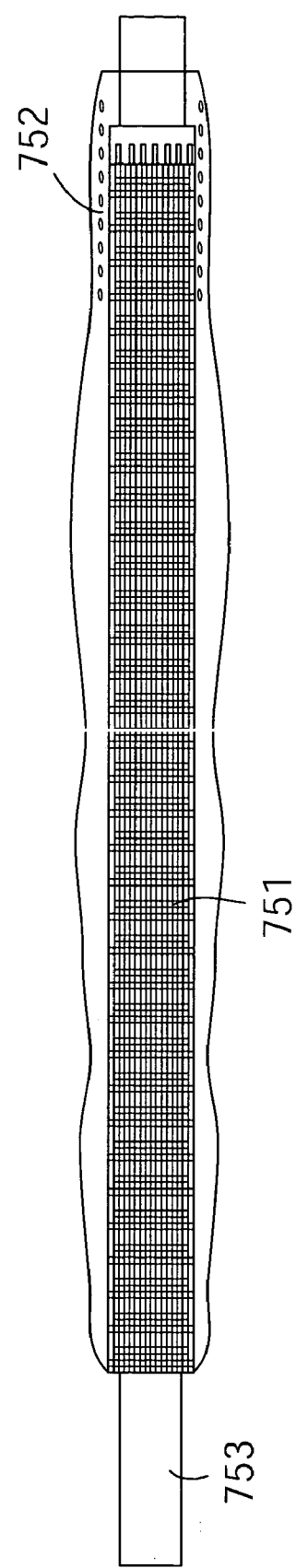
FIG. 240
FIG. 241

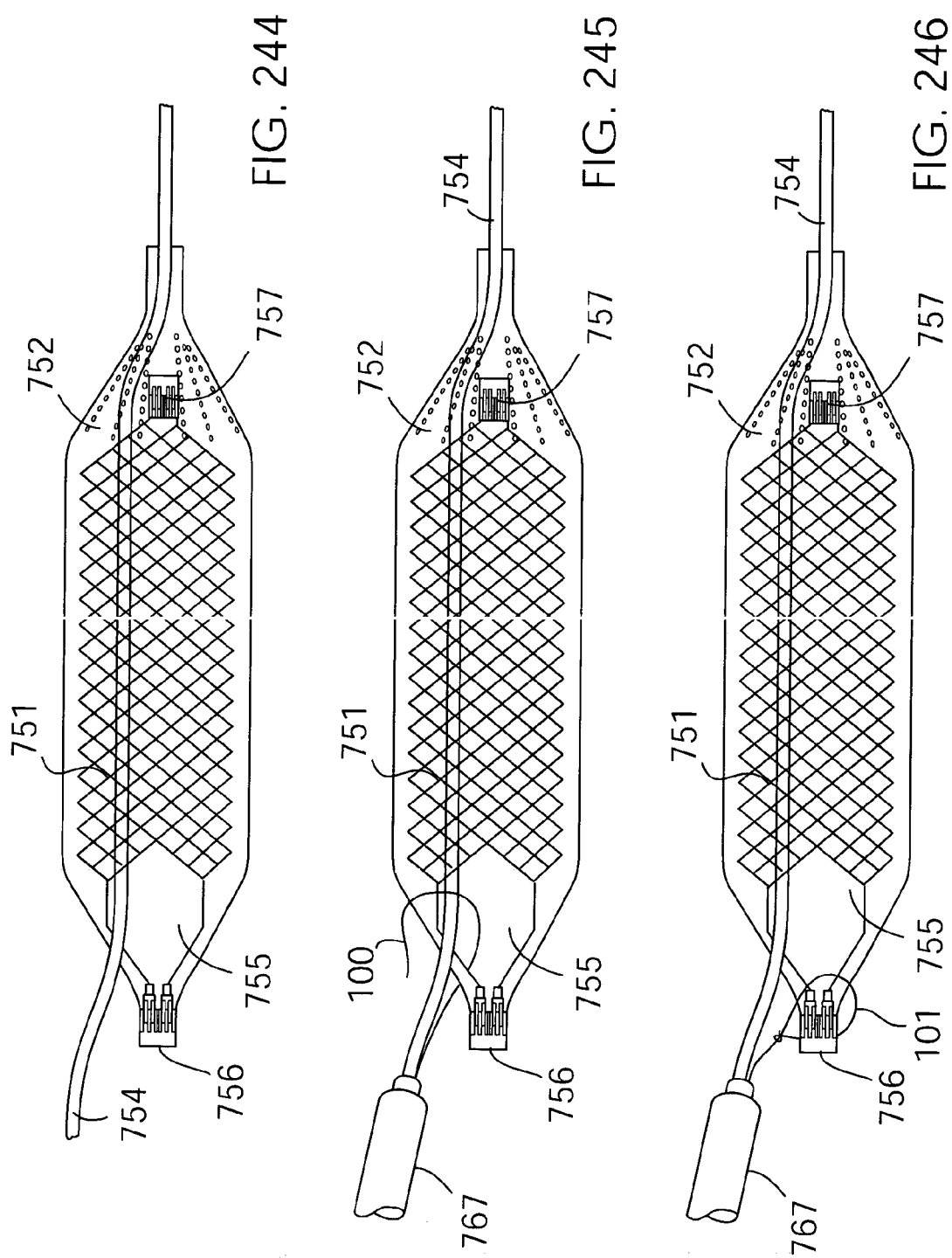

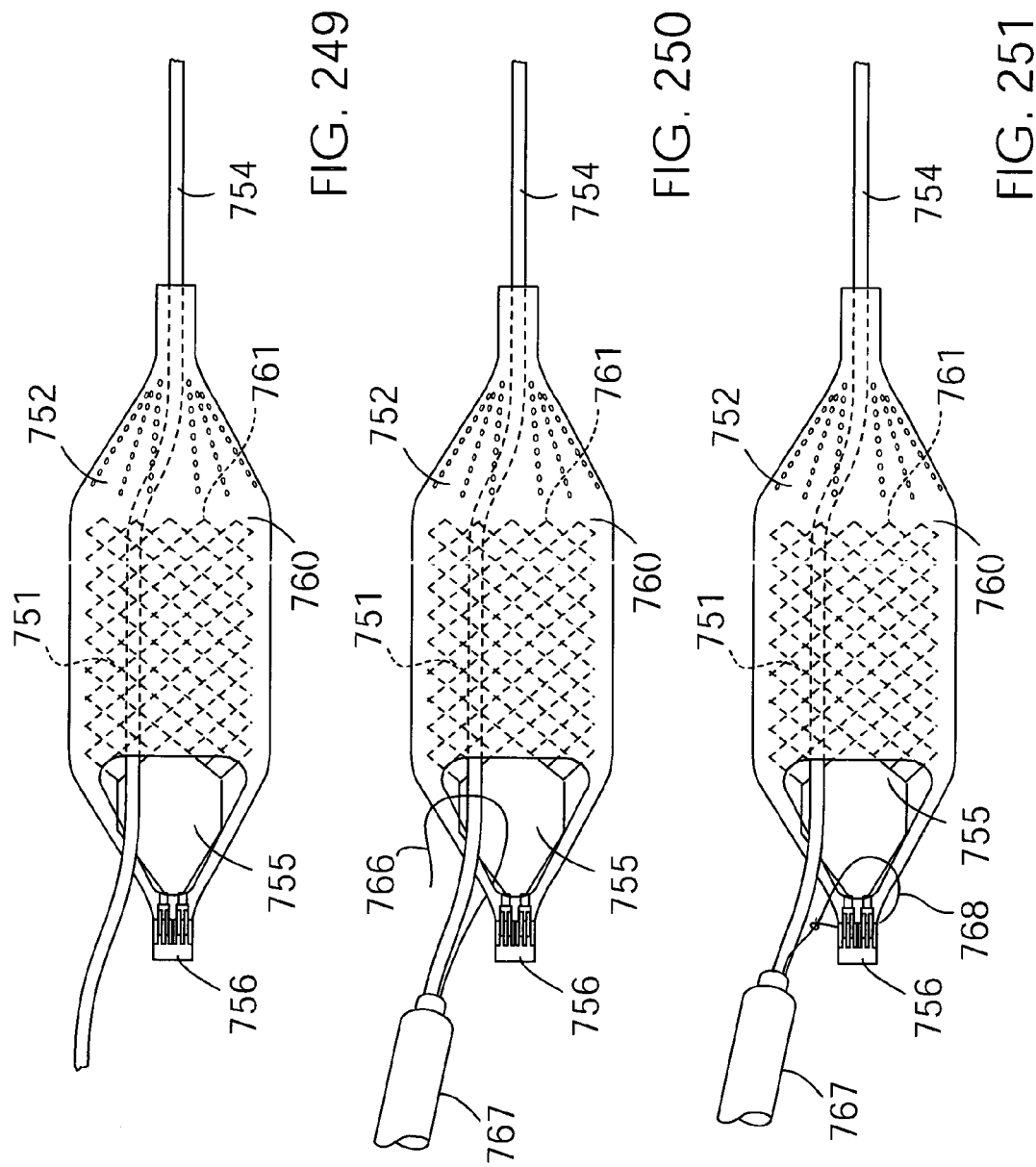

EMBOLIC PROTECTION SYSTEM

This application claims the benefit of provisional application No. 60/361,340, filed on Mar. 5, 2002, the content of which is incorporated herein by reference.

INTRODUCTION

This invention relates to a transvascular embolic protection system for safely capturing and retaining embolic material released during an interventional procedure while maintaining blood flow.

Embolic protection systems of this general type are described in our published international patent applications WO 01/80776 and WO 01/80777.

There is an economical and clinical need to provide an embolic protection system which will be easy and convenient for a clinician to prepare for use, to deploy and to retrieve. In addition there is a need to provide such a system which is suitable for use with standard medical equipment and will facilitate a wide range of clinical procedures to be carried out.

STATEMENTS OF INVENTION

According to the invention there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature;

the filter at least in the collapsed configuration having a guidewire lumen defined at least partially therethrough for passing the filter over a guidewire;

wherein the guidewire lumen is defined by a lumen-defining member which is spaced proximally of the distal end of the filter.

According to one embodiment, the guidewire lumen is defined by a tubular member.

In another embodiment, the tubular member is mounted to the filter.

According to one embodiment, the filter comprises a snare engaging feature.

In another embodiment, the snare engaging feature is radiopaque.

According to the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature;

the filter at least in the collapsed configuration having a guidewire lumen defined at least partially therethrough for passing the filter over a guidewire;

wherein the guidewire lumen is defined by a lumen-defining member which is movable or removable reactive to the filter.

In one embodiment, the lumen-defining member is a substantially tubular member.

In one embodiment, the tubular member has a slit extending the length thereof for removal of the member from a guidewire.

In another embodiment, the lumen-defining member comprises a portion of a delivery system.

Preferably the lumen-defining member comprises a pusher element of the delivery system, the pusher being movable from an extended lumen-defining configuration for loading of a filter to a retracted configuration for deployment of the filter.

According to another aspect of the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature in apposition with a vasculature wall;

in the outwardly extended configuration the filter exerting an outward radial force on a vasculature wall sufficient to retain the filter in position against substantial longitudinal movement.

In one embodiment, the filter comprises a filter body and a filter support frame to support the filter body in the outwardly extended configuration in apposition with a vasculature wall, the filter support frame providing the outward radial force.

In one embodiment, the filter comprises a low-friction outer layer.

Preferably the outer layer is of a hydrophilic material.

In one embodiment, the filter comprises an inflatable member to enhance the outward radial force.

In another embodiment, the filter defines a guidewire lumen for passing the filter over a guidewire.

In one embodiment, the filter comprises an anchor for fixing the filter to the vasculature in the deployed configuration.

In another embodiment, the filter comprises a filter body and a filter support frame to support the filter body in the deployed configuration.

In one embodiment, the support frame comprises the anchor.

In one embodiment, the filter body comprises the anchor.

In another embodiment, the anchor comprises a plurality of anchor elements.

In one embodiment, the anchor elements are spaced-apart circumferentially around the filter when the filter is in the deployed configuration.

In one embodiment, the support frame comprises at least one support hoop.

In another embodiment, the support frame has a longitudinal aspect.

In a further embodiment, the filter is self supported in a vasculature in the absence of a guidewire.

According to another aspect of the invention, there is provided an embolic protection filter assembly for deployment in a vasculature, the assembly comprising:— a filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter; and a receiver to guide a docking device into association with the filter.

In one embodiment, the filter has a guidewire lumen for passing the filter over a guidewire, and the receiver is configured to guide a guidewire into the guidewire lumen.

In one embodiment, the guidewire lumen extends only partially through the filter.

In another embodiment, the receiver is configured to guide a coupling member towards the filter for coupling to the filter.

In one embodiment, the receiver comprises a funnel.

In another embodiment, the funnel is movable between a collapsed configuration for movement through a vasculature, and an outwardly extended configuration for guiding a docking device.

In one embodiment, the funnel is biased towards the outwardly extended configuration.

In another embodiment, the funnel comprises a funnel body and a funnel support to support the funnel body in the outwardly extended configuration.

In one embodiment, the funnel body comprises a membrane.

In a further embodiment, the funnel support comprises a plurality of pivotable fingers.

Preferably the receiver comprises an approach channel.

In one embodiment, the channel is provided by a lumen in a catheter.

In another embodiment, the receiver is mounted to the filter.

In one embodiment, the receiver is detachably mounted to the filter.

In another embodiment, the receiver is separate from the filter.

In a further embodiment, the receiver has means to space the receiver from the wall of a vasculature.

Preferably the spacing means comprises an inflatable member to engage the wall of a vasculature.

In one embodiment, the receiver is at least partially provided by a wall of the filter.

In another embodiment, the receiver is at least partially provided by a wall of the filter at the inlet end of the filter.

In a further embodiment, the receiver is at least partially provided by a wall of the filter at the outlet end of the filter.

In one embodiment, the receiver extends proximally of the inlet end of the filter.

In another embodiment, the receiver is located distally of the inlet end of the filter.

In a further embodiment, the receiver is radially offset from the longitudinal axis of the filter.

According to another aspect of the invention there is provided, an embolic protection system comprising:—
an embolic protection filter assembly and
a docking device which may be guided by the receiver into association with the filter.

In one embodiment, the docking device comprises a guidewire.

In one embodiment, the docking device comprises a coupling member.

According to another aspect of the invention, there is provided an embolic protection filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter having a guidewire aperture for passing the filter over a guidewire; and the filter comprising a seal to seal the guidewire aperture. Preferably the seal is self-closing.

In one embodiment, the seal is located at a proximal end of the filter, and/or at a distal end of the filter.

In one embodiment, the filter has a tubular member extending from the guidewire aperture to define a guidewire lumen through the tubular member.

In another embodiment, the tubular member extends through at least part of the filter.

In one embodiment, the tubular member is radially offset from the longitudinal axis of the filter.

In one embodiment, the seal is an annular member around the guidewire aperture, the annular member being closable down to seal the guidewire aperture.

Preferably the annular member is a tube.

In one embodiment, the annular member comprises a soft membrane.

In one embodiment, the annular member comprises two or more circumferentially overlapping flaps.

According to a further aspect of the invention, there is provided a retrieval catheter for retrieving a medical device deployed in a vasculature, the catheter comprising:—
an outer catheter body; and
an inner coupling member having means for coupling to a medical device deployed in a vasculature;
the catheter body being movable distally relative to the coupling member to retrieve a coupled medical device into the catheter body.

In one embodiment, the coupling means comprises a male or female member on the coupling member for engagement with a corresponding female or male member on the medical device.

In one embodiment, the male member is movable between a low-profile configuration and an outwardly protruding configuration.

In one embodiment, the male member is biased towards the outwardly protruding configuration.

In another enbodiment the male member is of a resilient material.

Preferably the coupling means is substantially arrow-head shaped.

In one embodiment, the male member is in the form of a hook for hooking around a female member on the medical device.

In one embodiment, the male member is in the form of a hook for hooking around a tether arm on the medical device.

In one embodiment, the tether arm is at a proximal end of the medical device.

In another embodiment, the tether arm is located within the medical device.

In one embodiment, the coupling means comprises at least one female member on the coupling member for engagement with at least one male member on the medical device.

In one embodiment, the female member is in the form of a loop for looping around a protruding male member on the medical device.

In one embodiment, the coupling means comprises a pair of jaws on the coupling member, the jaws being movable between an outwardly protruding configuration and a low-profile configuration to grasp the medical device.

In one embodiment, the retrieval catheter comprises an actuator to move the jaws to the outwardly protruding configuration.

In another embodiment, the actuator is movable longitudinally relative to the jaws to move the jaws in a camming arrangement to the outwardly protruding configuration.

In a further embodiment, the jaws are biased towards the low-profile configuration.

In one embodiment, the catheter body is engageable with the jaws to move the jaws to the low-profile configuration.

In another embodiment, the jaws are biased towards the outwardly protruding configuration.

In a further embodiment, the coupling member is at least partially of a magnetic material for magnetic coupling to an oppositely charged magnetic portion of the medical device.

In one embodiment, the retrieval catheter comprises means to axially elongate a deployed medical device to collapse the medical device to a low-profile configuration for retrieval into the catheter body.

In one embodiment, the elongation means comprises a second coupling member movable relative to the first coupling member to collapse the medical device.

In another embodiment, the second coupling member comprises a pusher member movable distally relative to first coupling member to engage a deployed medical device distally of the first coupling means and thereby collapse the medical device.

In a further embodiment, the catheter body has a guidewire lumen extending partially therethrough for passing the catheter body over a guidewire in a rapid exchange manner.

In one embodiment, the guidewire lumen is offset radially from the coupling member.

According to one embodiment, there is provided a retrieval catheter for retrieving an embolic protection filter deployed in a vasculature.

In another aspect of the invention there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature;

the filter at least in the collapsed configuration having a guidewire lumen defined at least partially therethrough for passing the filter over a guidewire;

wherein the guidewire lumen is defined by a lumen-defining member which is spaced proximally of the distal end of the filter.

In one embodiment, the guidewire lumen is defined by a tubular member.

In another embodiment, the tubular member is mounted to the filter.

Preferably the filter comprises a snare engaging feature.

Preferably the snare engaging feature is radiopaque.

In another aspect the invention provides a method for the capture and removal of embolic material from a vasculature during an interventional procedure comprising the steps of:— providing a collapsible embolic protection filter having a collapsed configuration for delivery of the filter, and a deployed configuration;

advancing a guidewire through a vasculature;

crossing a desired treatment location with the guidewire;

deploying the filter distal to the treatment location;

carrying out an interventional procedure at the treatment location, embolic material generated during the treatment procedure being captured by the deployed filter;

advancing a retrieval device;

engaging the filter with the retrieval device independent of the guidewire; and withdrawing the retrieval device and the filter from the vasculature.

In one case, after crossing a treatment location with the guidewire the embolic protection device is introduced over the guidewire.

In one case, the deployed filter is retained independent of the guidewire against substantial longitudinal movement.

In another case, the filter applies a radial force to the vasculature to substantially prevent movement of the filter relative to the vasculature in the deployed configuration.

In one case, the filter in the deployed configuration is anchored to the vasculature.

In one case, the method comprises the step of releasing the filter from the vasculature before retrieving the filter.

In another case, the filter is simultaneously released and retrieved by moving a retrieval catheter distally relative to the filter.

In one case the filter is released prior to retrieving the filter.

In one case, the method comprises the step of axially elongating the filter to release the filter.

According to another aspect the method comprises the steps of:— withdrawing the guidewire from the filter and/or the desired treatment location; and subsequently placing a guidewire in the filter.

In one case, the same guidewire is placed in the filter.

In another case, another guidewire is placed in the filter.

In one case, the interventional device is introduced over the guidewire for carrying out the interventional procedure.

In one case, the interventional procedure comprises a stenting of the treatment location.

In another case, the interventional procedure comprises a balloon angioplasty procedure at the treatment location.

According to another aspect the invention provides a method for the capture and removal of embolic material from a vasculature during an interventional procedure comprising the steps of:— advancing a guidewire through a vasculature;

crossing a desired treatment location with the guidewire;

introducing over the guidewire a collapsible embolic protection filter having a collapsed configuration for delivery of the filter, and a deployed configuration;

deploying the filter distal to the treatment location;

the filter in the deployed configuration being retained in apposition with the vasculature independent of the guidewire against substantial longitudinal movement;

carrying out an interventional procedure at the treatment location, embolic material generated during the treatment procedure being captured by the deployed filter;

advancing a retrieval device;

engaging the filter with the retrieval device; and withdrawing the retrieval device and the filter from the vasculature.

In one case, on the filter applies a radial force to the vasculature to substantially prevent movement of the filter relative to the vasculature in the deployed configuration.

Preferably the filter in the deployed configuration is anchored to the vasculature.

In one case, the filter is engaged with the retrieval device independent of the guidewire.

According to another aspect the method comprises the step of releasing the filter from the vasculature before retrieving the filter.

According to a further aspect, the retrieval device is a retrieval catheter and the filter is simultaneously released and retrieved by moving the retrieval catheter distally relative to the filter.

In one case, the filter is released prior to retrieving the filter.

According to one aspect, the method comprises the step of axially elongating the filter to release of the filter.

Preferably the method comprises the steps of:—
withdrawing the guidewire from the filter and the desired treatment location; and
subsequently placing a guidewire in the filter.

According to a one aspect, the same guidewire is placed in the filter.

According to a another aspect, another guidewire is placed in the filter.

In one case, the interventional device is introduced over the guidewire for carrying out the interventional procedure.

Preferably the interventional procedure comprises a stenting of the treatment location.

According to one aspect, the interventional procedure comprises a balloon angioplasty procedure at the treatment location.

According to a further aspect a method for the capture and removal of embolic material from a vasculature during an interventional procedure comprising the steps of:—
providing a collapsible embolic protection filter having a collapsed configuration for delivery of the filter, and a deployed configuration;
advancing a guidewire through a vasculature;
crossing a desired treatment location with the guidewire;
deploying the filter distal to the treatment location;
withdrawing the guidewire from the filter and/or the desired treatment location; and
subsequently placing a guidewire in the filter;
carrying out an interventional procedure at the treatment location, embolic material generated during the treatment procedure being captured by the deployed filter;
advancing a retrieval device;
engaging the filter with the retrieval device; and
withdrawing the retrieval device and the filter from the vasculature.

In one case, the same guidewire is placed in the filter.

In another case, another guidewire is placed in the filter.

In one case the interventional device is introduced over the guidewire for carrying out the interventional procedure.

In another case, the interventional procedure comprises a stenting of the treatment location.

In one case, the interventional procedure comprises a balloon angioplasty procedure at the treatment location.

In one case, the filter is engaged with the retrieval device independent of the guidewire.

In another case, after crossing a treatment location with the guidewire the embolic protection device is introduced over the guidewire.

Preferably the deployed filter is retained independent of the guidewire against substantial longitudinal movement.

In one case, on deployment, the filter applies a radial force to the vasculature to substantially prevent movement of the filter relative to the vasculature in the deployed configuration.

In one case, the filter in the deployed configuration is anchored to the vasculature.

In one case, the method comprises the step of releasing the filter from the vasculature before retrieving the filter.

In another case, the filter is simultaneously released and retrieved by moving a retrieval catheter distally relative to the filter.

In another case, the filter is released prior to retrieving the filter.

According to one aspect, the method comprises the step of axially elongating the filter to release the filter.

According to a further aspect the invention provides a method of retrieving a medical device from a vasculature, the method comprising the steps of:—
advancing a retrieval catheter through a vasculature until a distal end of the retrieval catheter is proximally of the deployed medical device;
axially elongating an element of the medical device to collapse the medical device; and
moving the retrieval catheter distally relative to the collapsed medical device to retrieve the medical device into the retrieval catheter.

In one case, the method comprises the steps of:— engaging a first coupling member with the element of the deployed medical device;

engaging a second coupling member with the element of the deployed medical device; and moving the coupling members relative to one another to axially elongate the element of the medical device.

According to another aspect of the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;
the filter being movable between a collapsed configuration for movement through a vasculature, and an outwardly extended configuration for deployment in a vasculature;
the filter at least in the collapsed configuration having a guidewire lumen defined at least partially therethrough for passing the filter over a guidewire;
wherein the tubular member is shortenable upon movement of the filter from the collapsed configuration to the extended configuration.

In one embodiment, the tubular member comprises at least two telescopable tubes.

According to another aspect of the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;
the filter being movable between a collapsed configuration for movement through a vasculature, and an outwardly extended configuration for deployment in a vasculature;

the filter at least in the collapsed configuration having a guidewire lumen defined at least partially therethrough for passing the filter over a guidewire;

wherein the filter comprises a support structure, in the collapsed configuration the support structure forming a tubular member to define the guidewire lumen.

According to another aspect the invention provides a method for the capture and removal of embolic material from a vasculature during an interventional procedure comprising the steps of:— advancing a guidewire through a vasculature;

crossing a desired treatment location with the guidewire;

introducing over the guidewire a collapsible embolic protection filter having a collapsed configuration for delivery and withdrawal of the filter, and a deployed configuration;

deploying the filter distal to the treatment location;

carrying out an interventional procedure at the treatment location, embolic material generated during the treatment procedure being captured by the deployed filter;

advancing a retrieval catheter;

fixing an abutment to the guidewire;

engaging the guidewire abutment with the filter to prevent movement of the filter distally of the guidewire abutment;

collapsing the filter and retrieving the filter into the retrieval catheter and with it the captured embolic material; and withdrawing the retrieval catheter and the collapsed filter from the vasculature.

In one case, the abutment is fixed to the guidewire during deployment of the filter.

In another case, the abutment is fixed to the guidewire before advancing the guidewire through the vasculature.

According to another aspect of the invention there is provided a retrieval catheter for retrieving a medical device deployed in a vasculature, the catheter comprising:— a first coupling member having means for coupling to a medical device deployed in a vasculature; and a second coupling member having means for coupling to the deployed medical device;

the coupling members being relatively movable to axially elongate the medical device and collapse the medical device.

In one embodiment, the catheter comprises an outer catheter body movable distally relative to the coupling members to retrieve a collapsed medical device into the catheter body.

According to another aspect of the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter; and the filter comprising an inflatable member to exert an outward radial force on a vasculature wall sufficient to retain the filter in position against substantial longitudinal movement.

According to a further aspect of the invention there is provided an embolic protection filter system comprising:— a collapsible embolic protection filter having a collapsed configuration for delivery of the filter, and a deployed configuration; and a snare for engaging the filter.

In one embodiment, the filter has a snare engaging feature for engagement by the snare.

In one embodiment, the filter comprises a support frame and the snare engaging feature is provided by or on the support frame.

Preferably the snare is radiopaque at least in a region of engagement with a filter.

In one embodiment, the snare engaging feature is radiopaque.

In another embodiment, the snare comprises a snaring hoop.

According to a further aspect the invention provides a method for the capture and removal of embolic material from a vasculature during an interventional procedure comprising the steps of:— providing a collapsible embolic protection filter having a collapsed configuration for delivery of the filter, and a deployed configuration;

advancing a guidewire through a vasculature;

crossing a desired treatment location with the guidewire;

deploying the filter distal to the treatment location;

carrying out an interventional procedure at the treatment location, embolic material generated during the treatment procedure being captured by the deployed filter;

advancing a snare;

engaging the snare with the filter; and withdrawing the snare and the filter.

In one case, the filter has a snare engaging feature and the snare is engaged with the snare engaging feature.

In another case, the snare engaging feature is provided on or by a support frame of the filter.

In one case, the method comprises the steps of leading the snare into engagement with the snare engaging feature of the filter and monitoring the engagement of the filter with the snare.

In one case, the snare and/or snare engaging features are radiopaque for external monitoring of the engagement.

In one case, the snare is engaged with the filter independent of the guidewire.

In another case, after crossing a treatment location with the guidewire the embolic protection device is introduced over the guidewire.

According to the invention, there is provided a method for the capture and removal of embolic material from a vasculature during an interventional procedure comprising the steps of:— advancing a guidewire through a vasculature;

crossing a desired treatment location with the guidewire;

introducing over the guidewire a collapsible embolic protection filter having a collapsed configuration for delivery and withdrawal of the filter, and a deployed configuration;

deploying the filter distal to the treatment location;

the filter in the deployed configuration being in apposition with the vasculature so that the filter is retained in position against substantial longitudinal movement, on deployment in the vasculature;

carrying out an interventional procedure at the treatment location, embolic material generated during the treatment procedure being captured by the deployed filter;

advancing a retrieval catheter;

collapsing the filter and retrieving the filter at least partially into the retrieval catheter and with it the captured embolic material; and withdrawing the retrieval catheter and the collapsed filter from the vasculature.

In one embodiment of the invention the method comprises the step of releasing the apposition of the filter with the vasculature before collapsing the filter.

The filter may be simultaneously collapsed and retrieved into the retrieval catheter by moving the retrieval catheter distally relative to the filter.

Alternatively the filter may be collapsed prior to retrieving the filter into the retrieval catheter. Preferably the method comprises the step of axially elongating the filter to collapse the filter.

Desirably the method comprises the step of engaging a part of the retrieval catheter with the filter to aid collapsing of the filter.

In one case the method comprises the steps of:—
  withdrawing the guidewire from the filter and the desired treatment location; and
  crossing the desired treatment location with another guidewire.

The interventional device may be introduced over the other guidewire for carrying out the interventional procedure.

In one case the interventional procedure comprises a stenting of the treatment location. In another case the interventional procedure comprises a balloon angioplasty procedure at the treatment location.

In another aspect the invention provides a method for the capture and removal of embolic material from a vasculature during an interventional procedure comprising the steps of:—
  advancing a guidewire through a vasculature;
  crossing a desired treatment location with the guidewire;
  introducing over the guidewire a collapsible embolic protection filter having a collapsed configuration for delivery and withdrawal of the filter, and a deployed configuration;
  deploying the filter distal to the treatment location;
  carrying out an interventional procedure at the treatment location, embolic material generated during the treatment procedure being captured by the deployed filter;
  advancing a retrieval catheter;
  fixing an abutment to the guidewire;
  engaging the guidewire abutment with the filter to prevent movement of the filter distally of the guidewire abutment;
  collapsing the filter and retrieving the filter into the retrieval catheter and with it the captured embolic material; and
  withdrawing the retrieval catheter and the collapsed filter from the vasculature.

The abutment may be fixed to the guidewire during deployment of the filter. Alternatively the abutment may be fixed to the guidewire before advancing the guidewire through the vasculature.

In a further aspect of the invention, there is provided a retrieval catheter for retrieving a medical device deployed in a vasculature, the catheter comprising:—
  an outer catheter body; and
  an inner coupling member having means for coupling to a medical device deployed in a vasculature;
  the catheter body being movable distally relative to the coupling member to retrieve a coupled medical device into the catheter body.

In one embodiment of the invention the coupling means comprises a male or female member on the coupling member for engagement with a corresponding female or male member on the medical device.

In a preferred case the male member is movable between a low-profile configuration and an outwardly protruding configuration. Ideally the male member is biased towards the outwardly protruding configuration. Most preferably the male member is of a resilient material.

In one case the coupling means is substantially arrowhead shaped.

In another case the male member is in the form of a hook for hooking around a female member on the medical device. Alternatively the male member may be in the form of a hook for hooking around a tether arm on the medical device. Ideally the tether arm is at a proximal end of the medical device. The tether arm may be located within the medical device.

In another embodiment of the invention the coupling means comprises at least one female member on the coupling member for engagement with at least one male member on the medical device. The female member may be in the form of a loop for looping around a protruding male member on the medical device.

In a preferred embodiment the coupling means comprises a pair of jaws on the coupling member, the jaws being movable between an outwardly protruding configuration and a low-profile configuration to grasp the medical device. The retrieval catheter may comprise an actuator to move the jaws to the outwardly protruding configuration. Ideally the actuator is movable longitudinally relative to the jaws to move the jaws in a camming arrangement to the outwardly protruding configuration. Most preferably the jaws are biased towards the low-profile configuration.

In another embodiment the catheter body is engageable with the jaws to move the jaws to the low-profile configuration. The jaws may be biased towards the outwardly protruding configuration.

In another embodiment of the invention the coupling means comprises an inflatable member on the coupling member for engagement with the medical device. Preferably the inflatable member is movable inwardly upon inflation to engage the medical device. The coupling means may comprise an engagement surface on the coupling member for engagement with an inflatable member on the medical device.

In a further embodiment the coupling member is at least partially of a magnetic material for magnetic coupling to an oppositely charged magnetic portion of the medical device.

The retrieval catheter may comprise means to axially elongate a deployed medical device to collapse the medical device to a low-profile configuration for retrieval into the catheter body. Preferably the elongation means comprises a second coupling member movable relative to the first coupling member to collapse the medical device. Ideally the second coupling member comprises a pusher member movable distally relative to first coupling member to engage a deployed medical device distally of the first coupling means and thereby collapse the medical device.

In one case the catheter body has a guidewire lumen extending partially therethrough for passing the catheter body over a guidewire in a rapid exchange manner. The guidewire lumen may be offset radially from the coupling member.

The retrieval catheter of the invention may be for retrieving an embolic protection filter deployed in a vasculature.

According to another aspect of the invention, there is provided a retrieval catheter for retrieving a medical device deployed in a vasculature, the catheter comprising:— a first coupling member having means for coupling to a medical device deployed in a vasculature; and a second coupling member having means for coupling to the deployed medical device;

the coupling members being relatively movable to axially elongate the medical device and collapse the medical device.

In one embodiment the catheter comprises an outer catheter body movable distally relative to the coupling members to retrieve a collapsed medical device into the catheter body.

In another aspect, the invention provides a method of retrieving a medical device from a vasculature, the method comprising the steps of:— advancing a retrieval catheter through a vasculature until a distal end of the retrieval catheter is proximally of the deployed medical device;

axially elongating an element of the medical device to collapse the medical device; and moving the retrieval catheter distally relative to the collapsed medical device to retrieve the medical device into the retrieval catheter.

In one embodiment the method comprises the steps of:— engaging a first coupling member with the element of the deployed medical device;

engaging a second coupling member with the element of the deployed medical device; and moving the coupling members relative to one another to axially elongate the element of the medical device.

The invention also provides in another aspect an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature in apposition with a vasculature wall;

in the outwardly extended configuration the filter exerting an outward radial force on a vasculature wall sufficient to retain the filter in position against substantial longitudinal movement.

In one embodiment of the invention the filter comprises a filter body and a filter support frame to support the filter body in the outwardly extended configuration in apposition with a vasculature wall, the filter support frame providing the outward radial force.

The filter may comprise a low-friction outer layer. Preferably the outer layer is of a hydrophilic material.

In one case the filter comprises an inflatable member to enhance the outward radial force.

Ideally the filter defines a guidewire lumen for passing the filter over a guidewire.

According to another aspect of the invention, there is provided an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter; and the filter comprising a central tether extending proximally of the filter.

Ideally the tether is a generally central tether.

The tether may comprise a wire, preferably the wire is configured to facilitate passage of a medical device over the wire.

The invention also provides in a further aspect, an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter; and the filter comprising an inflatable member to exert an outward radial force on a vasculature wall sufficient to retain the filter in position against substantial longitudinal movement.

In another aspect, the invention provides a method for the capture and removal of embolic material from a vasculature during an interventional procedure comprising the steps of:— advancing a first guidewire through a vasculature;

crossing a desired treatment location with the first guidewire;

introducing over the first guidewire a collapsible embolic protection filter having a collapsed configuration for delivery and withdrawal of the filter, and a deployed configuration;

deploying the filter distal to the treatment location;

withdrawing the first guidewire from the filter and the desired treatment location;

crossing the desired treatment location with a second guidewire;

introducing over the second guidewire an interventional device;

carrying out an interventional procedure at the treatment location, embolic material generated during the treatment procedure being captured by the deployed filter;

advancing a retrieval catheter;

collapsing the filter and retrieving the filter into the retrieval catheter and with it the captured embolic material; and withdrawing the retrieval catheter and the collapsed filter from the vasculature.

In one embodiment of the invention the method comprises the step of leading the second guidewire through the filter prior to carrying out the interventional procedure. The method may comprise the step of guiding the second guidewire through the filter. Ideally the second guidewire remains proximal of the deployed filter.

In another embodiment the method comprises the steps of:— withdrawing the second guidewire from the filter and the desired treatment location;

advancing a third guidewire to the filter; and advancing the retrieval catheter over the third guidewire.

In one case collapsing the filter into the retrieval catheter comprises the step of releasing the filter from apposition with the vasculature wall.

The diameters of the guidewires may differ. The material properties of the guidewires may differ.

The invention provides in a further aspect an embolic protection filter assembly for deployment in a vasculature, the assembly comprising:— a filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter; and a receiver to guide a docking device into association with the filter.

In one embodiment the filter has a guidewire lumen for passing the filter over a guidewire, and the receiver is configured to guide a guidewire into the guidewire lumen. The guidewire lumen may extend only partially through the filter.

Preferably the receiver is configured to guide a coupling member towards the filter for coupling to the filter.

In one case the receiver comprises a funnel. Preferably the funnel is movable between a collapsed configuration for movement through a vasculature, and an outwardly extended configuration for guiding a docking device. Ideally the funnel is biased towards the outwardly extended configuration.

In one embodiment the funnel comprises a funnel body and a funnel support to support the funnel body in the outwardly extended configuration. Preferably the funnel body comprises a membrane. Ideally the funnel support comprises a plurality of pivotable fingers.

In another embodiment the receiver comprises an approach channel. Preferably the channel is provided by a lumen in a catheter.

The receiver may be mounted to the filter. Preferably the receiver is detachably mounted to the filter.

Alternatively the receiver may be separate from the filter.

In a preferred embodiment the receiver has means to space the receiver from the wall of a vasculature. Ideally the spacing means comprises an inflatable member to engage the wall of a vasculature.

In one embodiment the receiver is at least partially provided by a wall of the filter. Preferably the receiver is at least partially provided by a wall of the filter at the inlet end of the filter. Alternatively the receiver may be at least partially provided by a wall of the filter at the outlet end of the filter.

In one case the receiver extends proximally of the inlet end of the filter. In another case the receiver is located distally of the inlet end of the filter.

In a further embodiment the receiver is radially offset from the longitudinal axis of the filter.

According to a further aspect of the invention, there is provided an embolic protection system comprising:— an embolic protection filter assembly of the invention; and a docking device which may be guided by the receiver into association with the filter.

In one embodiment the docking device comprises a guidewire.

In another case the docking device comprises a coupling member.

In another aspect, the invention provides an embolic protection filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter having a guidewire aperture for passing the filter over a guidewire; and the filter comprising a seal to seal the guidewire aperture.

The seal may be self-closing.

Ideally the seal is located at a proximal end of the filter, and/or at a distal end of the filter.

The filter may have a tubular member extending from the guidewire aperture to define a guidewire lumen through the tubular member. In one case the tubular member extends through at least part of the filter. Preferably the tubular member is radially offset from the longitudinal axis of the filter.

In one embodiment the seal is an annular member around the guidewire aperture, the annular member being closable down to seal the guidewire aperture. In one case the annular member is a tube. In another case the annular member comprises a soft membrane. The annular member may comprise two or more circumferentially overlapping flaps.

The invention provides in another aspect an embolic protection filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter;

the filter being movable between a collapsed configuration for movement through a vasculature, and an outwardly extended configuration for deployment in a vasculature;

the filter at least in the collapsed configuration having a guidewire lumen defined at least partially therethrough for passing the filter over a guidewire.

The guidewire lumen may be defined by a tubular member extending at least partially through the filter.

In one case the tubular member is mounted to the filter. In another case the tubular member is spaced proximally of a distal end of the filter.

Preferably the tubular member is shortenable upon movement of the filter from the collapsed configuration to the extended configuration. Ideally the tubular member comprises at least two telescopable tubes.

In one embodiment the tubular member is provided by a catheter.

The catheter may be a retrieval catheter, or a delivery catheter.

In another embodiment of the invention the filter comprises a support structure, in the collapsed configuration the support structure forming a tubular member to define the guidewire lumen.

BRIEF DESCRIPTION OF DRAWINGS

The invention will be more clearly understood from the following description of some embodiments thereof, given by way of example only, with reference to the accompanying drawings, in which:—

FIGS. 32 to 39 are various views of a delivery catheter which may be used in the invention;

FIGS. 40 to 54 are side, partially cross sectional views illustrating various steps in the method of the invention;

FIGS. 55 to 57 are various views of another delivery catheter which may be used in the invention;

FIG. 115 is a perspective view of another embolic protection filter according to the invention;

FIGS. 116 and 117 are perspective and cross-sectional, side views respectively of another embolic protection filter according to the invention;

FIG. 118 is a perspective view of a further embolic protection filter according to the invention guiding a guidewire through the embolic protection filter;

FIGS. 201 to 206 are various views illustrating snaring of another filter;

FIGS. 213 to 218 are views illustrating another retrieval system;

FIGS. 225 and 226 are views of another filter of the invention;

FIGS. 227 to 230 illustrate retrieval of filters;

FIG. 229A is a cross-sectional view illustrating the retrieval of the filter of FIG. 230 using the retrieval catheter of FIG. 229.

FIGS. 231 and 232 illustrate snaring of another filter;

FIG. 240 is a partially cross-sectional, side view of an embolic protection filter according to the invention in an expanded configuration;

FIG. 241 is a partially cross-sectional, side view of the filter of FIG. 240 in a collapsed configuration;

FIG. 244 is a partially cross-sectional, side view of the filter of FIG. 240 after being recrossed with a guidewire;

FIGS. 245 and 246 are partially cross-sectional, side views illustrating retrieval of the filter of FIG. 244.

FIGS. 247 to 251 are views similar to FIGS. 240, 241, and 244 to 246 respectively of another embolic protection filter according to the invention;

DETAILED DESCRIPTION

The invention provides an embolic protection system which has a number of features which allows the system to be used in placing a guide catheter proximal to lesion as per standard practice and advance any suitable guidewire across the lesion. A load filter is loaded into the delivery catheter in such a way as to provide a lumen through the loaded device through which the guidewire will pass. The loaded device is advanced over the guidewire and across the lesion. The filter is deployed from the delivery catheter and the delivery catheter is removed. The filter remains stable in the vessel without any user control. Standard interventional procedures (angioplasty, stent etc. . . . ) can be performed. The guidewire may be replaced by simply removing the initial wire and advancing a replacement wire through the guide catheter, across the lesion and through the filter. The filter may be retrieved by advancing a retrieval catheter over the guidewire and up to the filter. An inner member of the retrieval catheter may be engaged with the filter. Then outer retrieval sheath is advanced to collapse the filter and retrieve. The guidewire may be left in place if desired.

Figure 1:
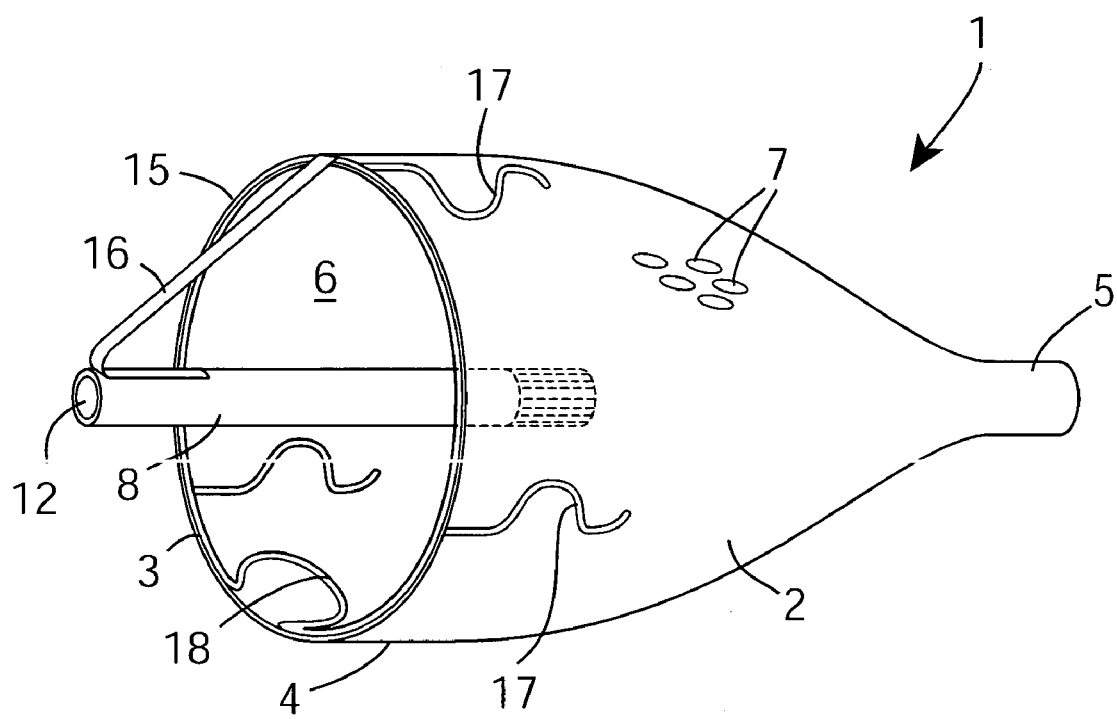
FIG. 1 is a perspective of an embolic protection filter according to the invention.
Figure 2:
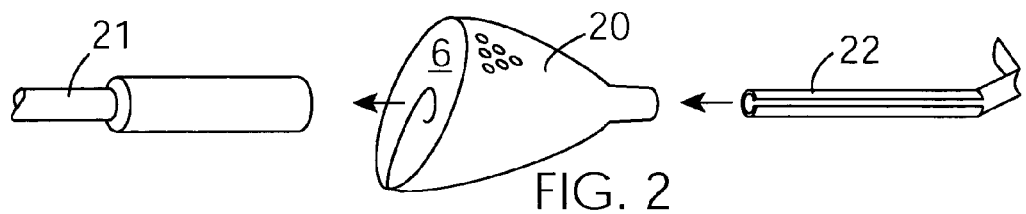
FIGS. 2 to 16 are partially cross-sectional, side views illustrating the use of an embolic protection filter.

Referring to the drawings and initially to FIG. 1 there is illustrated an embolic protection filter 1 according to the invention, the filter 1 being suitable for deployment in a vasculature to filter undesired embolic material from the blood stream flowing through the vasculature.

The filter 1 comprises a collapsible filter body 2 which in this case is supported by a collapsible filter support frame 3. In this case the filter support is mounted on an inner tube 8.

The filter body 2 has an inlet end 4 and an outlet end 5. The inlet end 4 has one or more, and in this a single, large inlet opening 6 which are sized to allow blood and embolic material enter the filter body 2. The outlet end 5 has a plurality of small outlet openings 7 which are sized to allow through passage of blood but to retain undesired embolic material within the filter body 2. In this way, the filter 1 captures and safely retains any undesired embolic material in the blood stream within the filter body 2 while facilitating continued flow of blood through the vascular system. Emboli are thus prevented from flowing further downstream through the vascular system, which could otherwise have potentially catastrophic results.

The relatively large inlet opening 6 provides for the possibility of aspirating embolic material from within the filter body 2. This may be particularly advantageous if it is desired to leave the filter 1 in place in a vasculature for a long period of time, for example overnight, to assist in vascular recovery.

The filter body 2 may have a low-friction outer layer, for example a hydrophilic coating, to minimise frictional resistance during deployment and retrieval of the filter 1, and the filter body 2 may be of an oriented polymeric material, as described in International patent application No. PCT/IE01/00087, the relevant contents of which are incorporated herein by reference.

The inner tube 8 has a guidewire lumen 12 therethrough for passing the filter 1 over a guidewire 10 (FIGS. 2 to 16). A guidewire 10 can pass through the filter, however, in the deployed configuration the filter is independent of the guidewire. Thus, the guidewire can be moved independently of the filter without any associated movement of the filter. The arrangement allows relatively large radial forces to be exerted on the vascular wall without the risk of abrasion causes by movement of the deployed filter. In this way damage to the endothelium can be avoided.

The filter 1 is movable between a low-profile, collapsed configuration for movement through the vasculature, and an outwardly extended configuration for deployment in the vasculature in apposition with the vasculature wall.

In the outwardly extended configuration, the filter body 2 is supported in an expanded position by the filter support 3 so as to maximise the internal volume of the filter body 2 to capture and safely retain as much embolic material as possible.

The filter support 3 supports the filter body 2 in the outwardly extended configuration in apposition with the vasculature wall to prevent blood flow bypassing the filter 1 between the filter body 2 and the vasculature wall.

The support frame in this case defines a proximal support hoop 15 which is connected to the tubular member 8 by a support arm 16. The support 3 in this case also comprises a number of axially extending portions 17 which assist in providing body support to the filter in a vessel and assist in preventing rotation of the filter when deployed in the deployed configuration. The support may be of wire and may also comprise one or more stabilising hoops(s) 18.

In this case the tubular member 8 terminates proximally of the distal end 5 of the filter. This has a number of advantages. It facilitates recrossing of the filter 1 with a guidewire and the distal free end of the tubular member 8 may be readily snared for snaring and/or retrieval of the filter when it is desired to remove the filter from the vasculature.

In the outwardly extended configuration, the filter support 3 exerts an outward radial force on the filter body 2 and the vasculature wall which results in a frictional force between the filter body 2 and the vasculature wall sufficient to retain the filter 1 in position against substantial longitudinal movement.

In the invention the filter will not rotate or collapse in the absence of guidewire support. Conventional filters are coupled (directly or indirectly) to a wire—this wire enhances the stability of the filter. This invention describes a filter which will remain fully open and opposed to the vessel wall in the absence of any support from a guidewire. This is achieved by using a support frame which does not allow rotation in the vessel lumen. In general, a frame which lies in only one plane cannot remain apposed to the vessel wall without support from the guidewire. The design of the system is such that the filter must do considerable work to move longitudinally.

In order to ensure that the filter is retained in position the filter apposition force generates a frictional force between the filter and the vessel. The frictional force generated by the filter is dependent on the contact area, the apposition force generated by the filter and the coefficient of static friction between the filter and the vessel. Locating the filter using frictional forces alone is a worst-case analysis as it does not include the effect of tapered vessels. These will increase the apposition force generated by the filter as it moves distally into a lumen of decreasing diameter.

The radial apposition force of the filter support 3 is sufficient to retain the deployed filter 1 in position in the vasculature against substantial longitudinal movement, even if the guidewire, over which the filter 1 is delivered, is moved. No stop, abutment or other stop means is required on the guidewire to prevent the filter 1 from migrating downstream in the vasculature. In this manner, the invention enables an interventional procedure to be performed using a standard guidewire. This enhances clinician freedom by enabling a clinician to choose the most appropriate medical guidewire for a particular interventional procedure, and/or a particular patient anatomy.

In the case of a filter which has an integral tubular member the tubular member defines a lumen through which a guidewire can pass. In the invention such a guidewire passageway may be provided by a component of the delivery system such as a portion of a deployment pusher. Alternatively, the tubular member may be a separate component which is removed after the guidewire has passed through the filter. Thus, the member defining a guidewire pathway through the filter may be a movable or removable component.

Referring to FIGS. 2 to 16 there are illustrated various steps in the use of an embolic protection device during an interventional procedure. Various steps in the method will be described and it will be appreciated that the various steps and the features of the various apparatus used in the method may be used independently of one another, for example in the methods and apparatus of other aspects of the invention.

Figure 3:
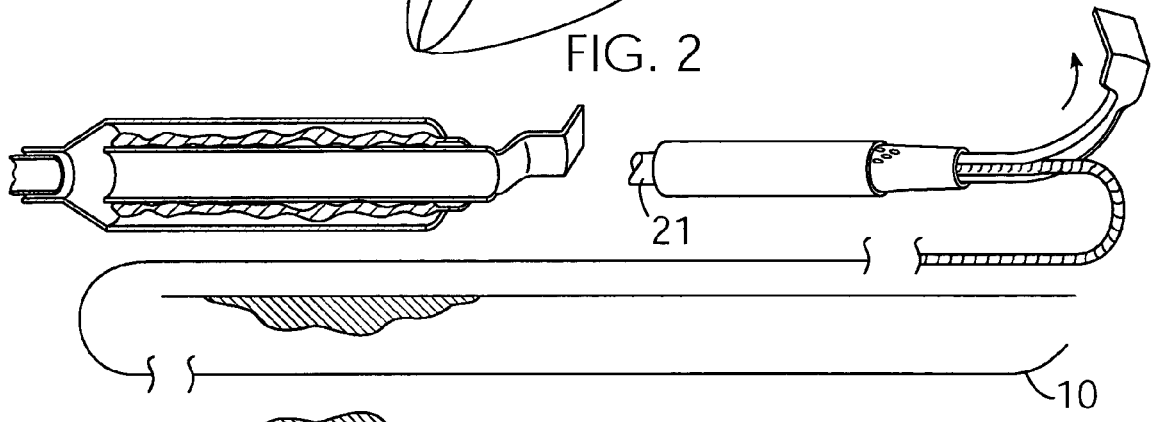
Figure 4:
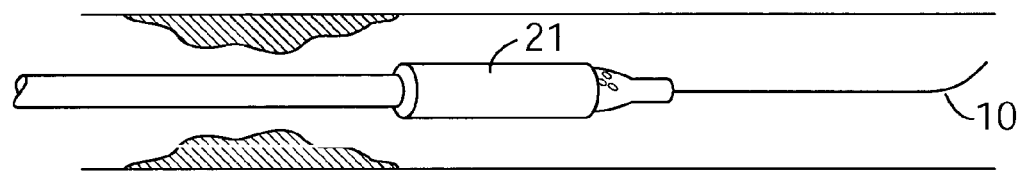
Figure 5:
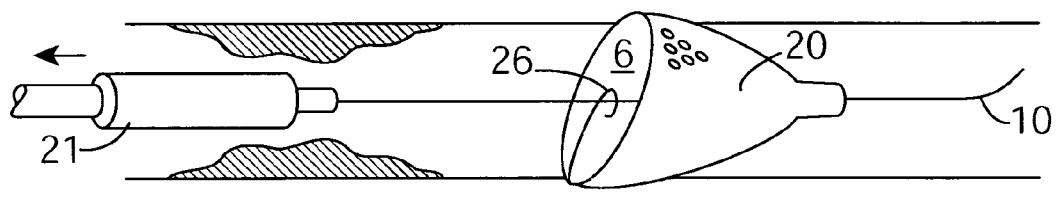
Figure 6:
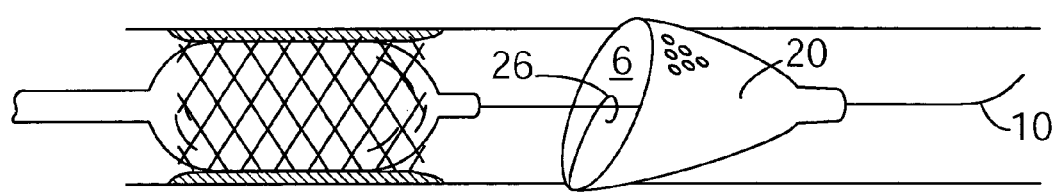
Figure 7:
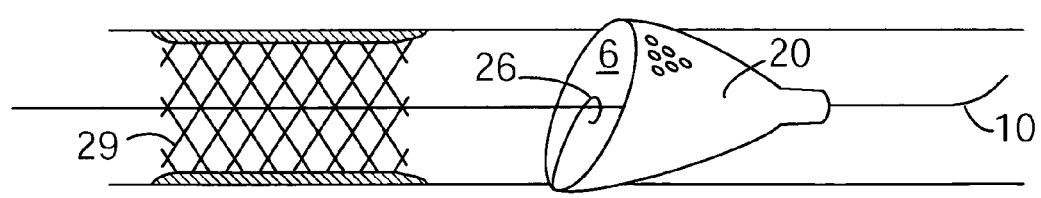
Figure 8:
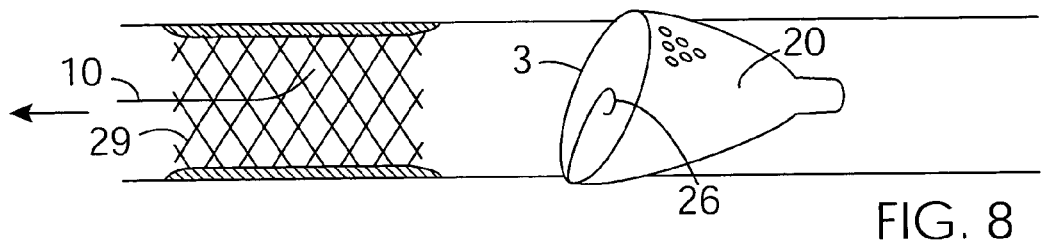

The filter does not necessarily itself have a predetermined lumen for passage of a guidewire. At various stages a lumen is defined when such a lumen is required. On loading of a filter 20 into a delivery catheter 21 a guidewire lumen is defined (FIG. 2) which is used for delivery of the filter 20 over a pre-positioned guidewire 10 (FIG. 3). The lumen-defining member 22 may be removed (FIG. 3) and the filter is advanced to and deployed distal to a treatment location in the vasculature (FIGS. 4 and 5). Various procedures may be carried out such as balloon angioplasty and stenting with a stent 29 (FIGS. 6 and 7). The filter may be retrieved into a retrieval catheter 25 (FIGS. 11 to 15) and the filter removed.

In this case the filter 20 comprises a filter body supported in the deployed configuration by a support frame defining a large proximal opening 6 and having a snaring engaging element in the form of a hook 26. In use, the filter is loaded into a delivery catheter 21 by inserting a tubular element 22 through the filter. The delivery catheter may be threaded onto a pre-deployed bare guidewire 10, the tubular element 22 guiding the guidewire 10 through the filter 20 at the distal end of the delivery catheter 21. Once the guidewire 10 has entered the delivery catheter 21 proximal to the filter 20 the tubular element 22 may be removed. To facilitate this, the tubular element may be of C-shape in transverse cross section. The delivery catheter 21 is then advanced over the guidewire 10 to a location which is distal of a treatment site. The filter 20 is deployed by pushing it out from the distal end of the delivery catheter, for example by using a pusher. The filter is then in the deployed open configuration distal to a treatment location (FIG. 5). Various procedures may be carried out at the treatment location, and embolic material released during the treatment procedures being captured in the filter. The treatment procedures may include deployment of a stent 29 from a stent delivery catheter threaded over the guidewire 10. When it is desired to retrieve the filter a retrieval catheter 25 is delivered over the guidewire 10. The retrieval catheter 25 may be a snare catheter or a separate snare catheter may be delivered through the retrieval catheter. The snare may comprise a lasso 30 or the like which engages the snaring hook 26 of the filter support frame. The guidewire 10 may then be withdrawn or left in place.

Figure 9:
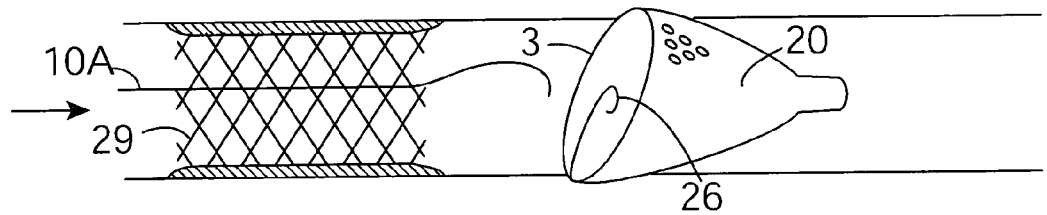
Figure 10:
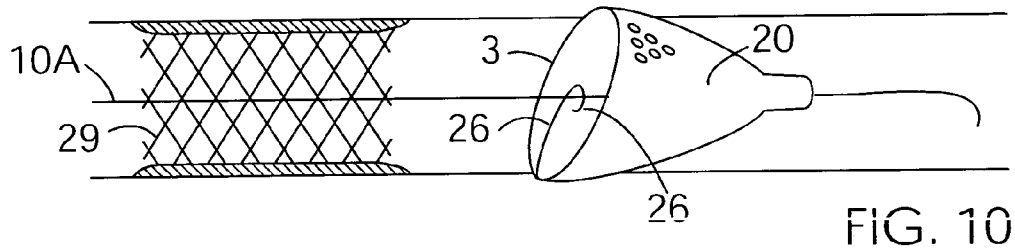
Figure 11:
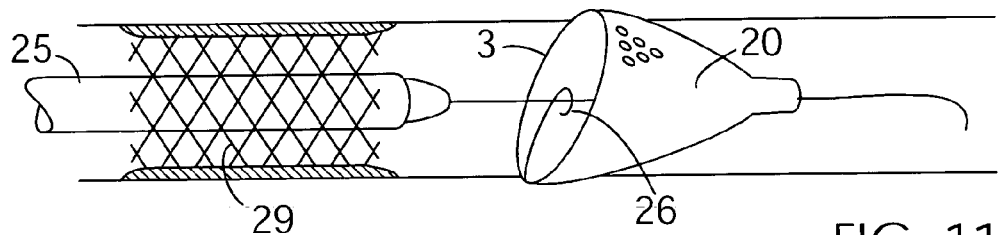
Figure 12:
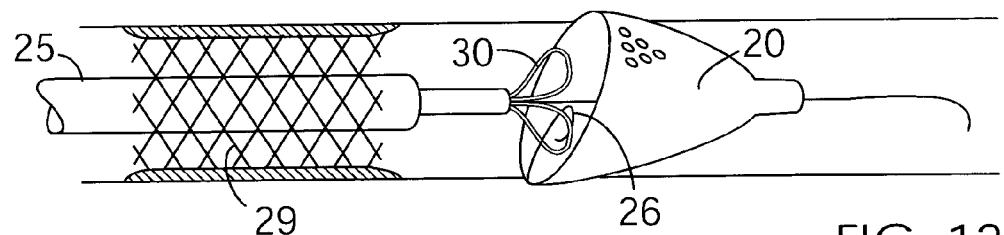
Figure 13:
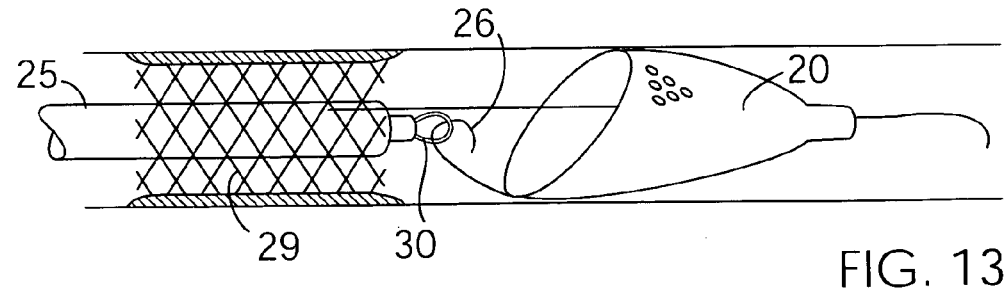
Figure 14:
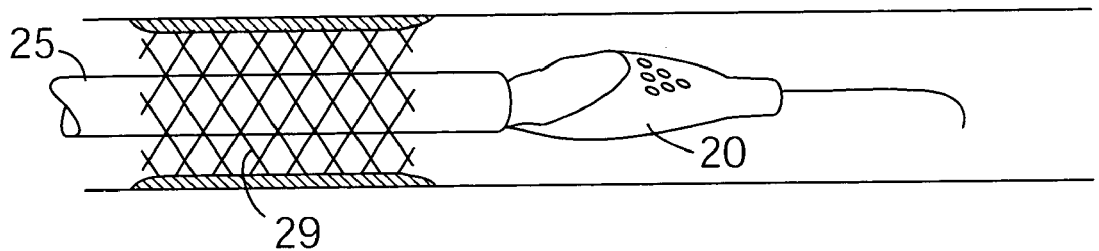
Figure 15:
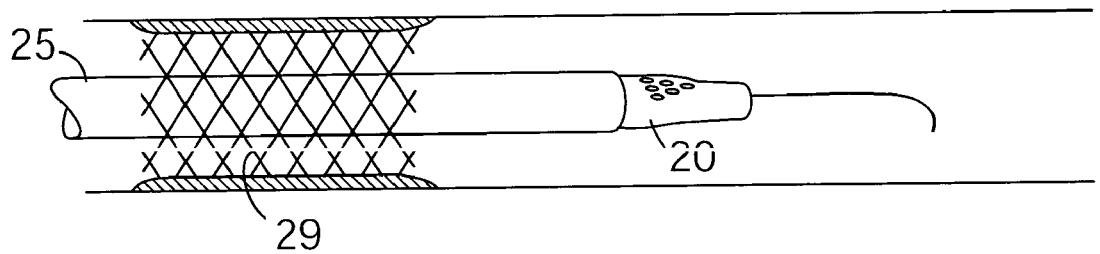
Figure 16:
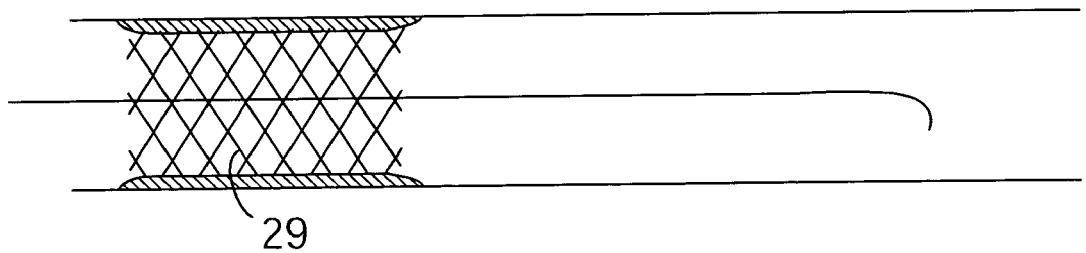

In certain circumstances the guidewire 10 could be retracted, or even removed completely (FIG. 8), without disturbing the position of the deployed filter in the vasculature. Another guidewire 10A may be advanced through the filter (FIGS. 9 and 10). This may be particularly advantageous in the case of certain interventional procedures, for example in coronary applications as will be described in more detail below.

The support may be configured to distribute the outward radial force over a relatively large area of the vasculature wall to minimise local stress distributions.

Many different designs of filter may be used such that on deployment, the filter applies a local radial force to the vasculature to substantially prevent movement of the filter relative to the vasculature in the deployed configuration. In the deployed configuration the filter is anchored to the vasculature. In some cases the filter comprises a filter body and a filter support frame to support the filter in the deployed configuration. The support frame and/or the filter body may comprise the anchor. The anchor may comprise a plurality of anchor elements which may be spaced-apart circumferentially around the filter when the filter is in the deployed configuration.

Figure 17:
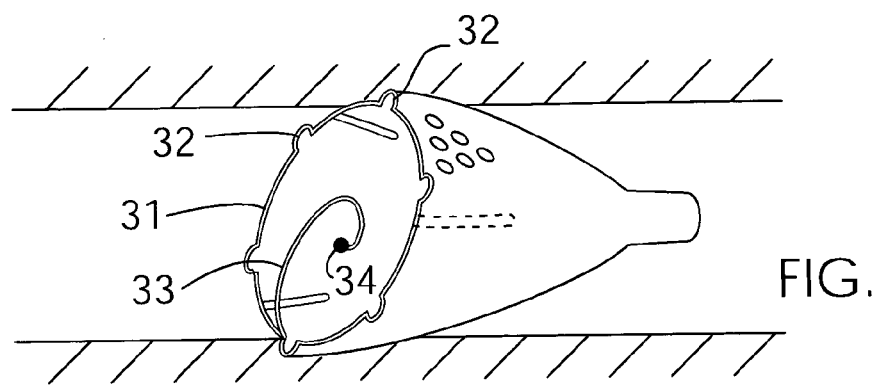
FIG. 17 is a perspective view of another filter of the invention.

Referring to FIG. 17 the filter frame includes a proximal support hoop 31 with radially projecting vessel indentors or stabilisers 32 to prevent longitudinal movement of the filter in the vessel. The frame may include a snaring feature 33 which may have a radiopaque marker 34.

Figure 18:
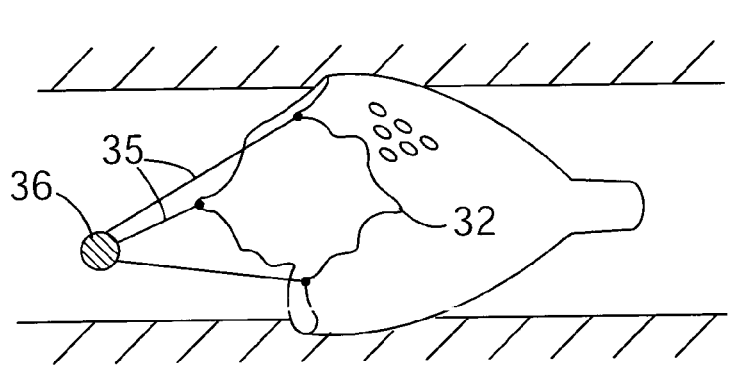
FIG. 18 is a side view of a further filter of the invention.
Figure 19:
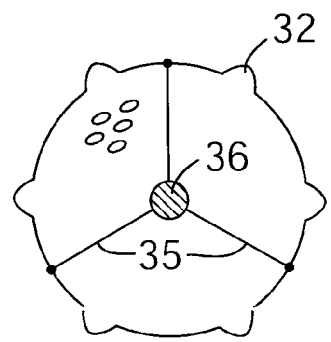
FIG. 19 is an end view of the filter of FIG. 18.

Referring to FIGS. 18 and 19 the vessel indentors or stabilisers 32 may also provide convenient attachment locations for attachment of tethers 35. The tethers 35 may be interconnected at the proximal end by a connector 36 which may be radiopaque for ease of location to snare the filter for retrieval.

Figure 20:
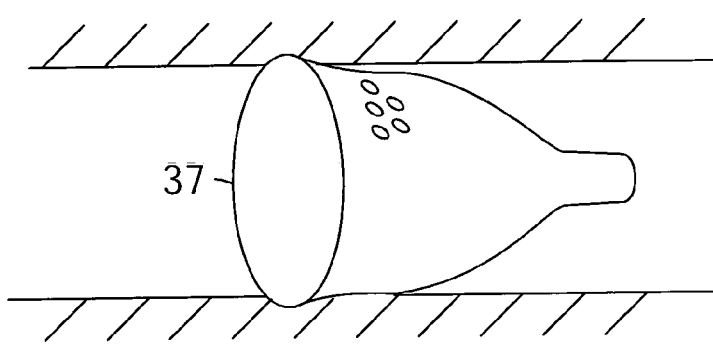
FIG. 20 is a side view of another filter of the invention.

Referring to FIG. 20 the filter may have an enlarged lip 37 at the proximal end for engagement in a vessel to anchor the filter in a desired position.

Figure 22:
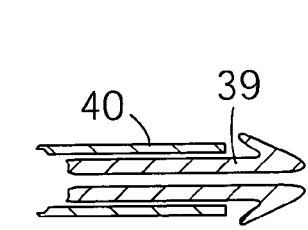
FIGS. 21 and 22 are side views of another filter, in use.
Figure 21:
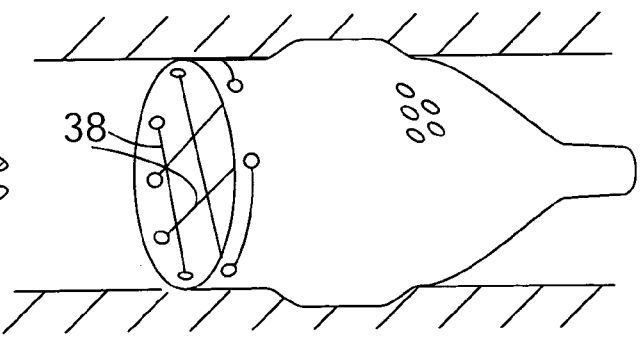
Figure 23:
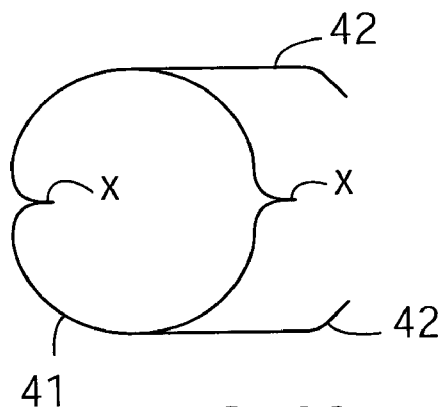
FIGS. 23 to 26 are diagrams illustrating a filter of the invention, in use.

Referring to FIGS. 21 and 22 there is illustrated another filter which is apposed in a vessel. The filter has a retrieval mechanism somewhat like a closed drawstring arrangement with a mesh-like structure 38, when deployed, which may be engaged by the distal tip 39 of a centering catheter (or any suitable snare) for collapsing the filter and drawing it into a retrieval catheter 40.

Figure 24:
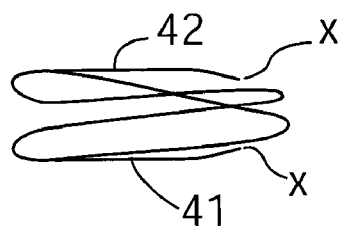
Figure 25:
Figure 26:
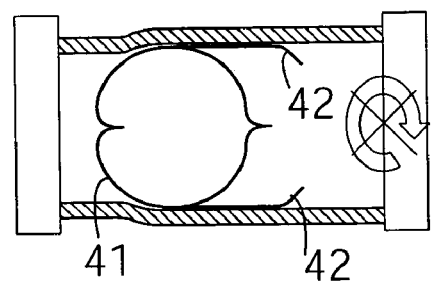

Another filter frame is illustrated in FIGS. 23 to 26. The frame has a proximal hoop 41 and distally projecting arms 42. X denotes terminations of the bifilar type to facilitate wrap-down of the filter as illustrated in FIGS. 24 and 25. Thus, the parking space occupied by the filter is optimised. In the deployed configuration in a vessel as schematically illustrated in FIG. 26 the filter apposes the vessel wall and rotation and translation of the filter in relation to the vasculature is prevented.

Figure 27:
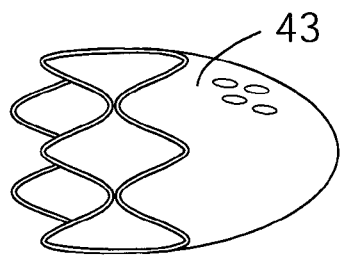
FIGS. 27 to 31A are perspective views of various alternative constructions of filters.
Figure 28:
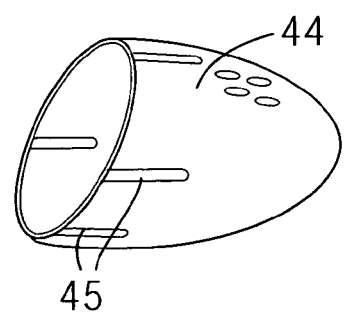
Figure 29:
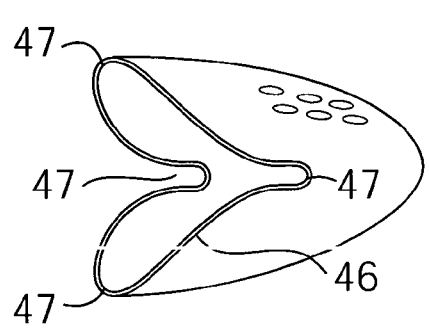

In general, the filter applies sufficient radial force to remain stable in a vessel when in the deployed configuration. In addition, the filter remains correctly orientated even without a guidewire in place. Some filters of this type are illustrated in FIGS. 27 to 31. In FIG. 27 the filter 43 has body support. In FIG. 28 the filter 44 has stabilising arms 45. The filter of FIG. 29 is in the form of a hoop 46 with a number of inflection points 47. There may be four or more such inflection points as illustrated.

Figure 30:
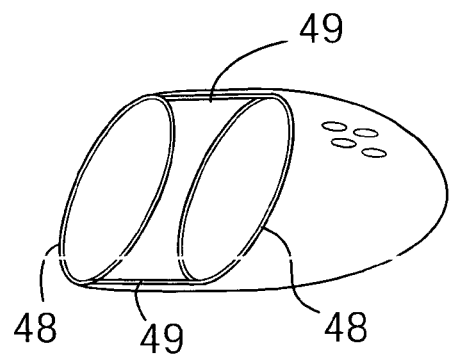

In FIG. 30 the filter has two axially spaced-apart support hoops 48 which are interconnected by connecting arms 49. The filter of FIG. 31 has two offset hoops 50. Any of these filters may be connected to a central tubular member by a rigid member(s) and/or by a tether(s). Many more arrangements with support in more than one place are envisaged.

Figure 31A:
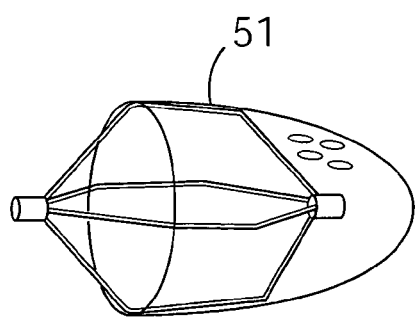
Figure 31:
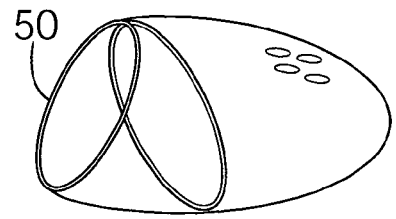
Figure 32:
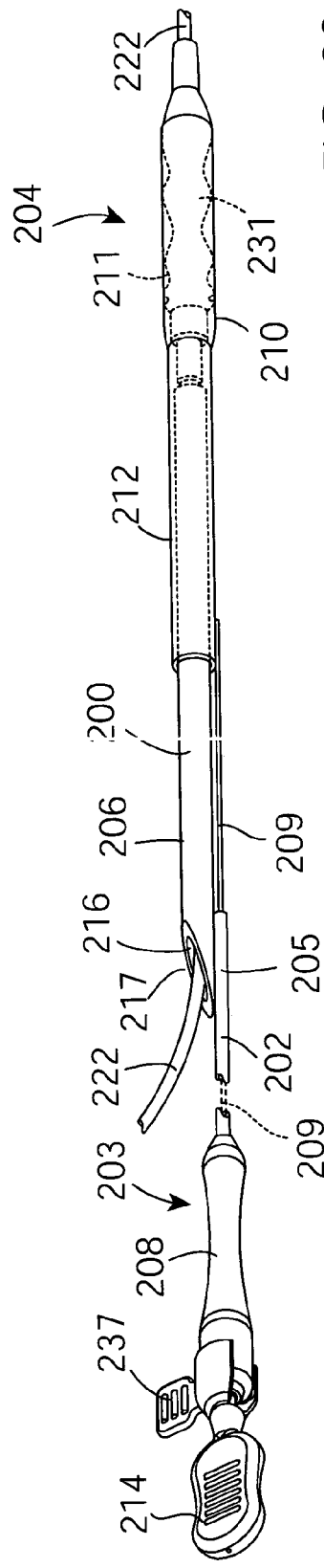
Figure 33:
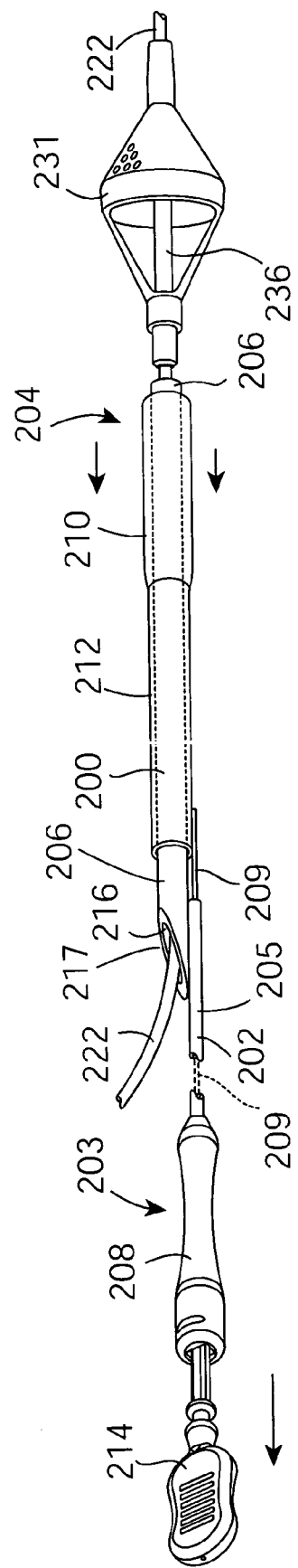

The filter 51 of FIG. 31A has body support provided by a nitinol tube or wire.

Figure 242:
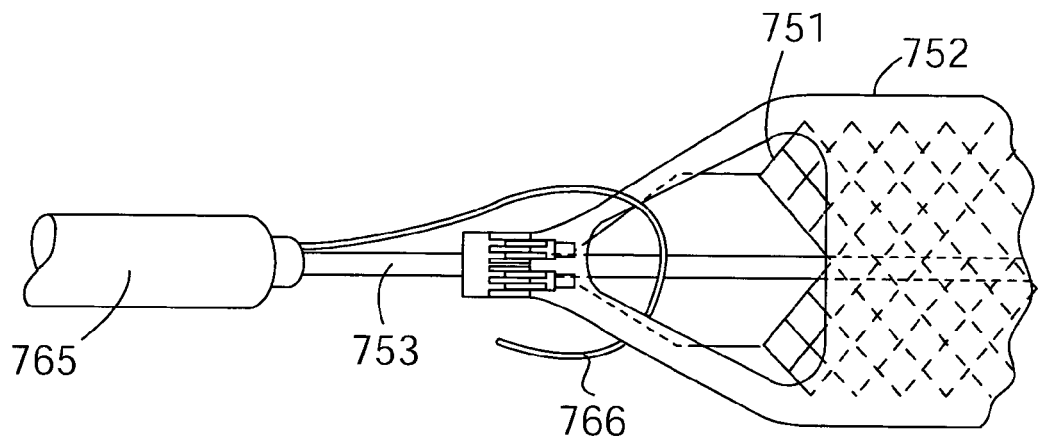
FIGS. 242 and 243 are partially cross-sectional, side views illustrating retrieval of the filter of FIG. 240.
Figure 243:
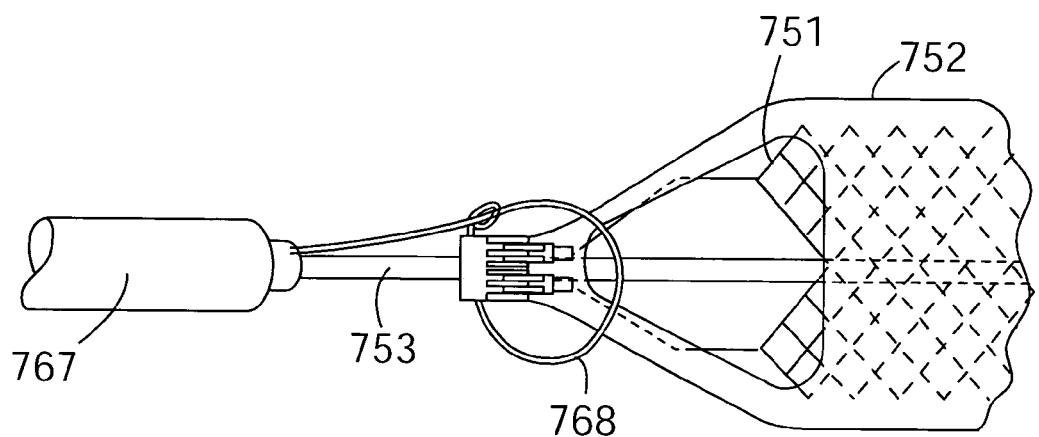

To retrieve the filter, any suitable means, such as the hooked retrieval catheter (FIG. 250), or the looped retrieval catheter (FIG. 251) may be used, in a manner similar to that described with reference to FIGS. 242 and 243.

Referring to FIGS. 32 to 39 there is illustrated a delivery catheter 200 which may be used with a filter of the invention. This catheter is described in detail in our co-pending U.S. Ser. No. 10/180,980, the relevant contents of which are incorporated herein by reference. The delivery catheter 200 comprises a catheter body 202 which extends between a proximal end 203 and a distal end 204, a restraining sheath 210 at the distal end 204 of the catheter body 202, and an elongate actuator, which is provided in this case in the form of a stainless steel wire 209.

Figure 34:
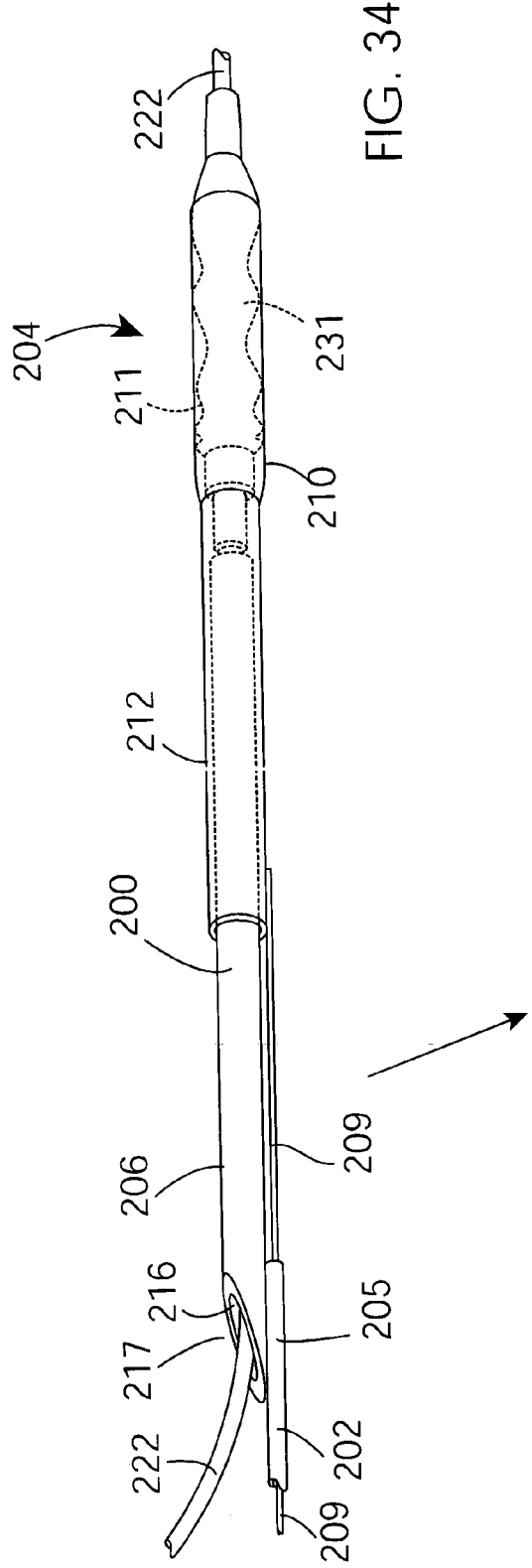
Figure 35:
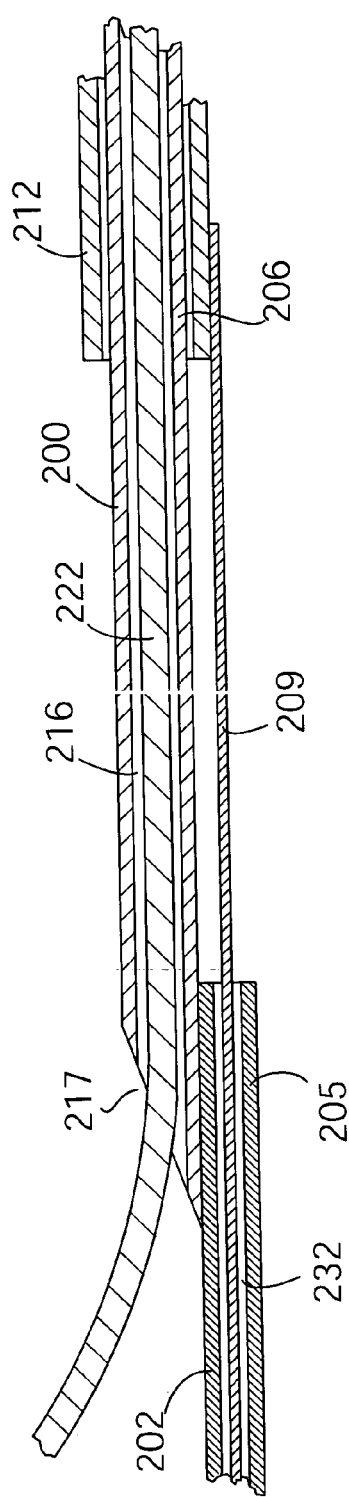

The catheter body 202 comprises a proximal hypotube portion 205 and a radially offset distal spring pusher 206. As illustrated in FIGS. 34 and 35, the pusher 206 is fixedly attached to the hypotube 205 in a side-by-side overlapping arrangement with the proximal end of the pusher 206 located proximally of the distal end of the hypotube 205.

The pusher 206 has a guidewire lumen 216 extending through the pusher 206 with an opening 217 at the proximal end of the lumen 216 for passage of a guidewire 222 through the lumen 216 and out through the proximal guidewire opening 217 (FIG. 35). The delivery catheter 200 is thus configured to be passed over the guidewire 222 in a rapid-exchange manner.

The pusher 206 tapers proximally inwardly at the opening 217 for a smooth crossing profile.

When assembled, the hypotube 205 and the pusher 206 are located substantially side-by-side. This side-by-side assembly of the hypotube 205 relative to the pusher 206 enables the guidewire 222 to exit through the proximal guidewire opening 217 smoothly and substantially parallel to the longitudinal axis of the catheter 200. In particular, the passage of the guidewire 222 through the proximal guidewire opening 217 does not increase the overall profile of the catheter 200.

A connector shaft 212 is fixed to the sheath 210 with the shaft 212 extending proximally over the pusher 206 towards the distal end of the hypotube 205. The proximal end of the sheath 210 overlaps the distal end of the shaft 212, and a marker band 213 is located at the distal end of the shaft 212 between the shaft 212 and the sheath 210.

The actuator wire 209 extends distally through an actuator lumen 232 in the hypotube 205, out of the actuator lumen 232 at the distal end of the hypotube 205, externally along the pusher 206 to the proximal end of the shaft 212. The wire 209 is attached to the exterior surface of the shaft 212, for example by bonding. By attaching the wire 209 to the exterior of the shaft 212, this arrangement provides for more space within the pusher lumen 216 for guidewire passage. In addition, attachment of the actuator wire 209 to the exterior of the shaft 212 is an easier step to achieve from a manufacturing viewpoint than attachment to the interior of the relatively long shaft 212.

The restraining sheath 210 and the connector shaft 212 are movable in a sliding manner relative to the catheter body 202. When the sheath 210 extends distally of a distal end of the spring pusher 206, the sheath 210 defines an internal reception space 211, as illustrated in FIGS. 36 to 38. A collapsed embolic protection filter 231 may be received within the reception space 211, where the filter 231 will be restrained by the sheath 210 in a low-profile configuration during delivery to a desired site in a vasculature. A suitable material for the sheath 210 is polyethyleneterephthalate (PET).

The distal end of the shaft 212 is flared outwardly at 237 (FIG. 38). During delivery of the filter 231, the distal end of the pusher 206 is spaced proximally of the distal end of the shaft 212, and the proximal end of an inner tubular member 236 of the filter is partially inserted into the flared shaft 212. This arrangement provides a bridge in stiffness between the relatively stiff shaft 212 and the relatively stiff inner tubular member 236 of the filter 231. Thus the possibility of buckling of the relatively flexible sheath 10 is minimised. The distal end of the pusher 206 is engagable with the inner tubular member 236 of the filter 231 upon retraction of the sheath 210 to deploy the filter 231 out of the reception space 211.

Figure 39:
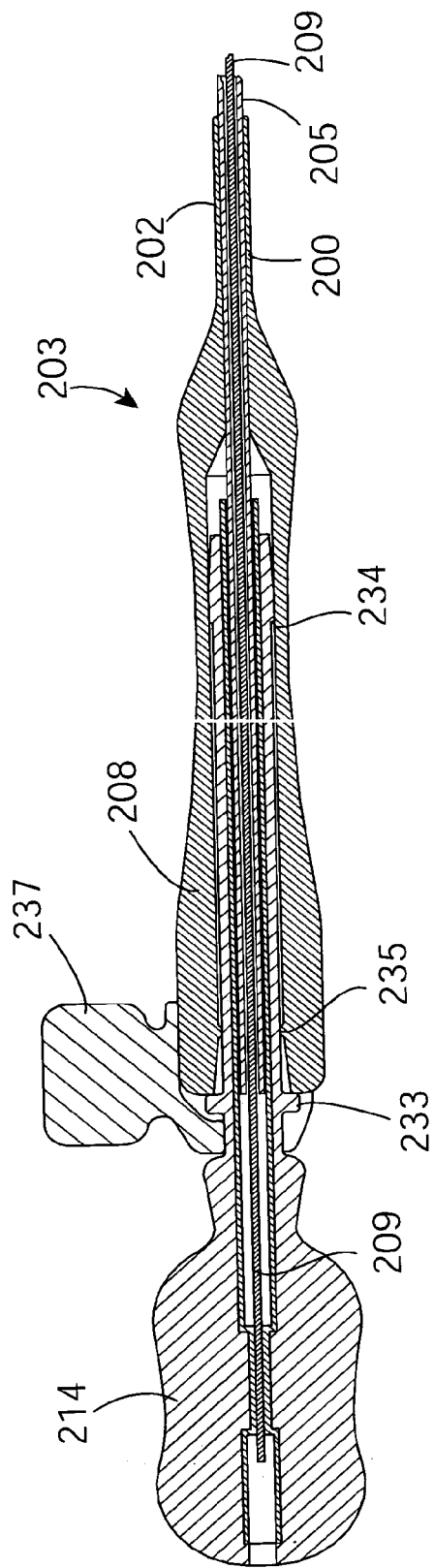

As illustrated in FIG. 39, at the proximal end 203 of the catheter 200 a distal handle 208 is provided for gripping the catheter body 202 and a proximal handle 214 is provided for gripping the actuator wire 209. The distal handle 208 is injection moulded over the hypotube 205 and the proximal handle 214 is crimped to the proximal end of the wire 209.

The handles 208, 214 are movable relative to one another in a telescoping manner with the proximal handle 214 sliding within the distal handle 208. Movement of the handles 208, 214 is limited by means of stop means. Abutment of an outward annular protrusion 233 on the proximal handle 214 against the proximal end of the distal handle 208 prevents further movement of the proximal handle 214 distally relative to the distal handle 208. Engagement of a shoulder 234 on the proximal handle 214 with an inward annular protrusion 235 on the distal handle 208 prevents further movement of the proximal handle 214 proximally relative to the distal handle 208. A releasable safety clip 237 is provided to maintain the handles 208, 214 fixed relative to one another.

When the catheter 200 is assembled the sheath 10 is directly connected to the proximal handle 214, and the pusher 206 is directly connected to the distal handle 208. Movement of the proximal handle 214 proximally relative to the distal handle 208 moves the wire 209, the connector shaft 212 and the sheath 210 proximally relative to the pusher 206 to facilitate deployment of the filter 231 from within the reception space 211.

The delivery catheter 200 may be used to deliver the embolic protection filter 231 through a vasculature and to deploy the embolic protection filter 231 downstream of a stenosed region in the vasculature to prevent potentially harmful emboli, which may be released into the blood stream during treatment of the stenosis, such as by a stenting procedure, from migrating further through the vascular system.

Referring to FIGS. 40 to 54 the use of the delivery catheter 200 will now be described in relation to a filter 301 of the invention which has tubular member 306 with a distal end that is spaced proximally from the distal end of the filter. Such as arrangement facilitates removal replacement of a guidewire and can also be readily snared and retrieved as described herein.

In use, a loading device 310 is partially inserted into the reception space 211 of the sheath 210. A pushing device 311 is then threaded through the tubular member 306 of the filter 301 and extended into the reception space 211, as illustrated in FIG. 40.

By moving the pushing device 311 proximally, an engagement stop 312 on the pushing device 311 engages the distal end of the tubular member 306 and the filter 301 is moved towards the loading device 310 (FIG. 410). Continued proximal movement of the pushing device 311 pushes the filter 301 through the loading device 310, thereby collapsing the filter 301, and pushing it into the reception space 211 (FIG. 41).

The catheter 200 with the collapsed filter 301 received within the reception space 211 are then moved together proximally away from the loading device 310 (FIG. 42).

The method of collapsing the filter 301 and loading the filter 301 into the reception space 211 is similar to that described in International patent application number PCT/IE01/00052, the relevant contents of which are incorporated herein by reference.

Figure 44:
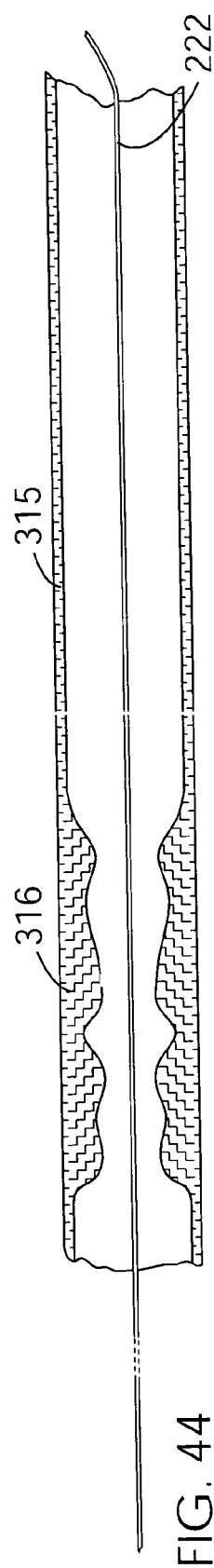
Figure 45:
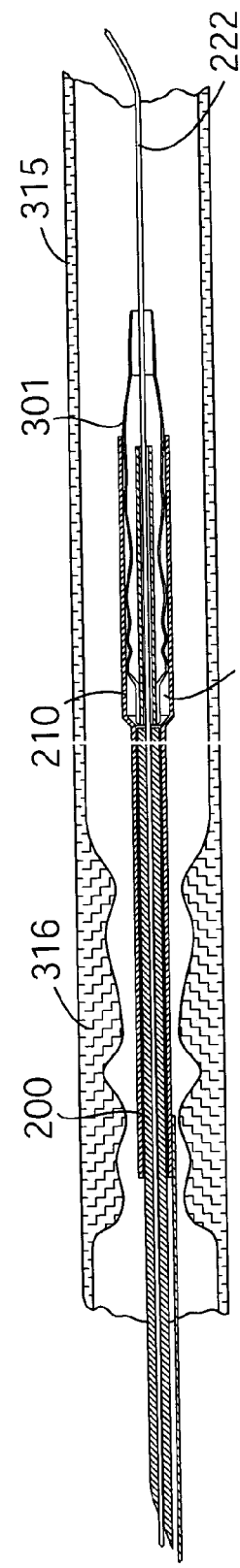
Figure 46:
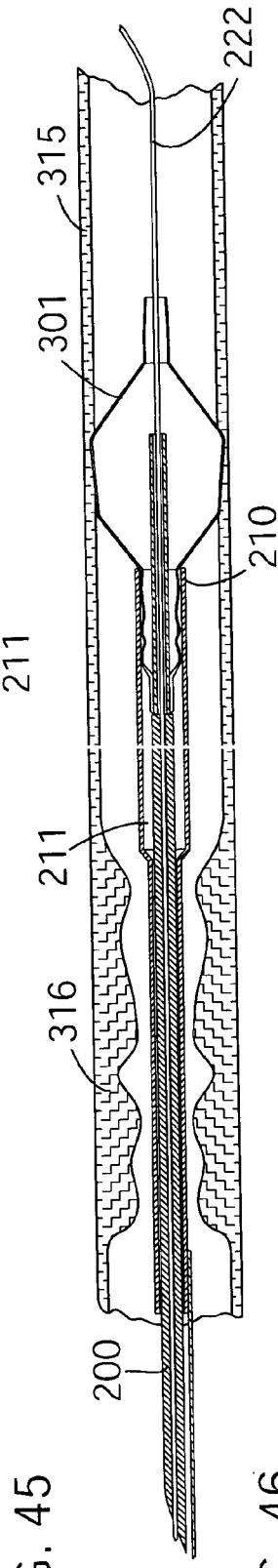
Figure 47:
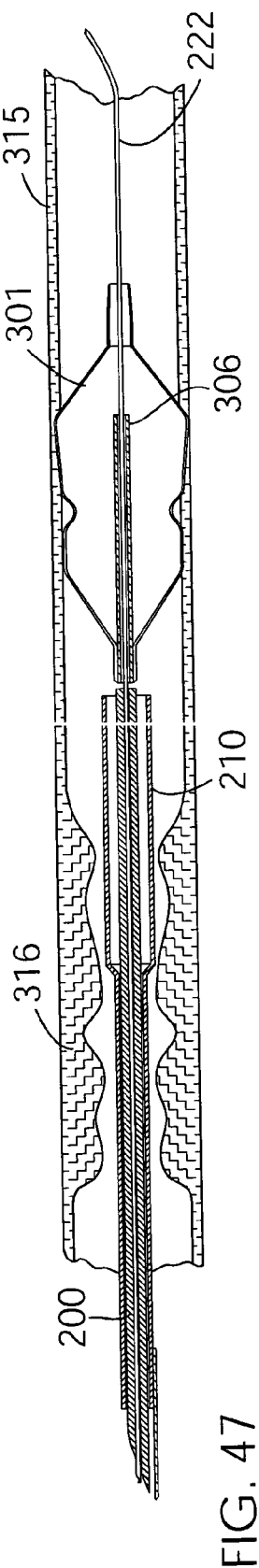

Next the guidewire 222 is inserted into a vasculature 315 and advanced through the vasculature 315 until the guidewire 222 has crossed a site of interest in the vasculature 315 (FIG. 44). A typical site of interest is a stenosed or diseased region 316 of the vasculature 315. The delivery catheter 200 is then threaded over the guidewire 222 by inserting the proximal end of the guidewire 222 into the guidewire lumen 216 at the distal end of the pusher 206, through the lumen 216, and out of the lumen 216 through the proximal guidewire opening 217. The catheter 200 is advanced over the guidewire 222 in a rapid-exchange manner until the reception space 211 is located downstream of the stenosis 316 (FIG. 45).

To deploy the filter 301 at the desired site in the vasculature 315 downstream of the stenosis 316, the proximal handle 214 is moved proximally while holding the distal handle 208 fixed, thereby causing the pull wire 209 and the connector shaft 212 to be pulled proximally. Because the connector shaft 212 is attached to the sheath 210, the sheath 210 also moves proximally while the pusher 206 does not move. In this way, the collapsed filter 301 is uncovered by the sheath 10 while the distal end of the pusher 206 abuts the proximal end of the tubular member 306 of the filter 301. The delivery catheter 200 thus enables the self-expanding filter 301 to expand outwardly to a deployed configuration. The distal end of the pusher 6 acts as an abutment for a controlled, accurate deployment of the filter 301 at the desired site in the vasculature 315.

Figure 48:
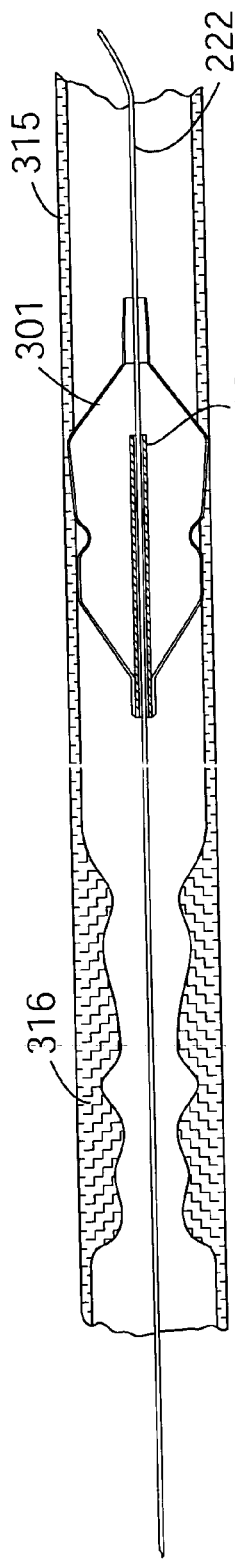
Figure 49:
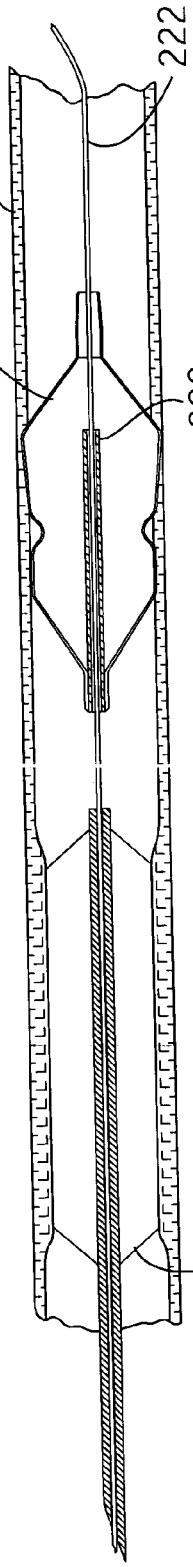

When the filter 301 has been fully deployed at the desired site in the vasculature 315, the delivery catheter 200 is withdrawn from the vasculature 315 over the guidewire 222 in a rapid-exchange manner to leave the deployed filter 301 in place in the vasculature 315 (FIG. 48).

Figure 50:
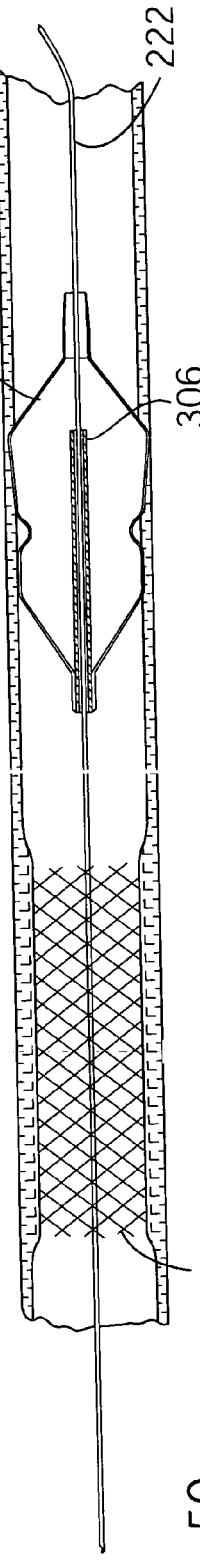
Figure 51:
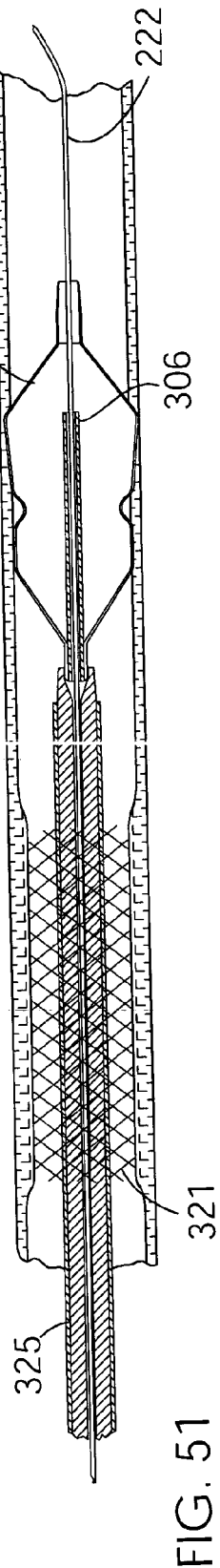

Various procedures can be carried out using the guidewire such as an angioplasty using a balloon 320 (FIG. 49) or a stenting procedure with a stent 321 (FIG. 50). On completion of the procedures a retrieval device such as a retrieval catheter 325 or snare may be used to retrieve the filter (FIGS. 51 to 53). The guidewire 222 may be left in place or removed.

In FIGS. 55 to 57 there is illustrated another delivery catheter 600 according to the invention, which is similar to the delivery catheter 200 and similar elements are assigned the same reference numerals. In this case the distal end of the shaft 212 is not flared outwardly, and the proximal end of the inner tubular member 206 is not inserted into the shaft 212, during delivery of the embolic protection filter 610.

Instead a bridging sleeve 601 is provided mounted around the shaft 212 distally of the marker band 213, as illustrated in FIG. 57. The sleeve 601 extends distally of the distal end of the shaft 212, such that the proximal end of the inner tubular member 306 of the filter 610 may be partially inserted into the sleeve 601 during delivery of the filter 610 (FIG. 57). This arrangement provides a bridge in stiffness between the relatively stiff shaft 212 and the relatively stiff inner tubular member 306 of the filter 610. Thus the possibility of buckling of the relatively flexible sheath 210 is minimised.

It is noted that the filter 610 is of a different configuration to the filter described previously. In particular the inner tubular member 306 of the filter 610 does not have any step formations or protrusions at the proximal end of the inner tubular member 306.

The delivery catheter of the invention is also suitable for over-the-wire exchange over a guidewire. The rapid exchange configuration is not essential.

Figure 58:
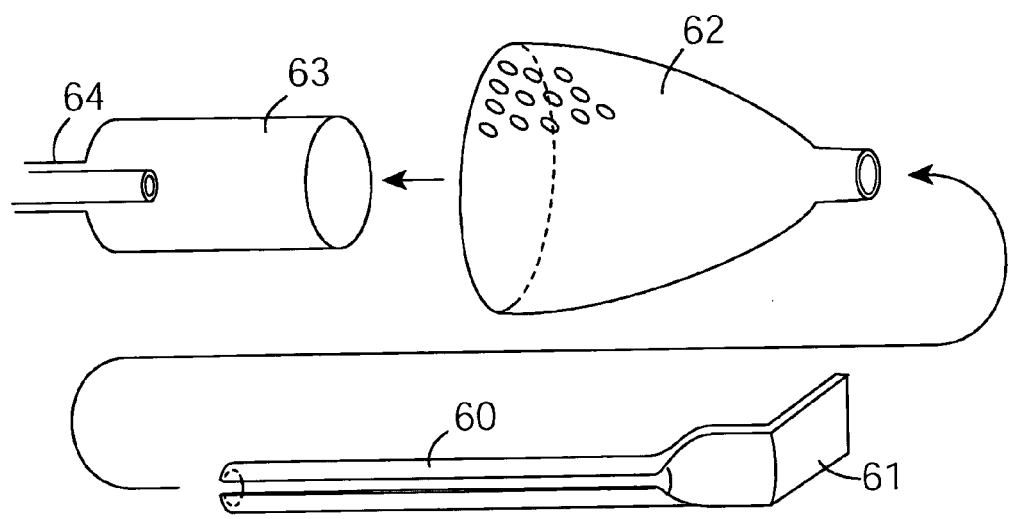
FIGS. 58 to 61 are views illustrating the use of a temporary lumen-defining member for filter delivery.
Figure 59:
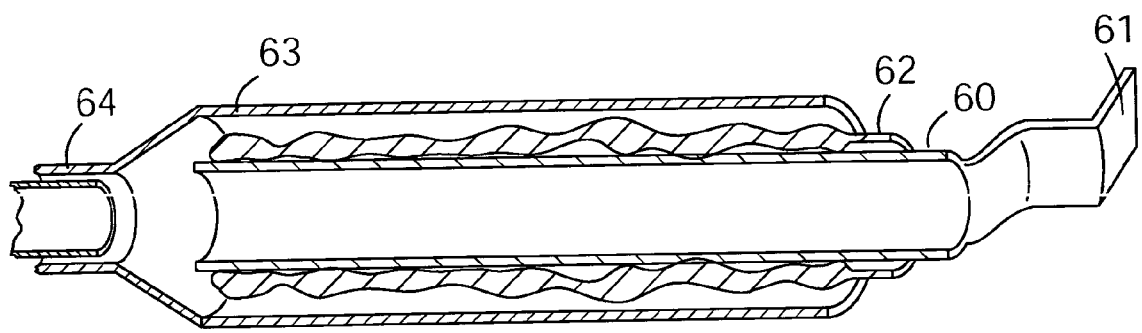
Figure 60:
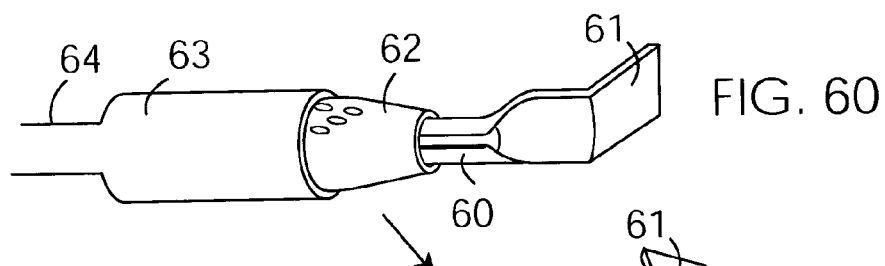
Figure 61:
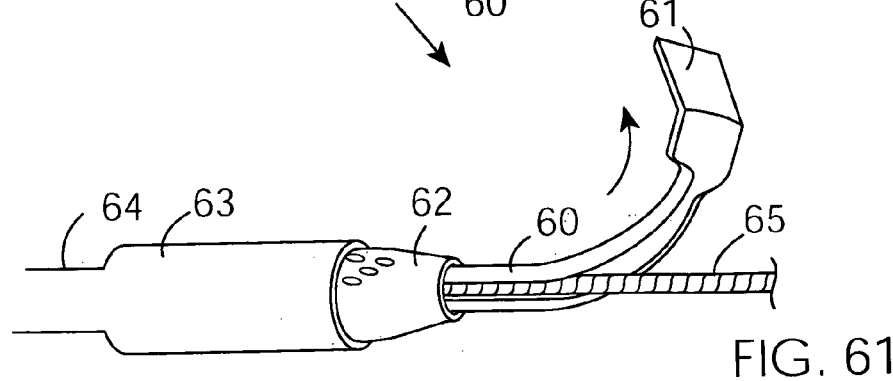
Figure 62:
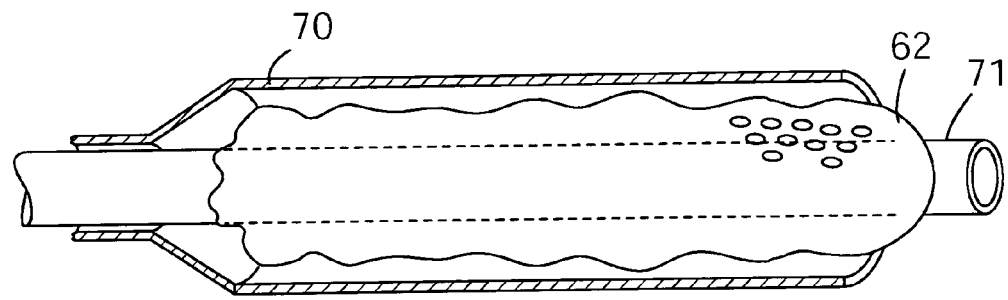
FIGS. 62 to 68 are views illustrating the use of a part of the delivery system to provide a temporary lumen-defining member.

Referring to FIGS. 58 to 61 there is illustrated one means of temporarily providing a tubular lumen in a filter to facilitate delivery of the filter to a desired location. In this case an introducer tool is in the form of a C-shaped tubular member 60 with a distal peel-back feature 61. The tool is inserted into the distal end of the filter 62 as illustrated in FIG. 58. The filter is loaded into a distal pod 63 of a delivery catheter 64 (FIG. 58) and the distal end of the delivery catheter 64 is threaded over the proximal end of a deployed guidewire 65. When the guidewire has passed through the filter 62 the introducer 60 may be pulled away and removed as illustrated in FIG. 61.

Figure 63:
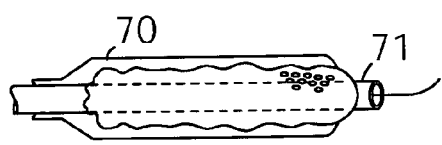
Figure 66:
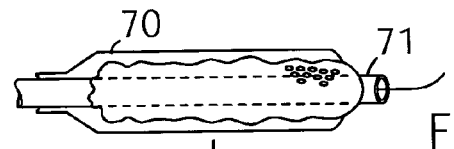
Figure 64:
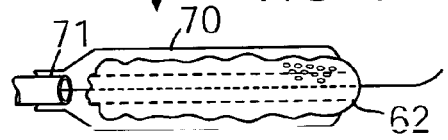
Figure 67:
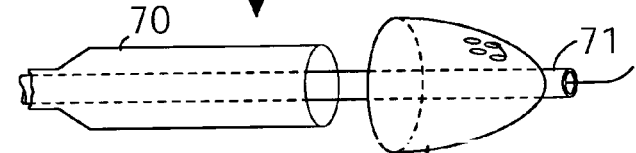
Figure 65:
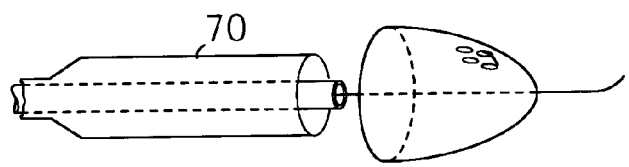
Figure 68:
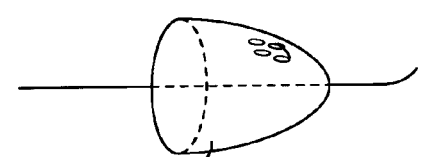

In another arrangement illustrated in FIGS. 62 to 65 the delivery catheter 70 may itself be provided with a member 71 defining a temporary tubular member for a guidewire. The tubular member may also function as a pusher. In one case once the guidewire has traversed the filter 62 the tubular member 71 may be positioned proximal of the filter during delivery and deployment (FIGS. 63 to 65). In another case (FIGS. 66 to 68) the tubular member 71 may extend through the filter up to the stage when the delivery catheter is being withdrawn.

Figure 69:
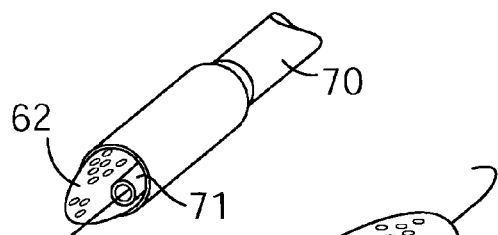
FIGS. 69 and 70 are perspective views of such a lumen-defining member extending to a side of a filter.
Figure 71:
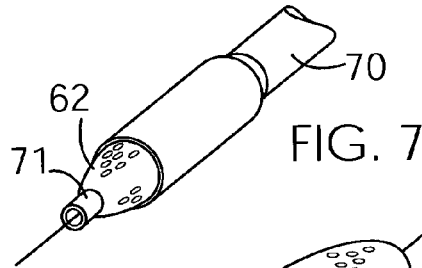
FIGS. 71 and 72 are perspective views of such a lumen-defining member extending through a filter.
Figure 70:
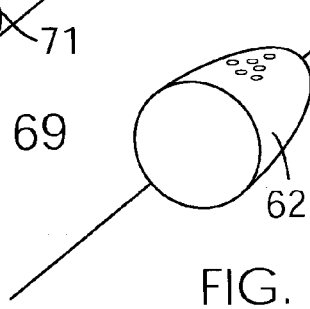
Figure 72:
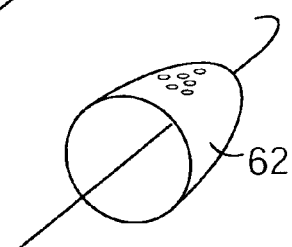

The pusher 71 may pass through the centre (FIGS. 71 and 72) of the filter or may run beside the filter (FIGS. 69 and 70).

Figure 73:
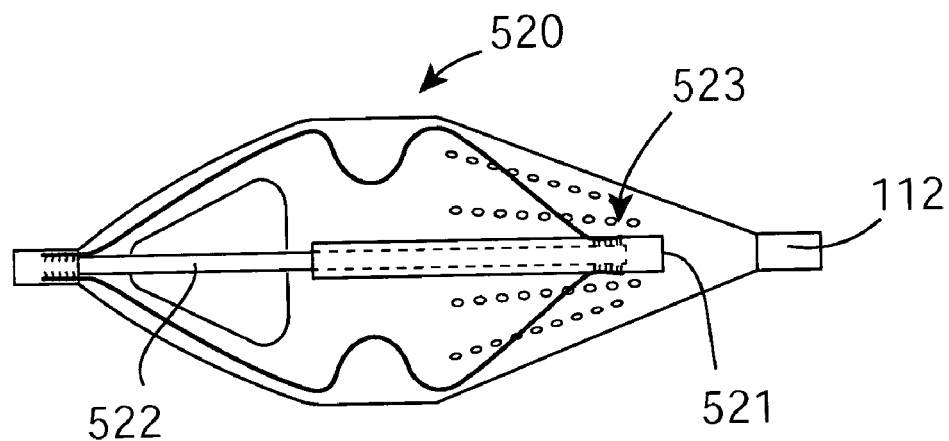
FIG. 73 is a schematic view of another embolic protection filter according to the invention in a deployed configuration.
Figure 74:
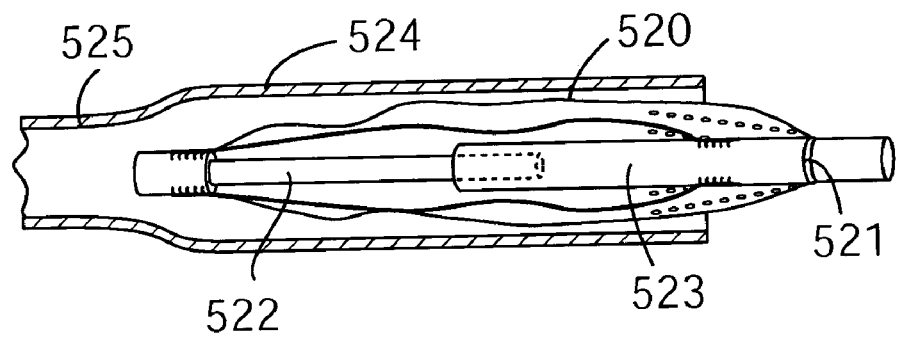
FIG. 74 is a schematic view of the filter of FIG. 73 collapsed in a delivery catheter.
Figure 75:
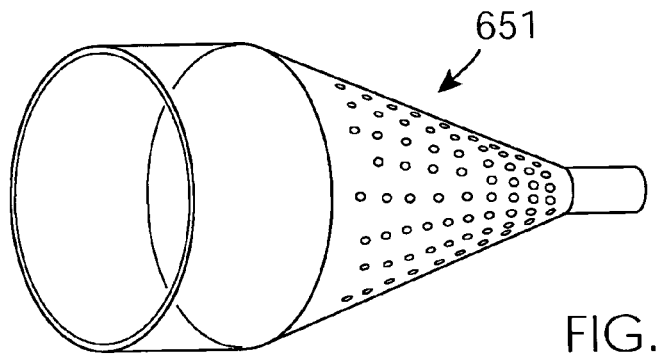
FIG. 75 is a perspective view of another embolic protection filter according to the invention.
Figure 76:
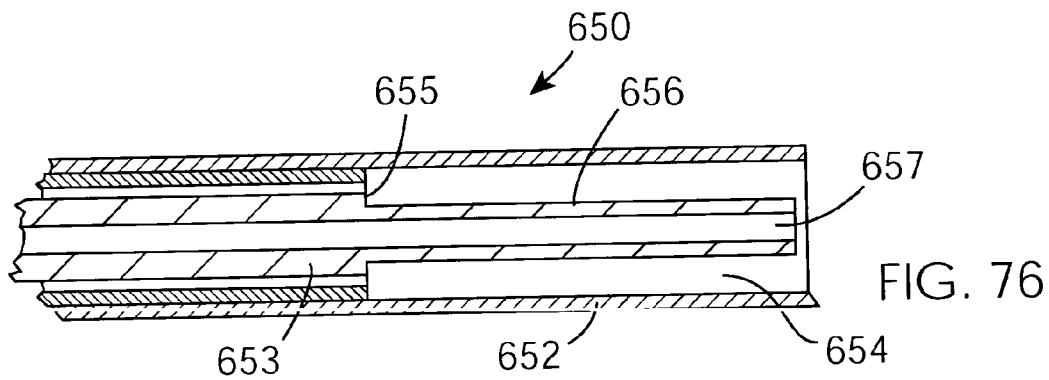
FIG. 76 is a cross-sectional, side view of a delivery catheter according to the invention in a delivery configuration.

In FIGS. 73 and 74, there is illustrated another embolic protection filter 520 according to the invention. In the case of filter 520, the guidewire lumen 521 through the filter 520 is defined by two telescoping tubes 522, 523. The proximal tube 522 is fixed to the filter 520 at the proximal end of the filter 520, and the distal tube 523 is fixed to the filter 520 at the distal end of the filter 520.

In the deployed configuration of FIG. 73, the distal tube 523 telescopes proximally over the proximal tube 522 so that the overall parking space of the filter 520 in a vasculature is minimised. In addition the distal tube 523 is spaced distally of the guidewire aperture 112 to facilitate crossing of the filter 520 with a guidewire without requiring the guidewire to be threaded through the tubes 522, 523.

In the collapsed configuration of FIG. 74, the distal tube 523 telescopes distally over the proximal tube 522 so that the guidewire lumen 521 is defined through the entire length of the filter 520 when collapsed, for example in a pod 524 of a delivery catheter 525.

Figure 77:
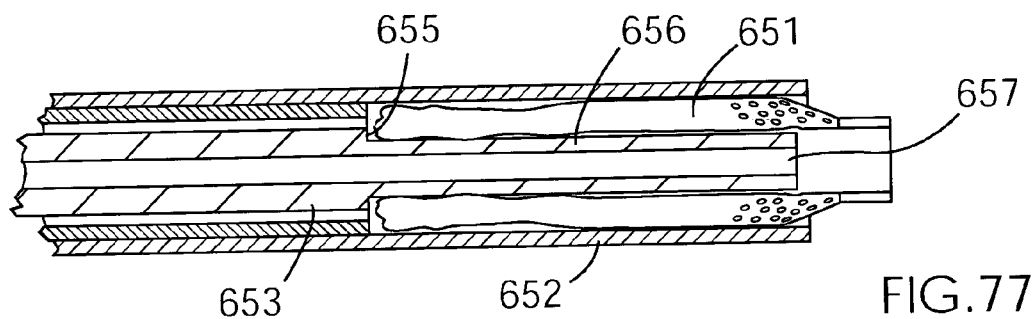
FIG. 77 is a cross-sectional, side view of the filter of FIG. 75 collapsed in the delivery catheter of FIG. 87.

The invention also envisages the use of a delivery catheter 650, as illustrated in FIGS. 75 to 89, which is particularly suitable for delivering an embolic protection filter 651, as illustrated in FIG. 77, the filter 651 not having an inner tubular member to define a guidewire lumen through the filter 651.

Figure 78:
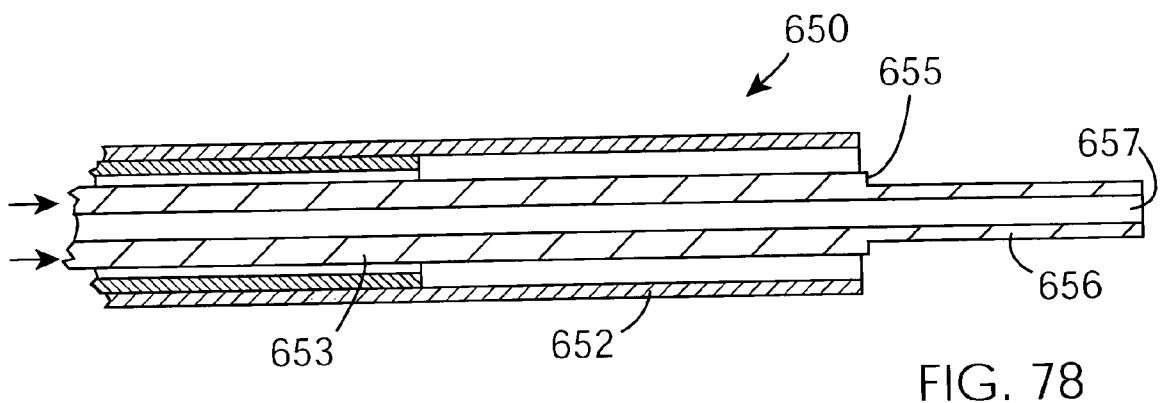
FIG. 78 is a cross-sectional, side view of the delivery catheter of FIG. 76 in a deployment configuration.

The delivery catheter 650 comprises an outer tubular member 652, and an inner tubular member 653, the inner tubular member 653 being movable distally relative to the outer tubular member 652 from a delivery configuration (FIG. 76) to a deployment configuration (FIG. 78).

In the delivery configuration, the catheter 650 defines a reception space 654 for receiving the filter 651 in a collapsed configuration, as illustrated in FIG. 77. When the inner tubular member 653 is moved distally relative to the outer tubular member 652, the filter 651 is pushed distally out of the reception space 654 by means of an engagement between a shoulder 655 of the inner tubular member 653 and the collapsed filter 651.

The invention provides features to enable a guidewire to be repositioned across the filter. It may be necessary to be able to replace the guidewire if the wire became accidentally withdrawn by the user during the procedure. It may then be necessary to replace the wire in order to access the lesion with other devices such as a balloon or stent catheter or even the filter retrieval catheter. Merely advancing a wire up to the filter is unlikely to provide sufficient support in all cases. Guidewire replacement may also be needed if the user desires to use a wire with different properties during the procedure. For example a very torqueable wire may be ideal for initially accessing and crossing the lesion, and may have adequate support to enable the filter to be delivered and deployed, but may not have sufficient support to enable a stiffer stent delivery system to reach the lesion. The invention facilitates removal of the first wire and replacement with a more supportive guidewire to facilitate use of the stent delivery system. This may be achieved without having to use an additional exchange catheter.

This invention describes a filter which comprises a guidewire recrossing feature, wherein this feature may comprise some or all of a guiding funnel, a pathway and a blood restrictor. A guiding funnel is used as this operation will be performed "blind". In general, it would be difficult to replace a guidewire through a tubular lumen while the filter is in the patient. In the invention the guidewire may be passed through the distal filter neck. The distal cone of the filter will act as a guiding channel. However the guidewire tip is very flexible—if it is to open a "valve" or blood restrictor it will need to have good push. In order to provide this push it is necessary to restrain the guidewire tip within a relatively narrow channel—this channel is provided by the filter neck. A restrictor may be provided to prevent any loss of embolic material while the first guidewire was absent—during which period the neck of the filter would be an open hole if no restrictor were present. This restrictor is intended simply to close and prevent blood flow in the absence of a guidewire. Once there is no blood flow through the filter neck embolic material will not collect there and will not restrict the passage of the second guidewire.

Figure 79:
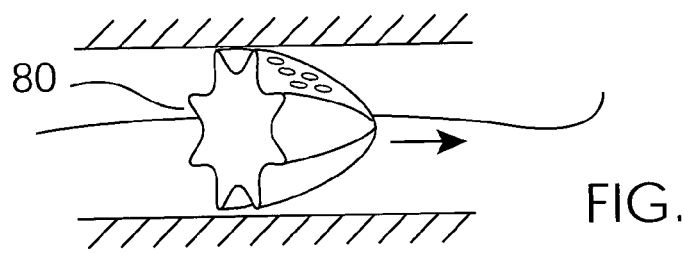
FIGS. 79 and 80 are views of a filter with a guidewire passageway at the side thereof.
Figure 80:
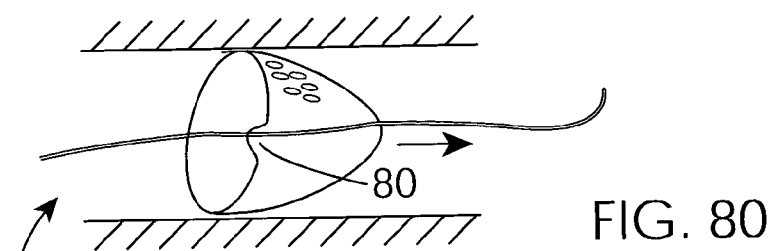
Figure 81:
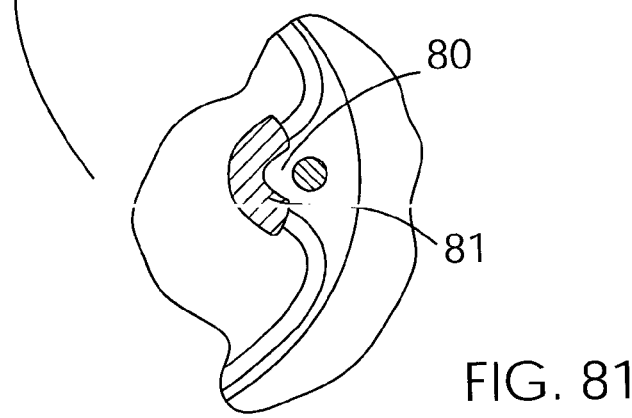
FIG. 81 is an enlarged view of a detail of FIG. 80.
Figure 82:
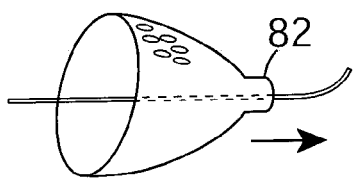
FIGS. 82 to 84 are perspective views illustrating different guidewire paths.
Figure 83:
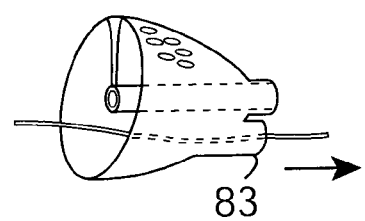
Figure 84:
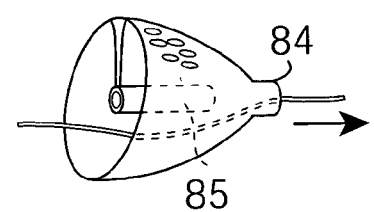
Figure 85:
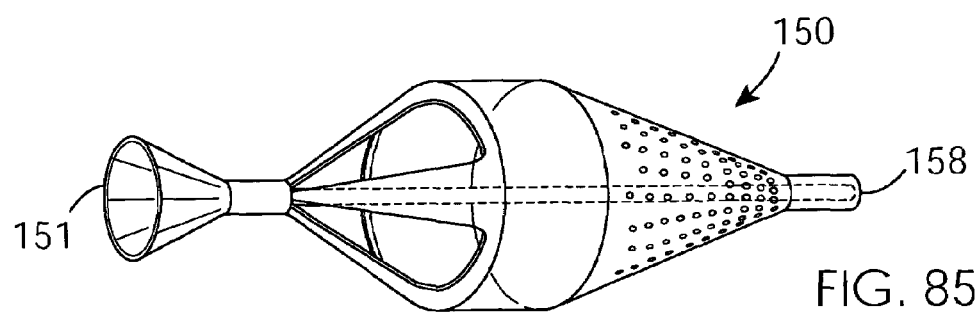
FIG. 85 is a perspective view of another embolic protection filter according to the invention.

Various guideways may be provided for a guidewire to assist crossing of a filter. Referring to FIGS. 79 to 81 the pathway may be provided around the filter, for example in a side channel 80. A radiopaque feature 81 may be provided on the filter to guide a user to the passageway. Alternatively the pathway may be through the filter to a single exit 82 (FIG. 82), a separate exit 83 (FIG. 83) or through the same exit 84 using a shortened tubular member 85 illustrated in FIG. 84 and described in more detail herein. In these cases the guidewire passage/hole may be sealed to prevent passage of embolic therethrough as will be described in more detail below.

Referring now to FIGS. 85 to 92, there is illustrated another embolic protection filter 150 according to the invention. The filter 150 comprises a receiver to guide a docking device into association with the filter 150. In this case, the receiver is configured to guide a guidewire, such as the guidewire 130, into the guidewire lumen 112. The receiver is provided by a funnel 151 which diverges outwardly proximally, the funnel 151 being mounted to the filter 150 to extend proximally of the inlet end of the filter 150.

In this specification, the term funnel will be understood to mean any orifice with a cross-sectional area that decreases with distance.

Figure 86:
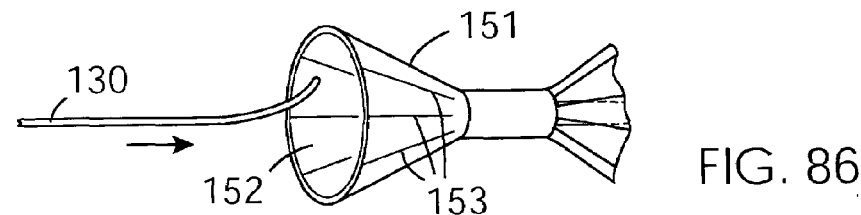
FIG. 86 is an enlarged, perspective view of a receiver of the embolic protection filter of FIG. 85.

The funnel 151 may comprise a collapsible funnel body in the form of a membrane 152, which in this case is supported by a collapsible funnel support, in the form of a plurality of support fingers 153. The fingers 153 are pivotally mounted to the filter 50 and are biased to move the filter membrane 152 from a collapsed configuration for movement through the vasculature, to an outwardly extended configuration for guiding the guidewire 130, as illustrated in FIG. 86. The funnel 151 may be of a radiopaque material.

The funnel 151 may be used to guide the guidewire 130 along a pathway that enables the guidewire 130 to cross the filter 150. The funnel 151 allows the procedure of leading the small diameter guidewire 130 through the small diameter guidewire lumen of the filter 150 to be performed more easily by guiding the tip of the guidewire 130 towards the proximal end of the guidewire lumen 158.

Figure 87:
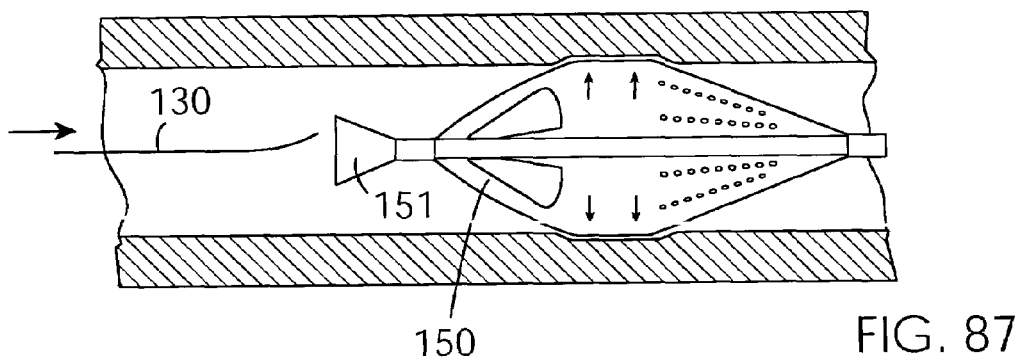
FIGS. 87 to 89 are partially cross-sectional, side views illustrating guiding of a guidewire through the embolic protection filter of FIG. 85.
Figure 88:
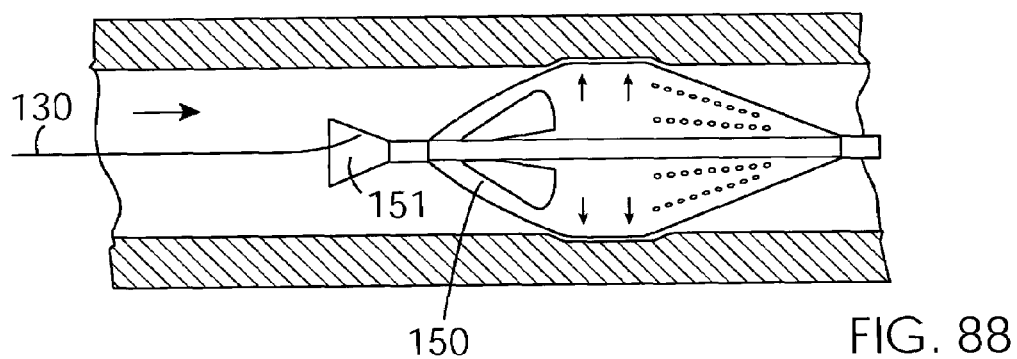
Figure 89:
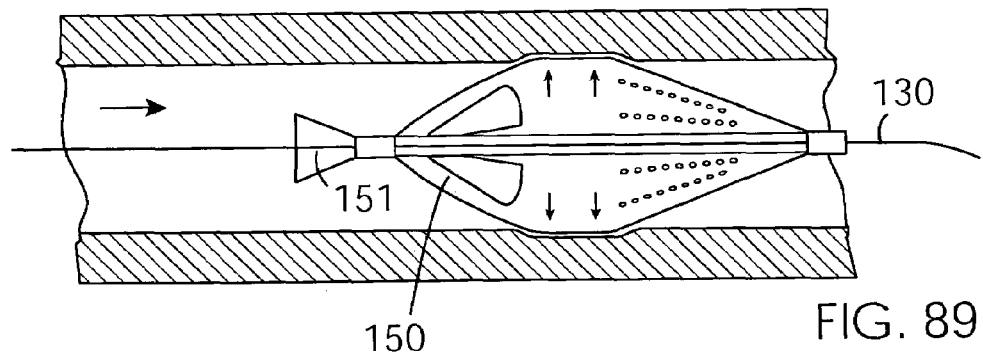
Figure 90:
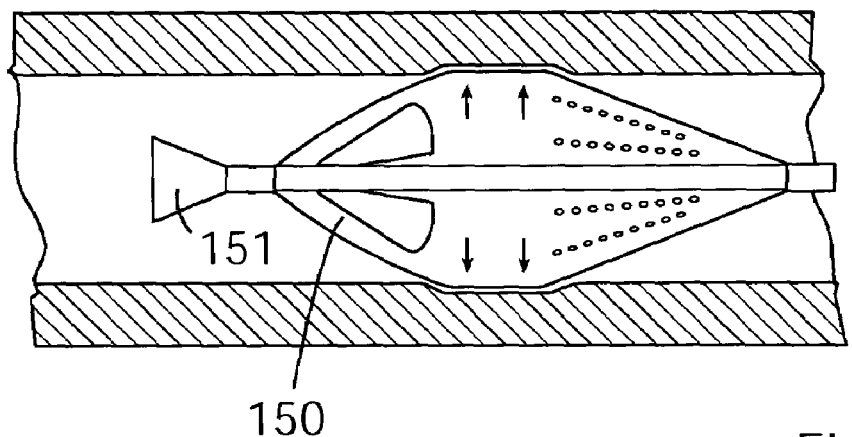
FIG. 90 is a partially cross-sectional, side view of the embolic protection filter of FIG. 85 deployed in a vasculature.
Figure 91:
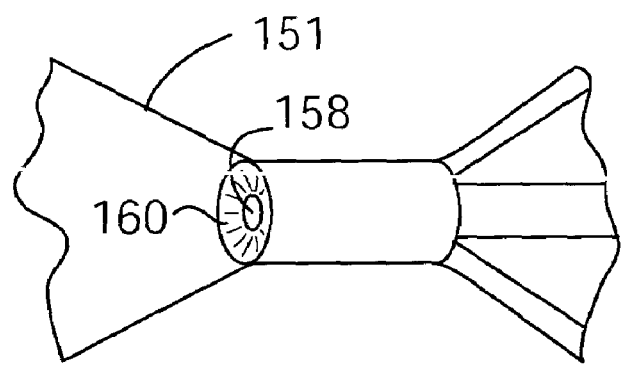
FIGS. 91 and 92 are enlarged, perspective views of seals of the embolic protection filter of FIG. 90.

Use of the funnel 151 is particularly beneficial in the case where it is desired to lead the guidewire 130 through the guidewire lumen while the filter 150 is deployed in the vasculature, as illustrated in FIGS. 87 to 89. The funnel 151 enables a clinician to accurately and quickly thread the guidewire 130 through the guidewire lumen without risk of puncturing the filter body or of disturbing the fitter 50 from its deployed position in the vasculature in apposition with the wall of the vasculature.

The filter 150 further comprises at least one, and in this case two, seals 160, 161 to seal the guidewire lumen 158 to prevent embolic material from passing through the guidewire lumen 158, when the filter 150 is in use in the vasculature.

The seals 160, 161 are self-closing. In this case one seal 160 located at the proximal end of the filter 150, and the other seal 161 located at the distal end of the filter 150.

The proximal seal 160 may be in the form of a tubular member of a soft membrane material. The guidewire lumen 158 extends through the tubular seal 160 and the seal 160 is closable down to seal the guidewire lumen 158.

Figure 92:
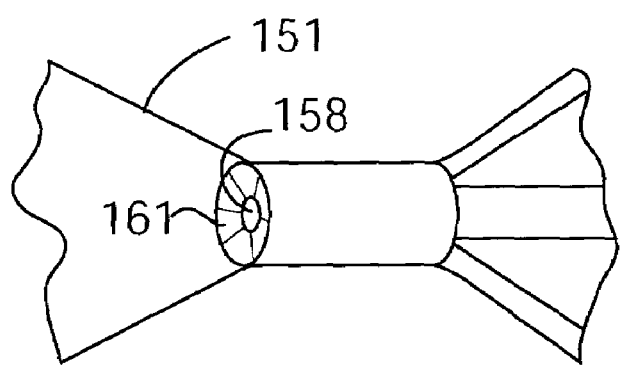
Figure 93:
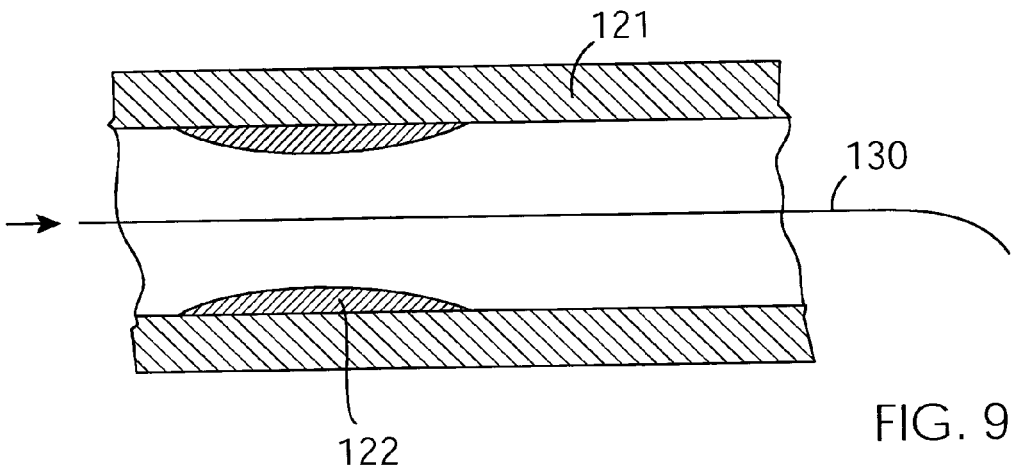
FIGS. 93 to 110 are partially cross-sectional, side views of the embolic protection filter of FIG. 85 in use.
Figure 94:
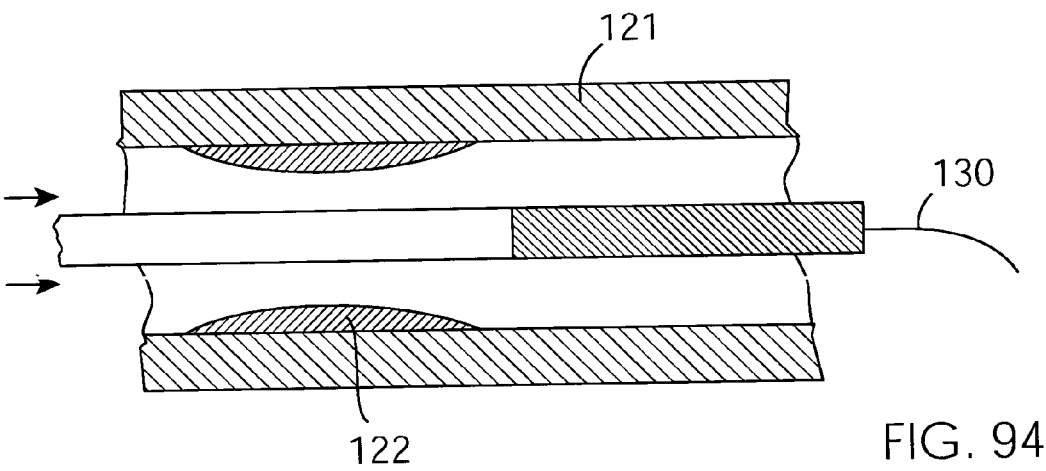
Figure 95:
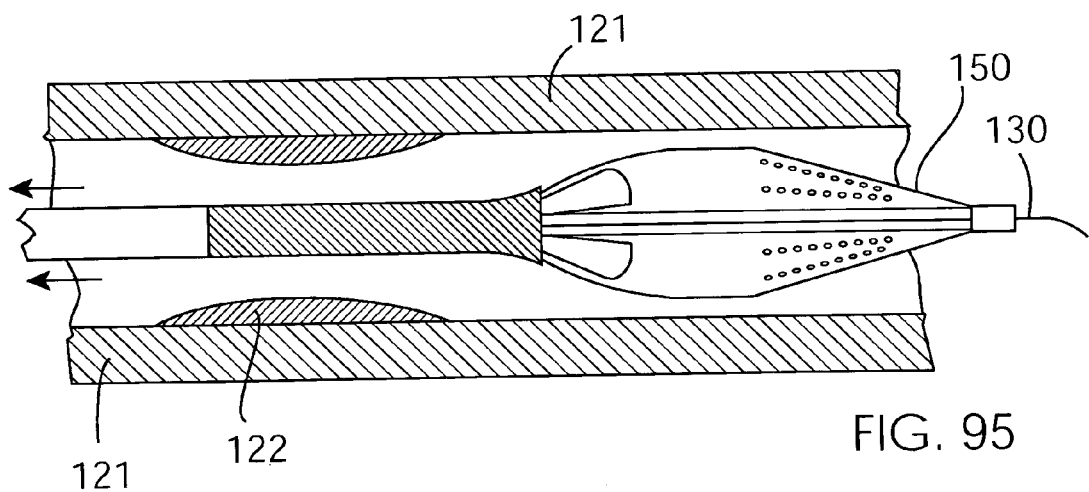
Figure 96:
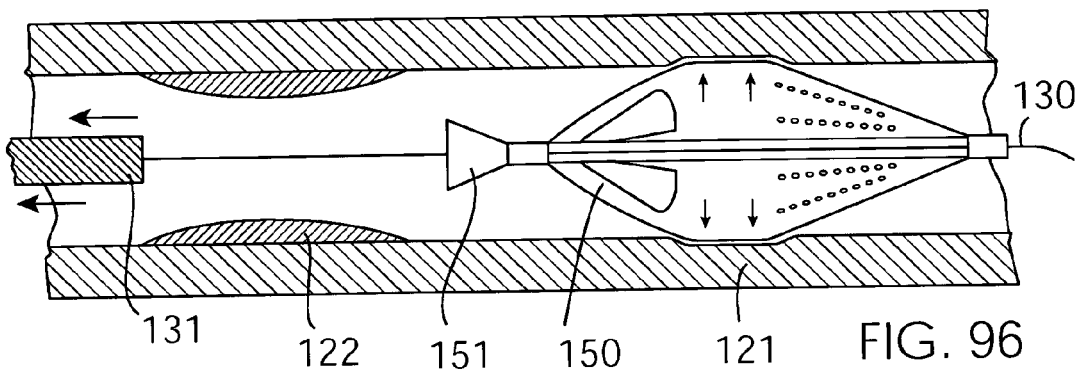
Figure 97:
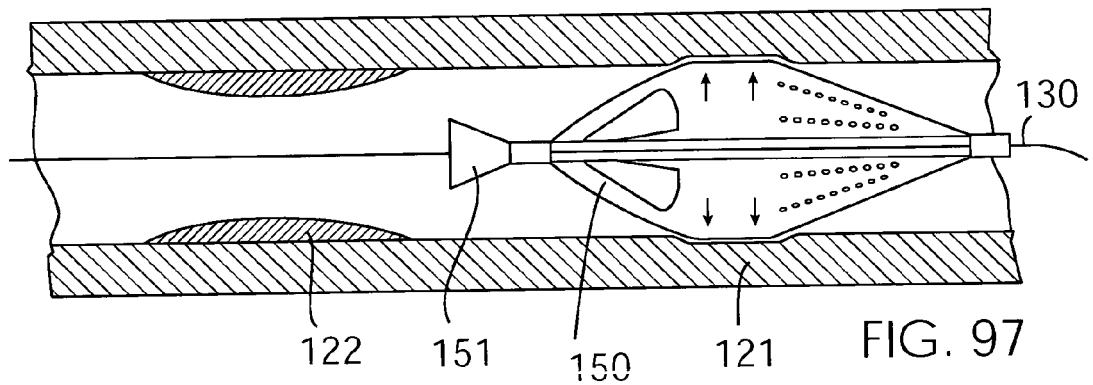
Figure 98:
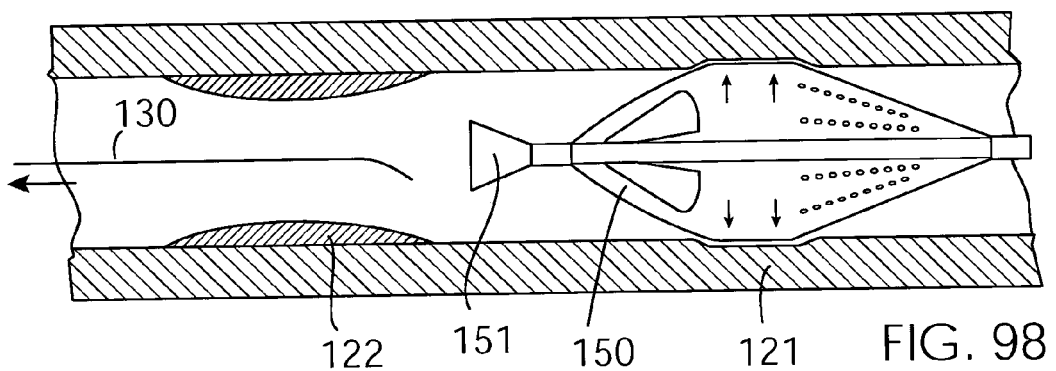
Figure 99:
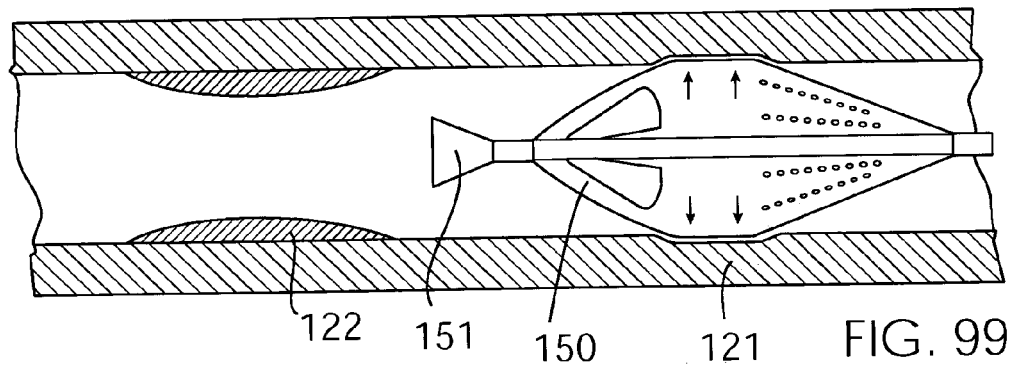
Figure 100:
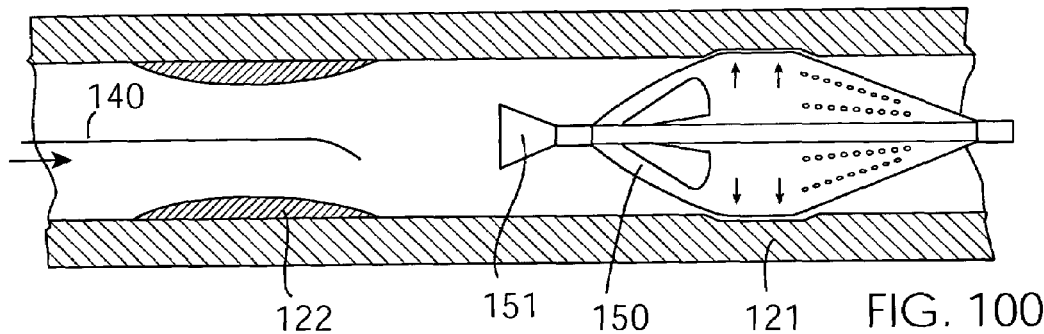
Figure 101:
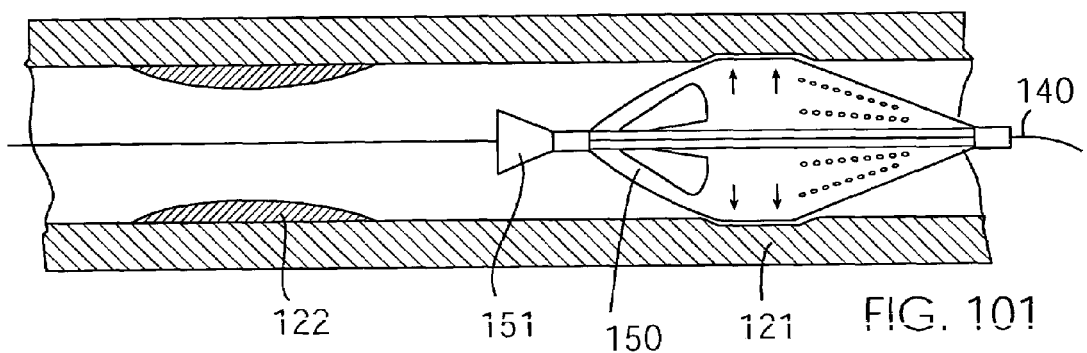
Figure 102:
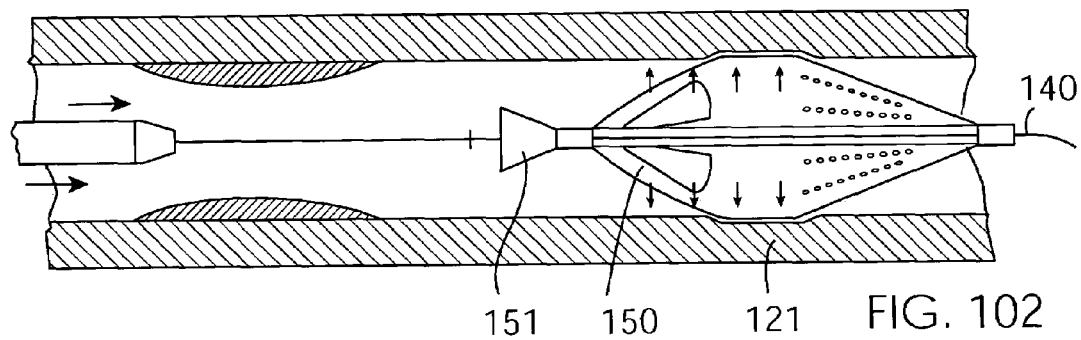
Figure 103:
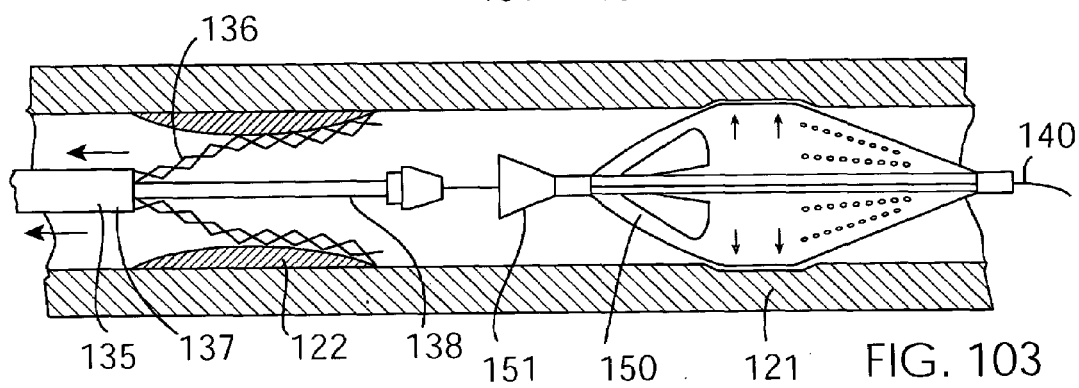
Figure 104:
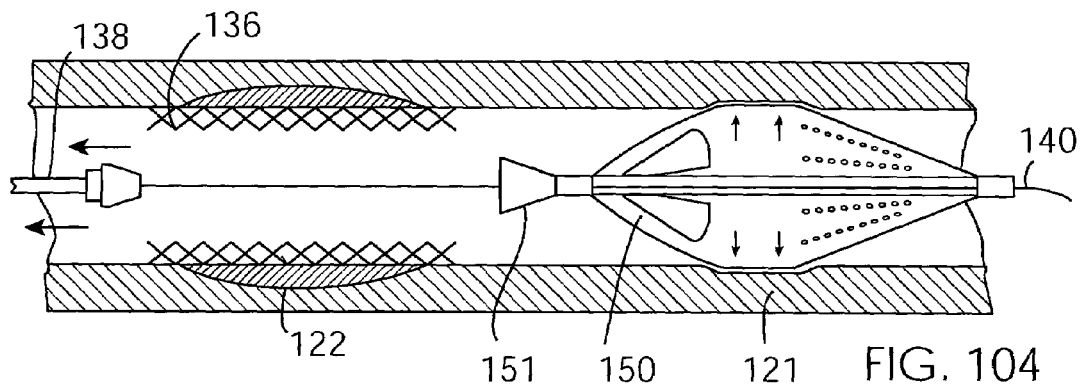
Figure 105:
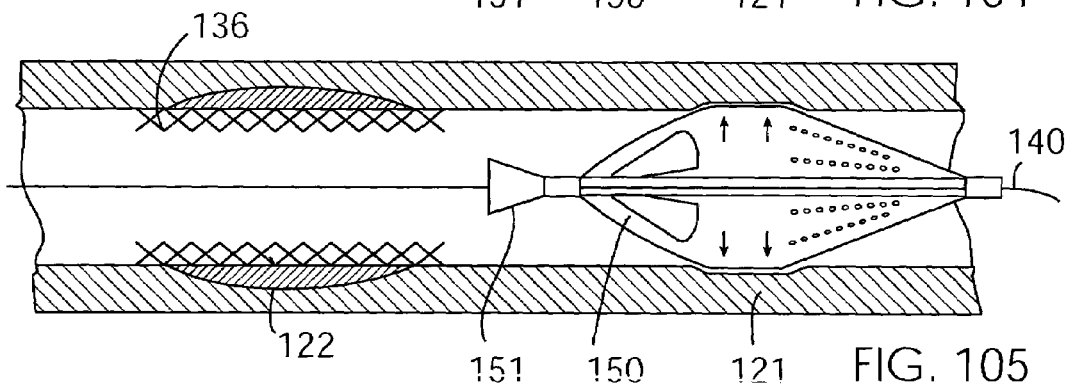
Figure 106:
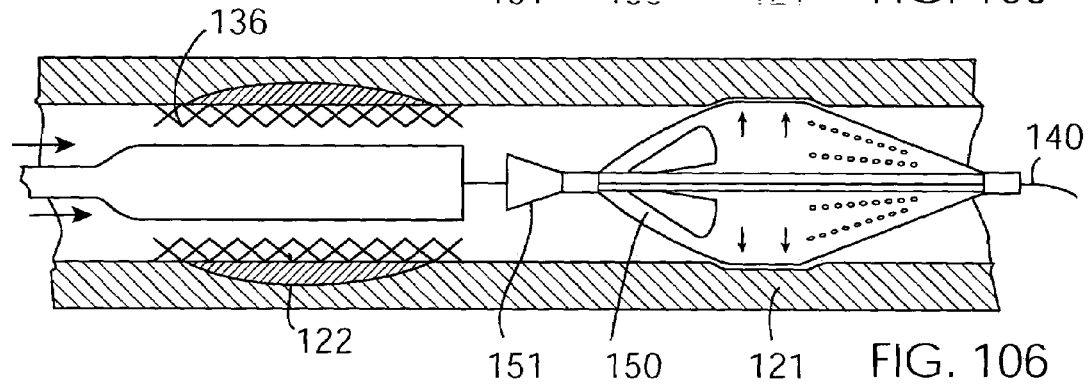
Figure 107:
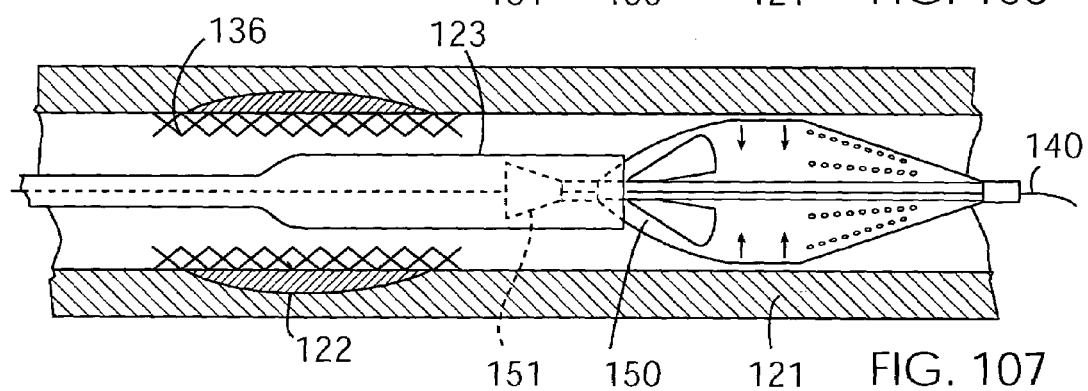
Figure 108:
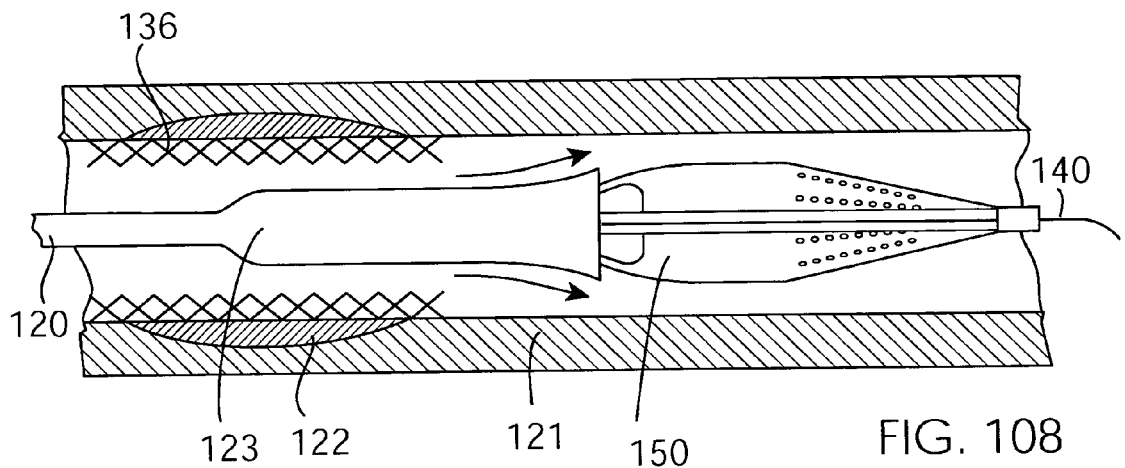
Figure 109:
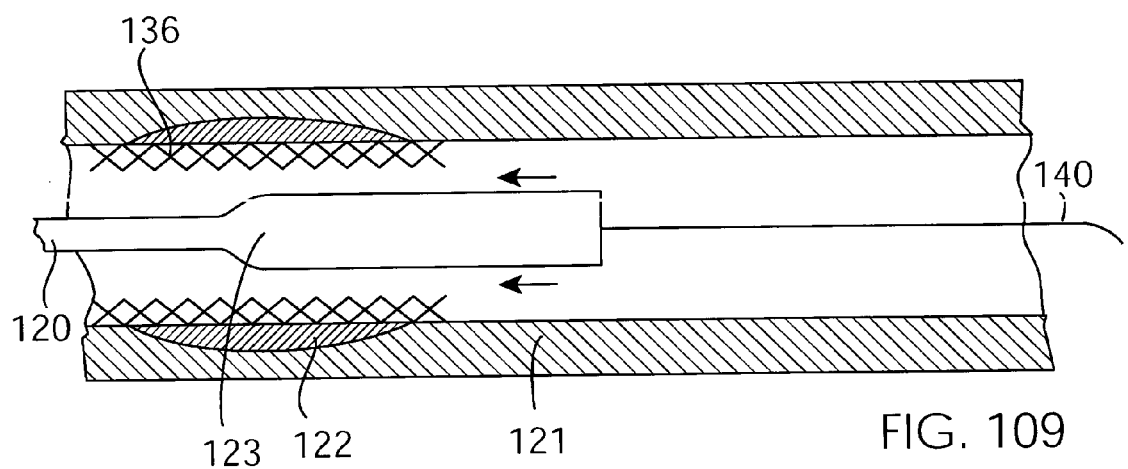
Figure 110:
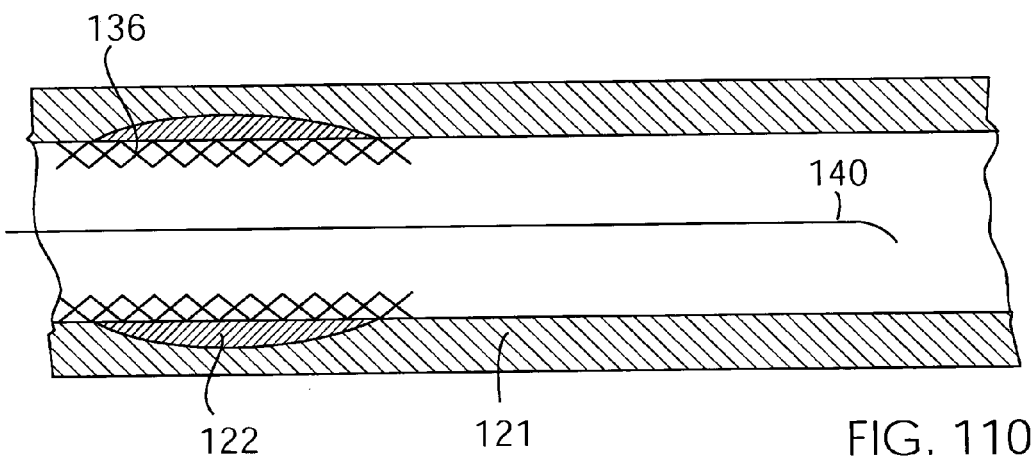
Figure 111:
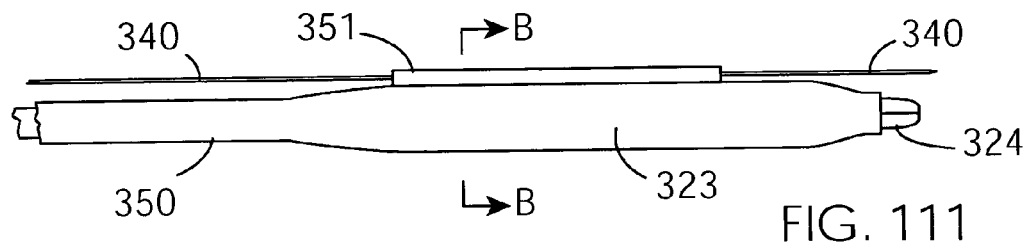
FIG. 111 is a side view of another retrieval catheter according to the invention passing over a guidewire.
Figure 112:
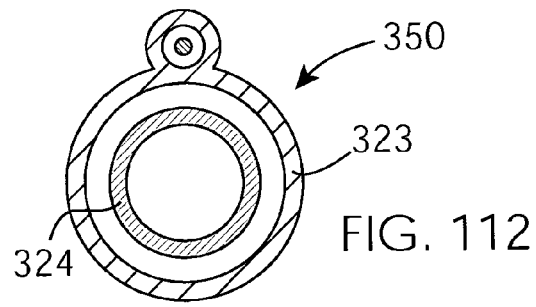
FIG. 112 is a view along line B—B in FIG. 111.

The distal seal 161 is in the form of a tubular member with two or more, and in this case seven, circumferentially overlapping flaps, as illustrated in FIG. 92. This seal 161 is also closable down to seal the guidewire lumen 158.

It will be appreciated that the guidewire lumen 158 can be provided as any suitable passageway through the filter 150. The guidewire lumen 158 does not have to be located along the central axis of the filter 150. The guidewire lumen 158 may be radially offset from the longitudinal axis of the filter 150.

When the guidewire 130 is extended through the guidewire lumen 158, the seals 160, 161 self-close around the guidewire 130 to prevent emboli flowing through the guidewire lumen 158. Upon removal of the guidewire 130 from the guidewire lumen 158 while the filter 150 is deployed in the vasculature, the seals 160, 161 self-close down to completely close off the guidewire lumen 158.

In this manner, the seals 160, 161 ensure that no blood flow potentially carrying harmful embolic material can pass through the guidewire lumen 158. All blood flows into the filter body through the inlet openings and out of the filter body through the small outlet openings, thereby trapping and safely retaining the undesired embolic material within the filter 150.

After an embolic protection filter has been delivered over a guidewire and deployed in a vasculature, it is not always possible to withdraw the guidewire from the vasculature before collapsing and withdrawing the filter from the vasculature.

However in some cases it may be necessary to withdraw the guidewire over which the filter was delivered while leaving the filter deployed in the vasculature.

Examples of when this need may arise are:
when a high torque guidewire is used to facilitate filter delivery and deployment, and a stiffer guidewire is subsequently used to provide additional support during delivery and deployment of a stent;
when a guide catheter has prolapsed;
when a guidewire is withdrawn into a guide catheter to accelerate rate of resolution of a spasm.

When this need does arise, the filter 150 of the invention may be used to filter potentially harmful emboli from a vasculature when the guidewire is withdrawn, while the filter remains deployed in the vasculature, as illustrated in FIGS. 93 to 110.

A first guidewire 130 is introduced into and advanced through the vasculature 121 to cross the treatment location 122 (FIG. 93), and the filter 150 is delivered through the vasculature 121 and deployed distally of the treatment location 122 (FIGS. 94 to 97), in a manner similar to that described previously.

In the outwardly extended configuration, the deployed filter 150 is retained in position in the vasculature 121 against substantial longitudinal movement by the radial apposition force of the filter body against the wall of the vasculature 121. The first guidewire 130 can thus be withdrawn from the guidewire lumen of the filter 150, and completely withdrawn from the vasculature 121 without disturbing the outwardly extended configuration of the filter 150 in the vasculature 121.

The deployed filter 150 is retained in position in the vasculature 121 against substantial longitudinal movement by means of the radial apposition force exerted by the filter support on the filter body and the vasculature wall, as described previously.

A second guidewire 140 is then introduced into the vasculature 121 and advanced through the vasculature 121 until the second guidewire 140 crosses the desired treatment location 122. The tip of the second guidewire 140 is guided towards the proximal end of the guidewire lumen by engagement of the guidewire tip with the funnel 151, and the second guidewire 140 is then lead through the guidewire lumen.

A stent 136 may then be delivered through the vasculature 121, and deployed at the treatment location 122 using the stent delivery catheter 135. In this case, the stent delivery catheter 135 passes over the second guidewire 140. After completion of the interventional procedure, the retrieval catheter 120 is advanced to cross the stent 136 and the treatment location 122, and the tip 125 is engaged with the filter 150. As the tip 125 passes through the funnel 151, the funnel 151 is caused to collapse down to the collapsed configuration. The filter 150 is then collapsed and retrieved into the retrieval catheter 120 and withdrawn from the vasculature 121. Upon collapse of the filter 1, the apposition of the filter with the vasculature 121 is released.

The filter 150 ensures any embolic material generated during the interventional procedure is captured and safely removed from the vasculature 121.

The second guidewire 140 may be of a different diameter, or have different material properties to the first guidewire 130. It may thus be easier or more suitable for the clinician to advance the stent delivery catheter 35 over the second guidewire 140 rather than over the first guidewire 130. For example, it is sometimes the case that a high torque guidewire 130 is used to facilitate filter delivery and deployment, and a stiffer guidewire 140 is used subsequently to provide additional support during delivery and deployment of a stent.

In some cases, it may be necessary or desirable to withdraw the second guidewire 140 from the filter 150 and the treatment location 122 after deployment of the stent 136, and then to advance a third guidewire through the vasculature 121 to the filter, the retrieval catheter 120 then being advanced over the third guidewire to retrieve the filter 150. This invention enables such a procedure to be carried out.

Furthermore withdrawing a guidewire into a guide catheter may accelerate the resolution of spasm and reduce the risk of ischaemia.

Figure 190:
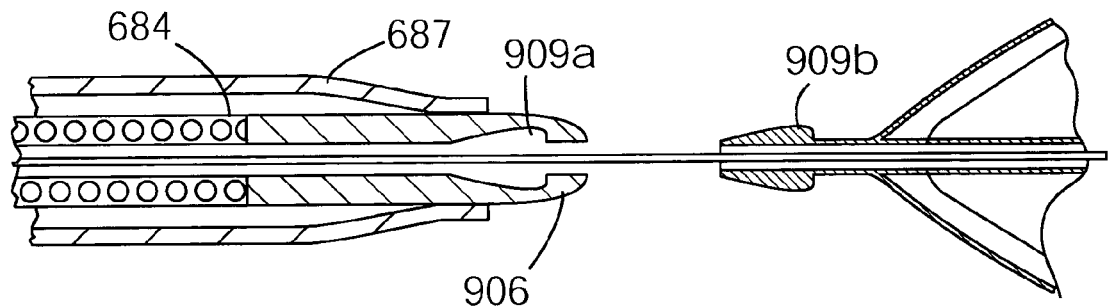
FIGS. 190 to 192 are cross-sectional side views illustrating retrieval of an embolic protection filter using another retrieval catheter of the invention.
Figure 191:
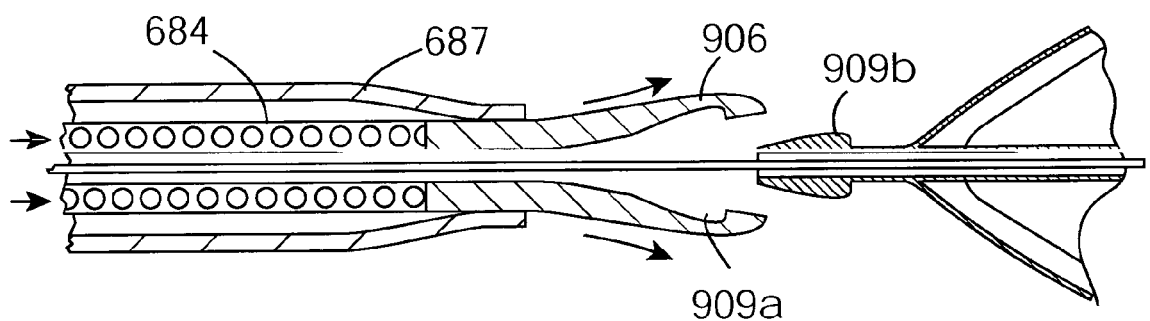
Figure 192:
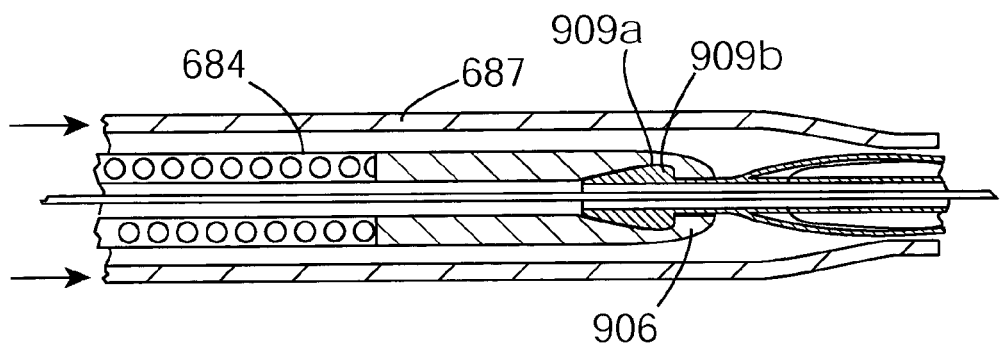

Referring to FIGS. 111 to 114, there is illustrated another retrieval catheter according to the invention, which is similar to the retrieval catheter of FIGS. 190 to 192. In this case, the catheter body 323 defines a guidewire lumen 351 radially offset from the coupling member 324. The guidewire lumen 351 extends through only part of the catheter body 323 to facilitate passage of the catheter body 323 over a guidewire, such as the guidewire 340, in a rapid exchange manner.

In use, the retrieval catheter 350 may be used to retrieve the filter deployed in the vasculature 321.

Figure 113:
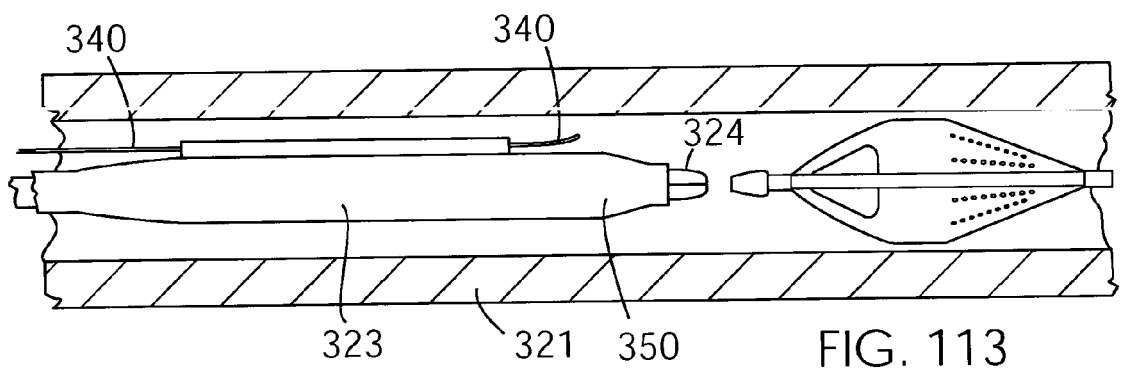
FIGS. 113 and 114 are partially cross-sectional, side views illustrating retrieval of a filter of FIG. 1 using a retrieval catheter.
Figure 114:
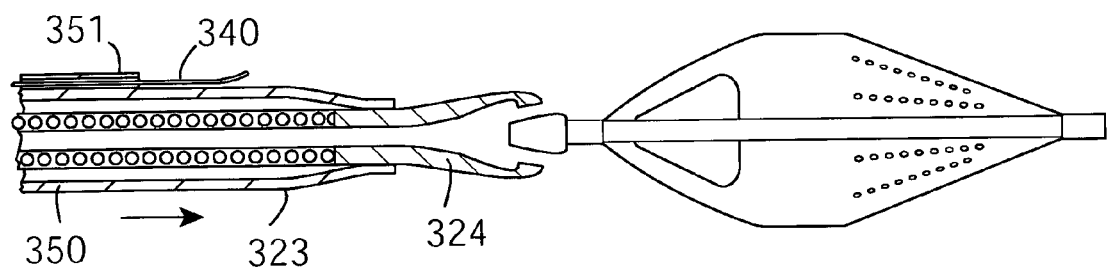

In one possible procedure, the second guidewire 340 is not led through the guidewire lumen 312 of the filter. Instead the second guidewire 340 is advanced until the guidewire 340 has crossed the treatment location and the guidewire tip is proximally of the filter (FIG. 113). The filter is then retrieved into the catheter body 323. During this procedure the retrieval catheter 350 may be advanced distally off the end of the guidewire 340.

FIG. 115 illustrates another filter 170 according to the invention. In this case, the funnel 151 is mounted to the filter 170 distally of the inlet end of the filter 170, so that the funnel 151 is located at least partially within the filter 170.

It will be appreciated that the receiver may be detachably mounted to the filter. For example, the receiver may be mounted to the filter after deployment in a vasculature, and/or may be detached from the filter before retrieval of the filter from a vasculature.

In addition, the receiver may be radially offset from the longitudinal axis of the filter.

Referring to FIGS. 116 and 117, there is illustrated another filter 180 according to the invention. The funnel is provided, in the case of filter 180, by sloping walls 181 of the filter body at the inlet end. As the guidewire 130 is advanced to the filter 180, the tip of the guidewire 130 meets the sloping walls 181 of the filter body and is guided distally inwardly towards the proximal end of the guidewire lumen. In this manner, the sloping walls 181 enable the guidewire 130 to be easily and quickly threaded into the guidewire lumen.

The angle of inclination α of these sloping walls 181 can be altered, as indicated in FIG. 117, to suit the characteristics of the interventional procedure, and/or the vasculature, and/or the guidewire.

The large inlet openings enable substantially unrestricted flow into the filter body, and the sloping walls 81 may be radiopaque material to aid guidewire passage.

FIG. 118 illustrates a further filter 190 according to the invention. In this case, the filter 190 has a guidewire aperture 192 for passing the filter 190 over the guidewire 130, and the filter 190 has a single, large inlet opening 191 at the inlet end of the filter 190. The single, large inlet opening 191 provides no resistance to blood flow into the filter body.

The sloping walls 192 at the outlet end of the filter 190 provides the funnel, in this case, to guide the guidewire 130 towards the guidewire aperture 192.

It will be appreciated that the outlet openings are smaller, in this case, than the guidewire diameter, thus the guidewire 130 does not snag or pass through the outlet openings but instead the guidewire 130 is guided distally inwardly to the guidewire aperture 192.

The filter 190 may have a guidewire aperture 192 for passing the filter 190 over the guidewire 130, and the filter 190 has a single, large inlet opening 191 at the inlet end of the filter 190. The single, large inlet opening 191 provides no resistance to blood flow into the filter body.

Figure 119:
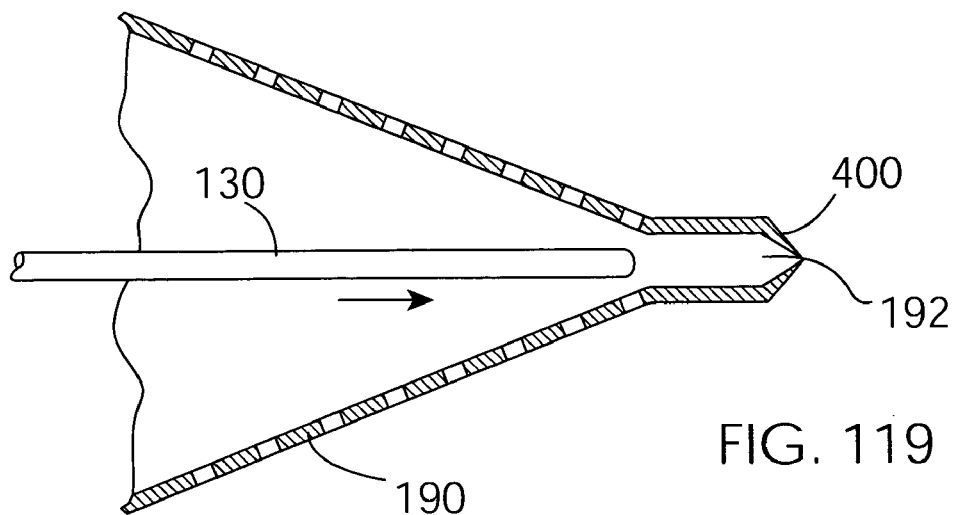
FIGS. 119 and 120 are partially cross-sectional, side views of the embolic protection filter of FIG. 118 guiding a guidewire through the embolic protection filter.
Figure 120:
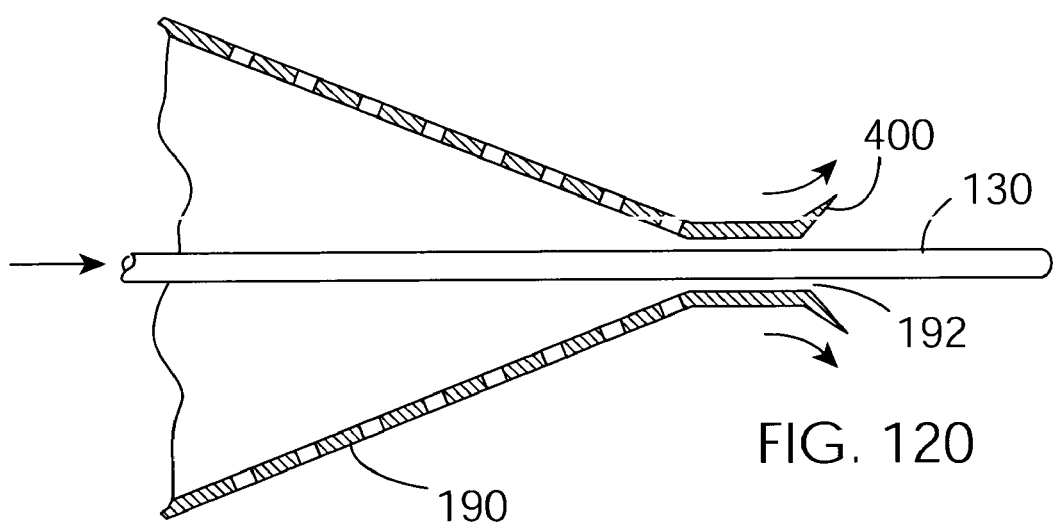

The sloping walls 190 at the outlet end of the filter 190 provides the funnel, in this case, to guide the guidewire 130 towards the guidewire aperture 192, as illustrated in FIGS. 119 and 120.

It will be appreciated that the outlet openings are smaller, in this case, than the guidewire diameter, thus the guidewire 130 does not snag or pass through the outlet openings but instead the guidewire 130 is guided distally inwardly to the guidewire aperture 192.

Figure 121:
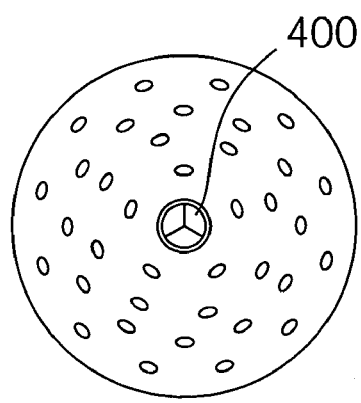
FIG. 121 is an end view of the embolic protection filter of FIG. 118.
Figure 122:
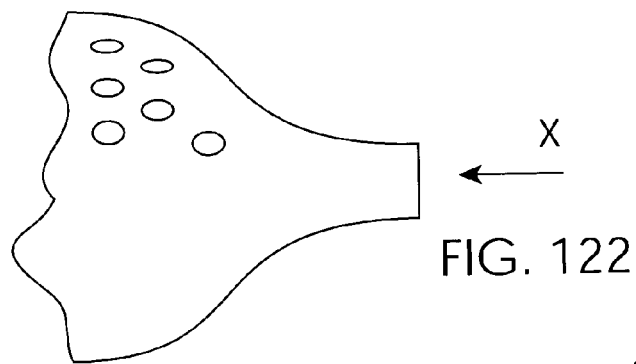
FIG. 122 is a side view of a distal end of a filter.
Figure 123:
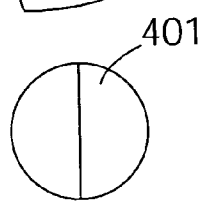
FIGS. 123 to 126 are end views in the direction of the arrow X of FIG. 122 of various outlet seals.
Figure 124:
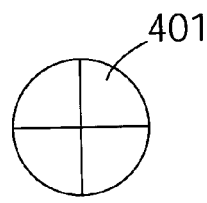
Figure 125:
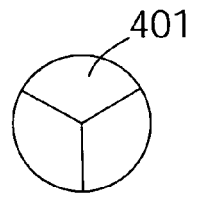
Figure 126:
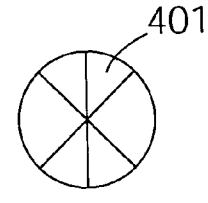
Figure 127:
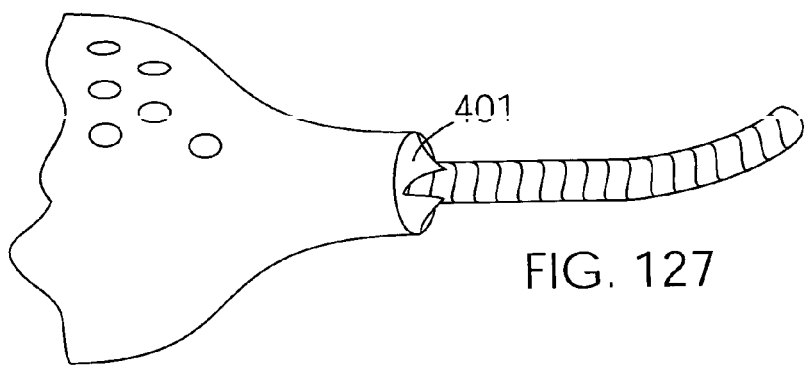
FIG. 127 is a perspective view of a distal end of the filter of FIGS. 122 to 126, in use.

As illustrated in FIGS. 119 to 121 the filter 190 further comprises a distal seal at the guidewire aperture 192 in the form of an elastomeric self-sealing valve 400. The valve 400 has co-operating flaps which meet centrally to close off the guidewire aperture 192 when the guidewire is not extended through the aperture 192, as illustrated in FIGS. 119 and 121. As the guidewire is pushed through the guidewire aperture 192, the flaps of the valve 400 are forced apart to permit passage of the guidewire 130, as illustrated in FIG. 120.

It will be appreciated that the valve 400 could alternatively be provided in the form of four, two, or any other number of co-operating flaps.

Referring to FIGS. 122 to 127 the guidewire exit hole may be sealed with a thin flexible membrane 401 which can withstand any pressure differential across the filter but can be deformed by the guidewire tip to open the seal/membrane. Various options are possible such as those illustrated in FIGS. 123 to 126.

Figure 128:
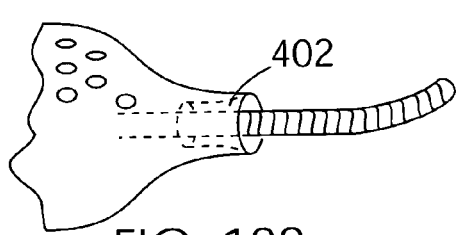
FIGS. 128 to 132 are various views of a filter with an alternative outlet seal.
Figure 129:
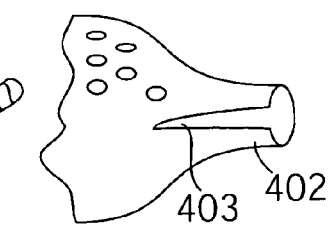
Figure 130:
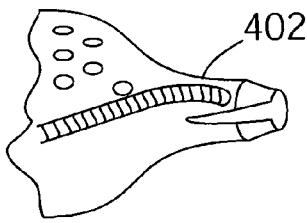
Figure 131:
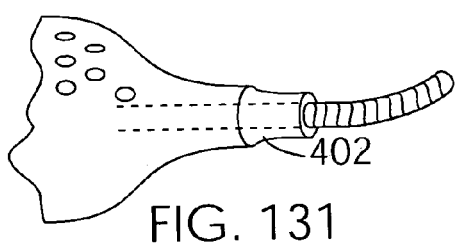
Figure 132:
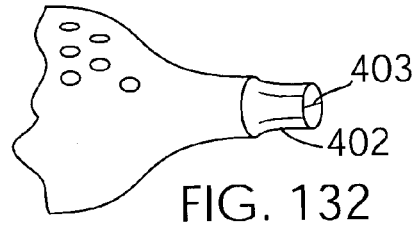

Another option is to provide a seal in the form of an invertible flexible tube 402. The tube may have slits 403 for additional flexibility. FIG. 128 shows an initial guidewire in position, FIG. 129 shows the wire removed and the tube collapsed, sealing the hole. In FIG. 130 a new wire is shown being advanced through the filter, the advancing of the wire pushing the tube out of the filter neck and forming a seal with the new wire as illustrated in FIG. 131. The tube may be slits or slots for added flexibility as illustrated in FIG. 132.

Figure 133:
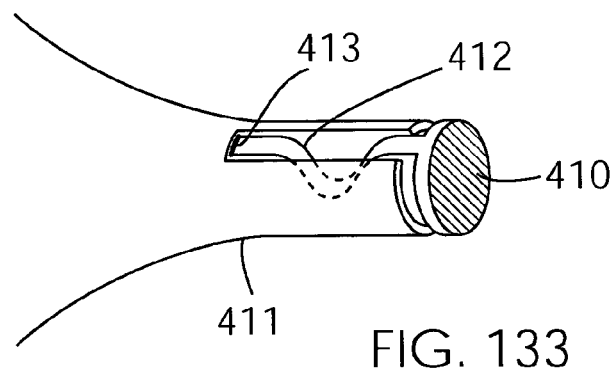
FIG. 133 is a perspective view of an alternative outlet seal.
Figures 134, 135:
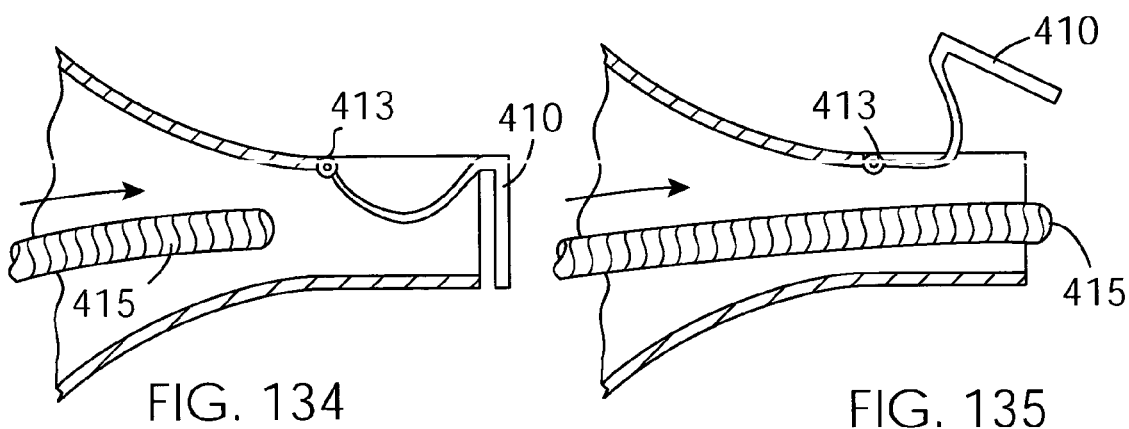
FIGS. 134 and 135 are cross-sectional views of the seal of FIG. 133, in use.

The guidewire exit hole may also be sealed by a flap valve or the like. Referring to FIGS. 133 to 135 a closure flap 410 is hingedly connected to the filter 411 by a curved lever 412. The hinge point 413 is stepped back proximally from the flap 410 so that the pressure drop across the flap 410 does not cause the flap 410 to open. The flap 410 is opened against the biasing of the lever 412 on insertion of a guidewire 415 as illustrated in FIGS. 134 and 135.

Figures 136, 137:
FIGS. 136 and 137 are perspective views of further outlet seals.

It will be appreciated that the hinge may have a range of different constructions. For example, as illustrated in FIG. 136 a hinge 416 may be provided by a flattened wire or a hinge 417 may be formed by a narrowing of the lever as illustrated in FIG. 137.

Figure 138:
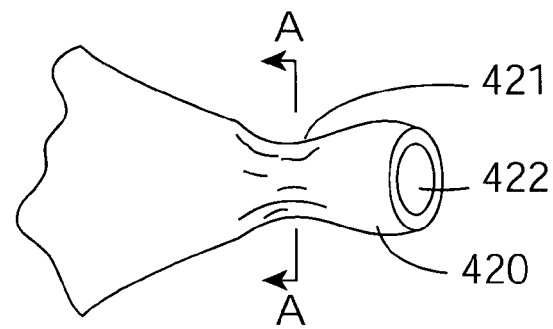
FIG. 138 is a perspective view of a further outlet seal.
Figure 139:
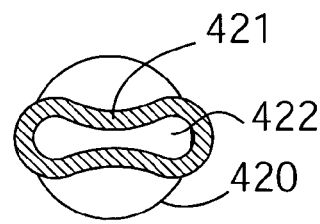
FIGS. 139 and 140 are cross-sectional views on the line A—A of FIG. 138 in different configurations of use.
Figure 140:
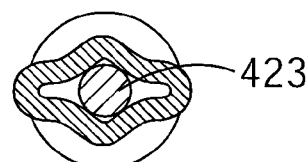

In another embodiment illustrated in FIGS. 138 to 140 a distal end 420 of a filter may have a flattened neck section 421 which normally seals a guidewire aperture 422 but which can be opened to facilitate passage of a wire 423.

Figure 141:
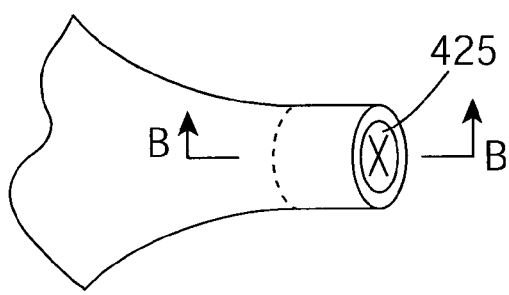
FIGS. 141 to 143 are views of a further outlet seal arrangement.
Figure 142:
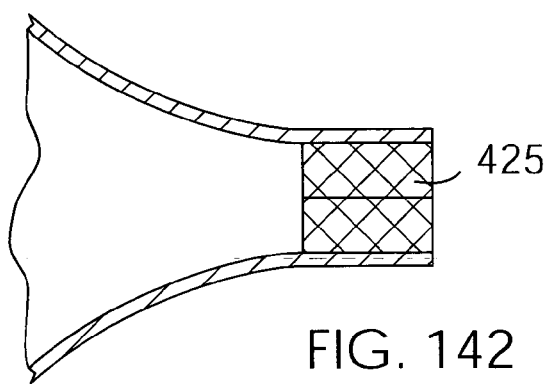
Figure 143:
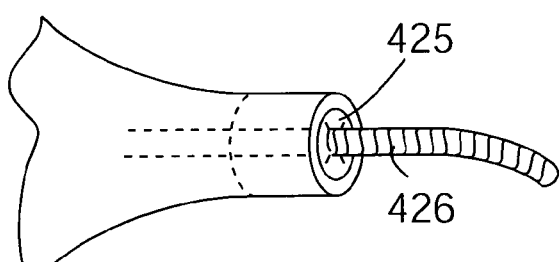
Figure 144:
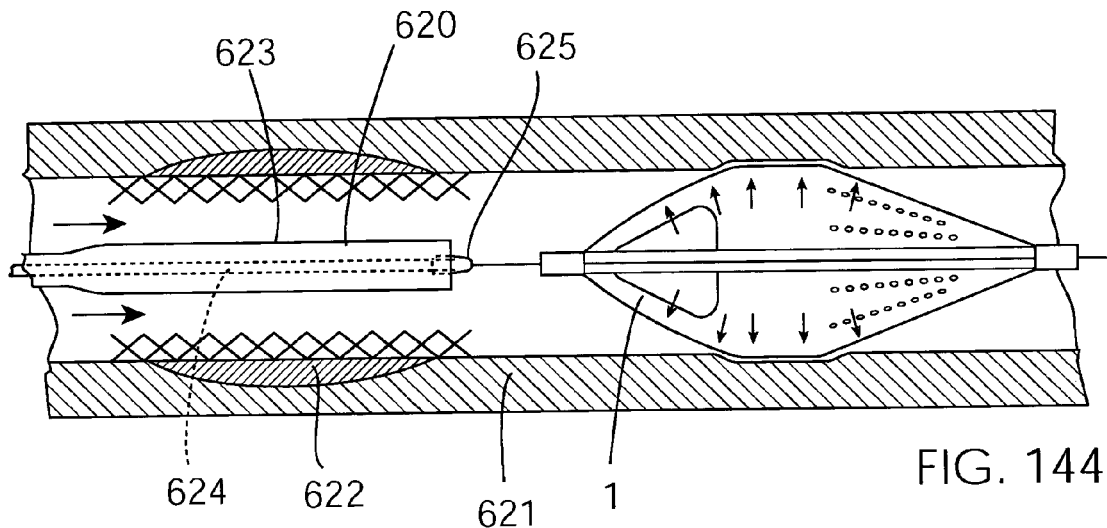
FIGS. 144 to 149 are partially cross-sectional side views illustrating retrieval of an embolic protection device.
Figure 145:
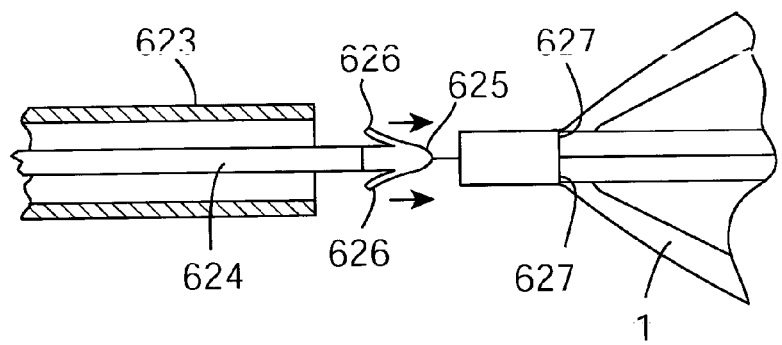
Figure 146:
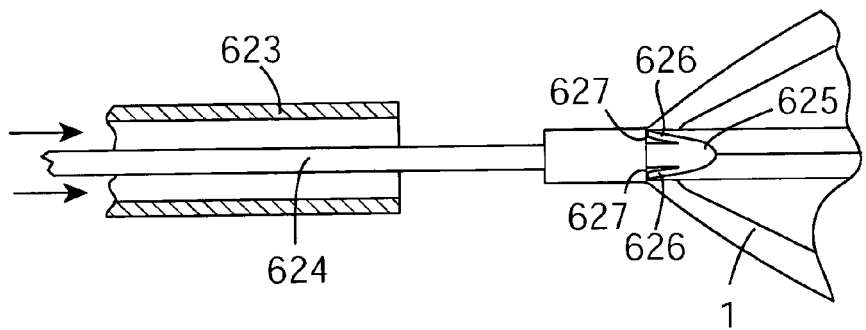
Figure 147:
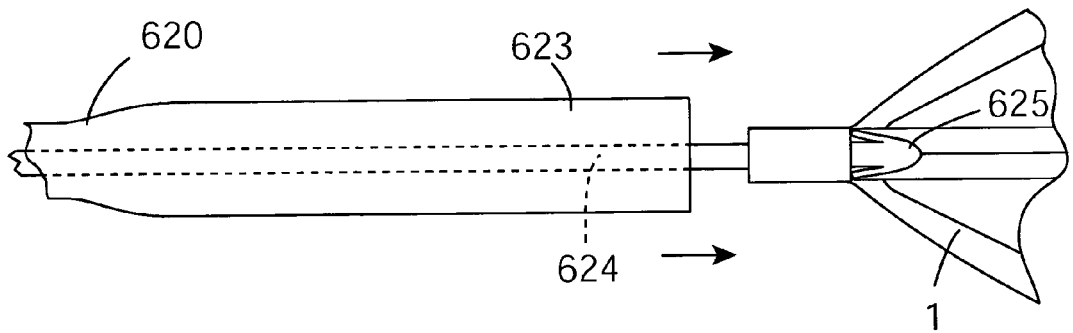
Figure 148:
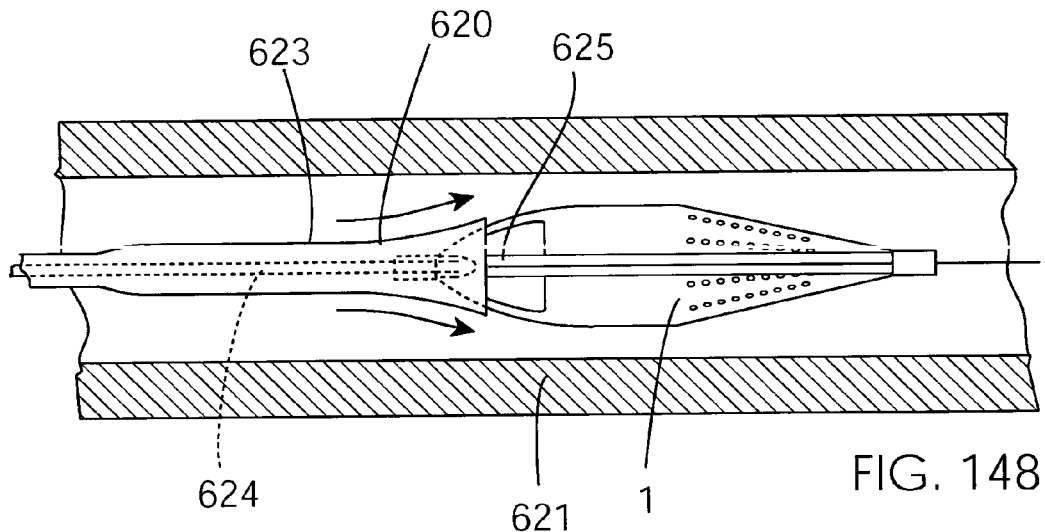
Figure 149:
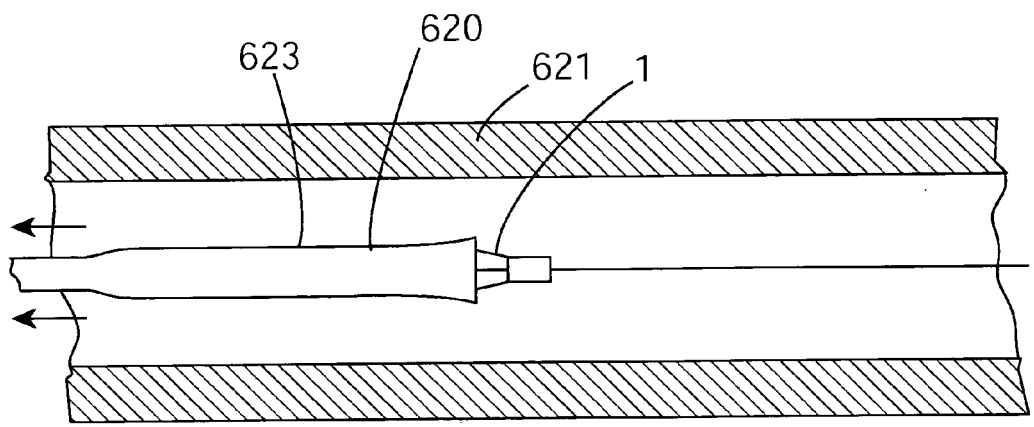
Figure 150:
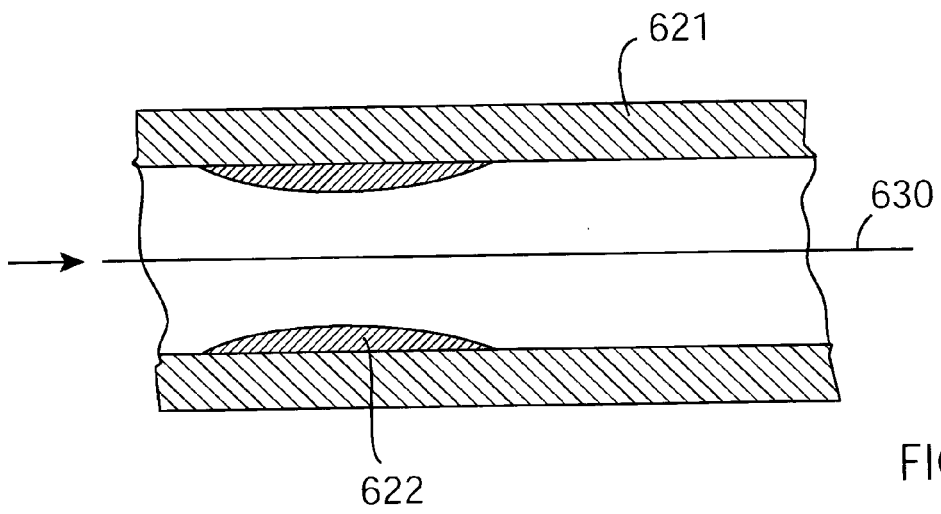
FIGS. 150 to 163 are partially cross-sectional, side views of an embolic protection filter and a retrieval catheter in use.
Figure 151:
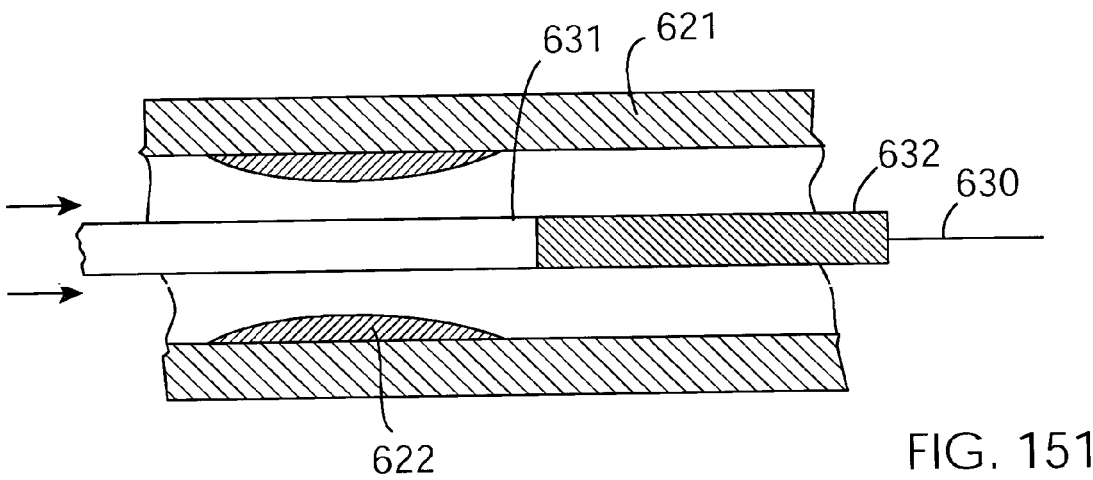
Figure 152:
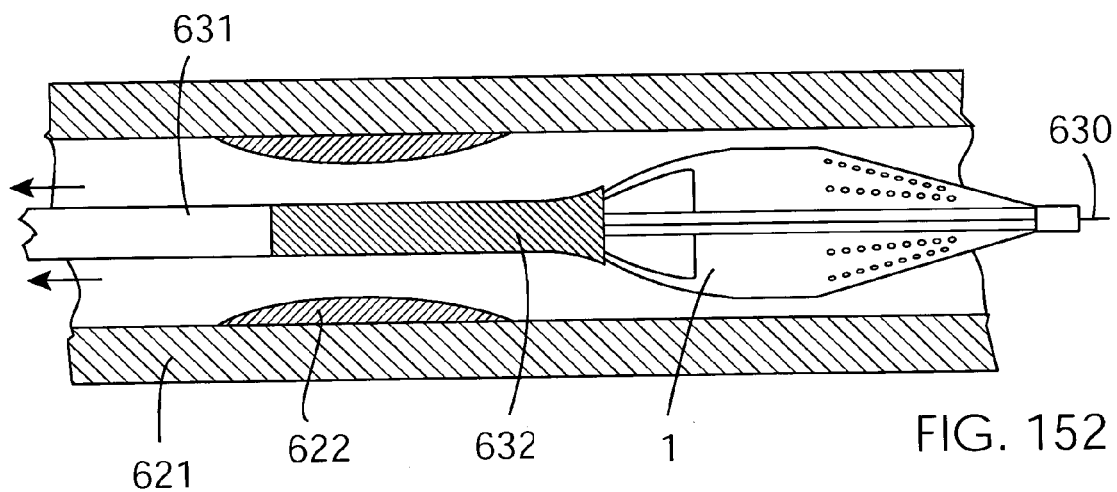

A further embodiment is illustrated in FIGS. 141 to 143 in which the filter distal guidewire aperture has a foam-like insert 425 with slits to facilitate deformation of the foam as a guidewire 426 is inserted whilst still maintaining a sealing engagement with the guidewire 426.

In the invention the retrieval device grips and retrieves the filter. Conventional filters are retrieved by using the guidewire to engage with the filter. This invention describes a retrieval device with one member which engages with and restrains the filter while a second member may envelop the filter. The retrieval device may function in the absence of a guidewire so that the filter can be retrieved even if the user has removed the guidewire and failed to replace it. This retrieval process may involve three stages: 1) Engage with the filter, 2) Decouple filter from vessel, 3) Retrieve the filter. Alternatively the retrieval may involve two stages: 1) Engage with the filter, 2) Retrieve the filter.

The retrieval process is simple and reliable. The snare (or loop or lasso) designs described provide one of the most reliable and versatile methods. There is preferably a feature on the filter with which this snare will engage easily. This feature and the snare loop are preferably radiopaque for ease of visibility and positioning. For example a large radiopaque ball (or shepherds crook) inside the filter may be pulled proximal to the filter when snared and wrapped down.

Referring in particular to FIGS. 144 to 149, there is illustrated a retrieval catheter 620 according to the invention. The retrieval catheter 620 is suitable for retrieving a filter, deployed in a vasculature 621 distally of a treatment location 622, such as a region of stenosis.

The catheter 620 comprises an outer catheter body 623 and a coaxial inner coupling member 624, the coupling member 624 having means for coupling to the filter especially a filter deployed in the vasculature 621 to be retrieved.

The coupling means is provided, in this case, by an arrow-head shaped tip 625 on the coupling member 624. The tip 625 has two male fingers 626 for engagement with two corresponding female recesses 627 on the filter 1.

The male fingers 626 are moveable between a low-profile configuration and an outwardly protruding configuration for engagement with the filter. In this case, the fingers 626 are of a resilient material, and are biased towards the outwardly protruding configuration.

During introduction of the retrieval catheter 620 through the vasculature 621, the tip 625 protrudes only partially distally of the distal end of the catheter body 623, so that the resilient fingers 626 are maintained in the low-profile configuration. The protruding tip 625 prevents snagging of the open mouth of the catheter body 623 against any protruding parts of the vasculature wall. In addition the tip 625 tapers distally inwardly for a smooth crossing profile.

When the retrieval catheter 620 has crossed the treatment location 622, the coupling member 624 is moved distally relative to the catheter body 623, to release the resilient fingers 626 to move to the outwardly protruding configuration. The coupling member 624 is then moved further distally into the filter until the fingers 626 engage with the recesses 627 of the filter.

The recesses 627 may be defined in a more pronounced manner by providing inwardly protruding steps or abutments on the proximal end of the filter support against which the fingers 626 may engage.

The catheter body 623 is next moved distally relative to the engaged filter 1 by maintaining the position of the coupling member 624, the distal end of the catheter body 623 is engaged with the proximal end of the filter body, the catheter body 623 is further advanced and thus the coupled filter 1 is collapsed down releasing the apposition force and is retrieved into the catheter body 623. When the collapsed filter 1 has been fully retrieved into the catheter body 623, the retrieval catheter 620 is withdrawn with the filter 1 from the vasculature 621.

The coupling member 624 of the retrieval catheter 620 enables a deployed medical device, such as the filter 1, to be retrieved into the retrieval catheter 620 with any retained embolic material within the filter 1 without requiring a step, or a clamp or any special stop features on the guidewire. Thus the retrieval catheter 620 enables the filter 1 to be used in combination with any standard guidewire.

In addition, it is not necessary to retract the guidewire to facilitate retrieval of the filter 1.

In certain circumstances if the guidewire was withdrawn from the deployed filter 1 it would still be possible to retrieve the filter 1 using the retrieval catheter of the invention. This could speed up the overall procedure. Also in some cases it may be difficult to recross the filter 1 with a guidewire. Furthermore by obviating the need to recross the filter 1 with a guidewire, the possibility of a spasm being caused is minimised.

FIGS. 150 to 163 illustrate the embolic protection filter 1 and the retrieval catheter 620 according to the invention, in use.

A guidewire 630 is introduced into and advanced through the vasculature 621 until the guidewire 630 crosses the desired treatment location 622. A delivery catheter 631 is then used to deliver the embolic protection filter 1 through the vasculature 621 over the guidewire 630, the filter 1 being housed within a distal pod 632 of the delivery catheter 631 in the collapsed configuration.

The filter 1 may in one case be loaded into a delivery catheter 631 as described in International patent applications Nos. PCT/IE01/00052 and PCT/IE01/00053, the relevant contents of which are incorporated herein by reference. It will be appreciated that other loading alternatives are also possible.

Figure 153:
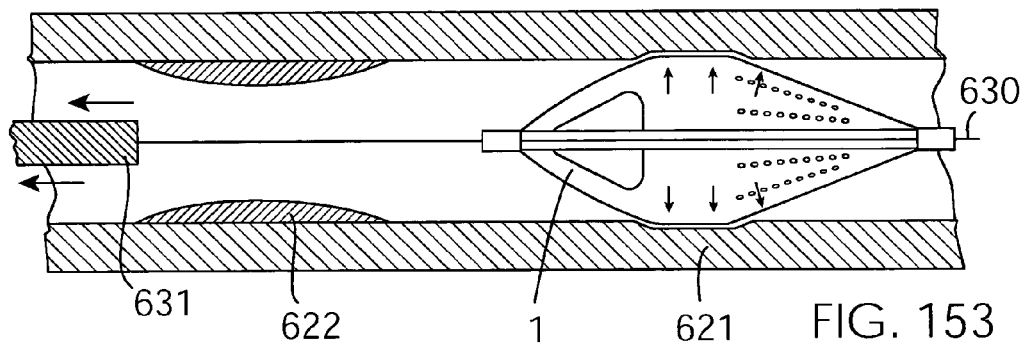
Figure 154:
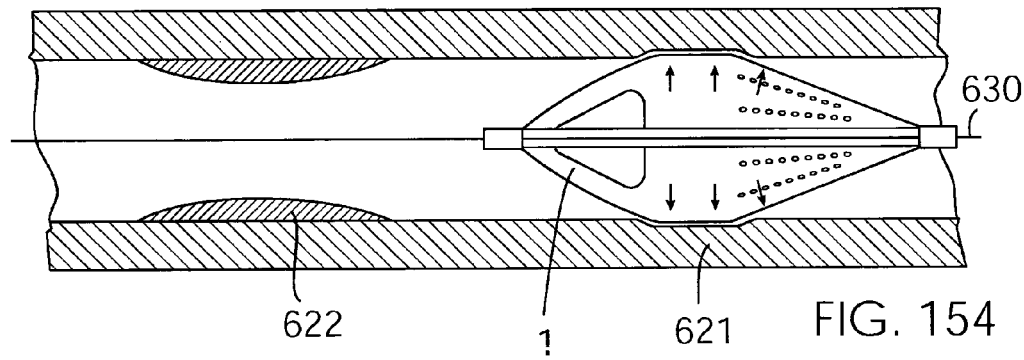
Figure 155:
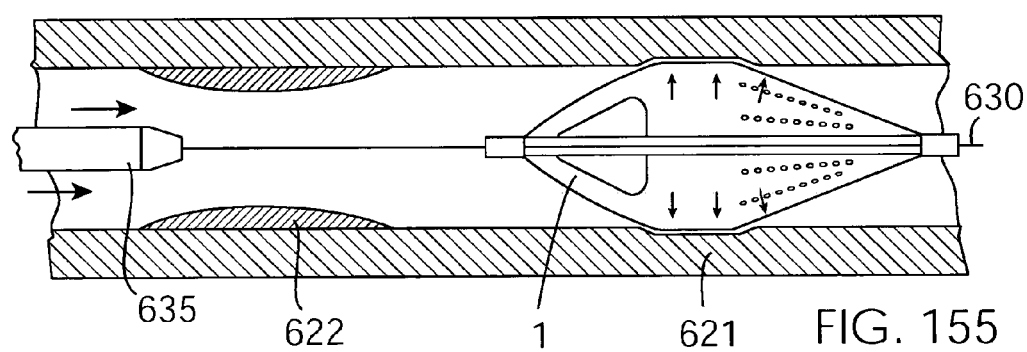
Figure 156:
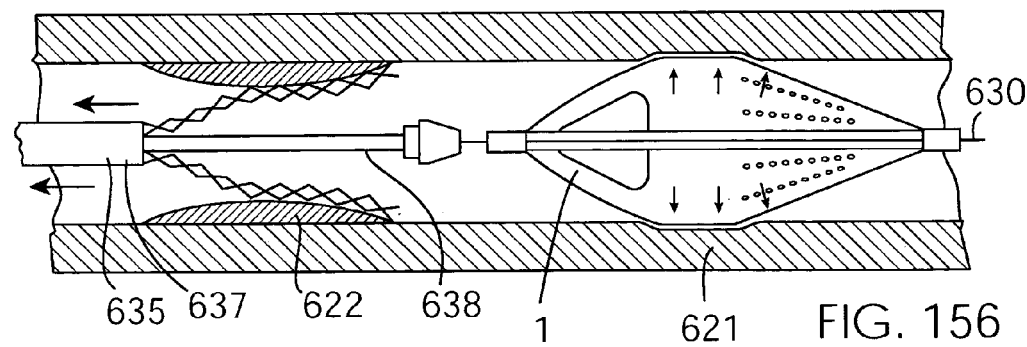
Figure 157:
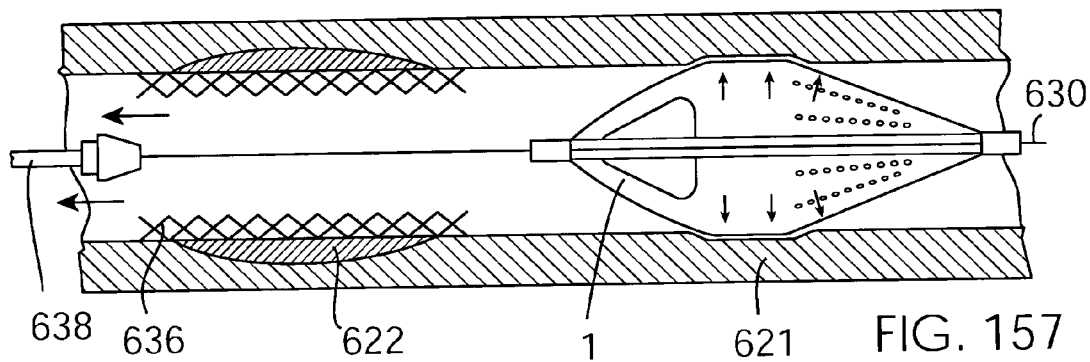
Figure 158:
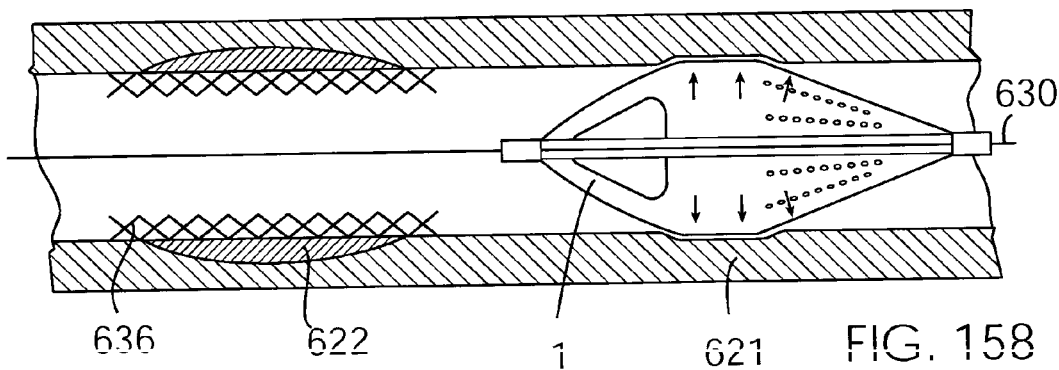
Figure 159:
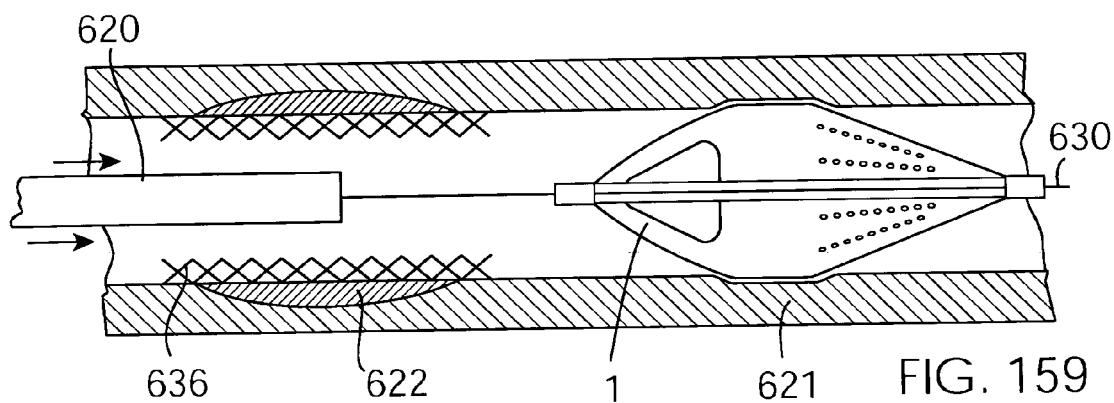
Figure 160:
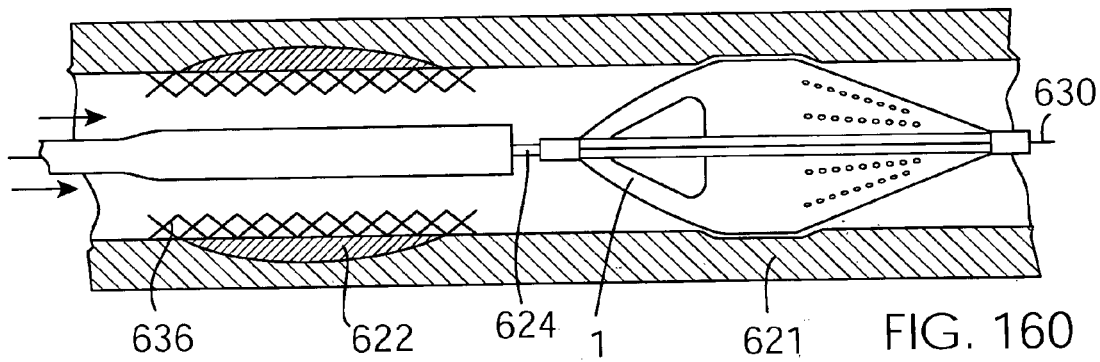
Figure 161:
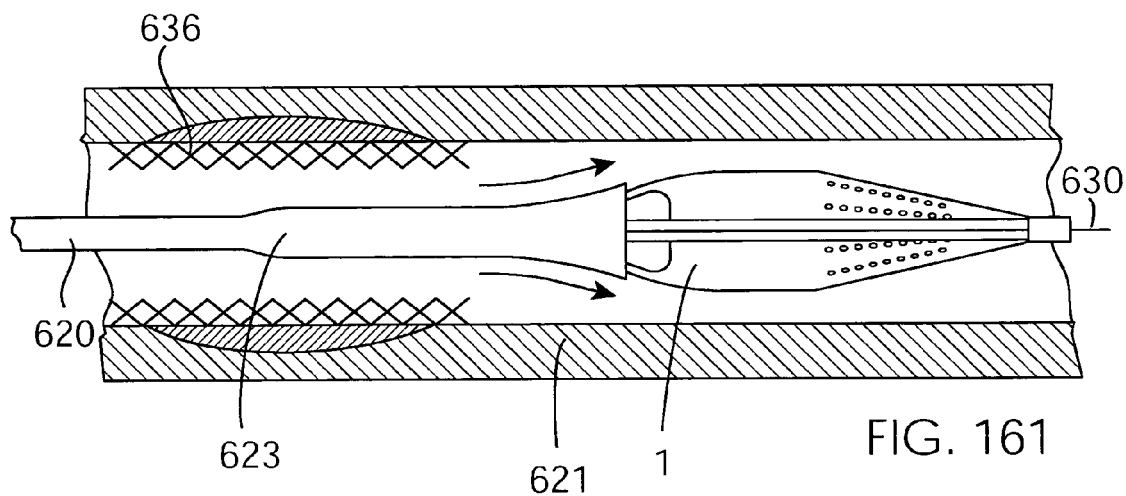
Figure 162:
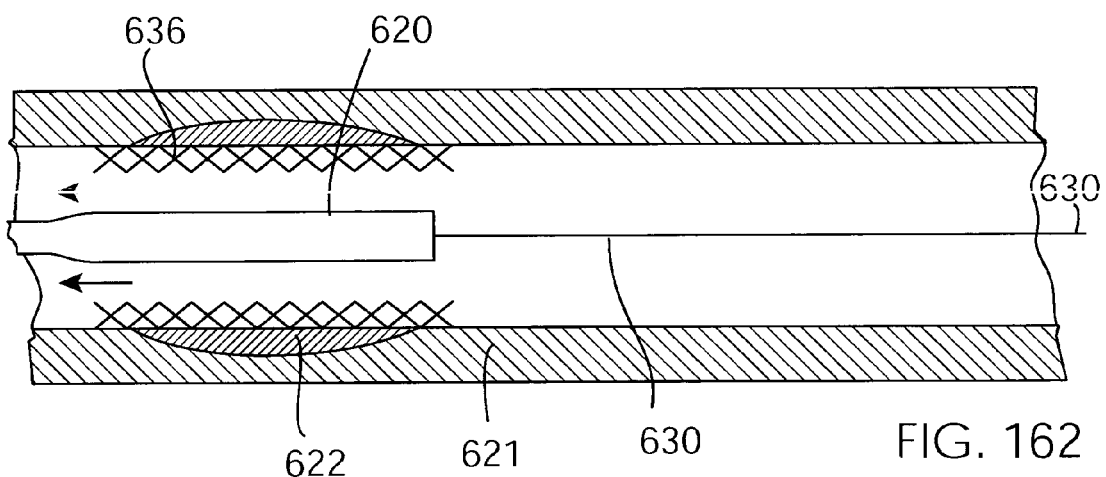
Figure 163:
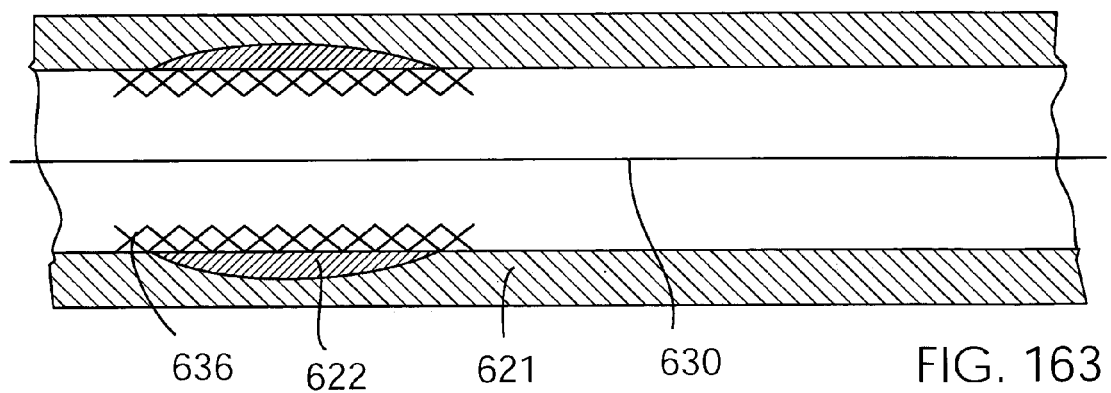

When the distal pod 632 has been advanced to a desired site distal to the treatment location 622, the pod 632 is moved proximally relative to an inner pusher to deploy the filter 1 out of the pod 632 into the outwardly extended configuration, as described in further detail in International patent applications Nos. PCT/IE01/00052 and PCT/IE01/00053. After complete deployment of the filer 1, the delivery catheter 631 is withdrawn from the vasculature 621 (FIG. 153).

In the outwardly extended configuration the filter 1 is in apposition with the vasculature 621, thereby preventing blood flow from bypassing the filter 1 between the filter 1 and the vasculature 621. The radial apposition force of the filter support against the filter body and the wall of the vasculature 621 retains the filter 1 in position against substantial longitudinal movement, even if the guidewire 630 is moved or indeed removed. In this way the filter 1 is prevented from migrating downstream in the vasculature 621.

An interventional procedure is then carried out at the treatment location 622. In the case illustrated, the interventional procedure is a stenting procedure using a self-expanding stent. However, a range of procedures are possible as alternatives to, or in addition to stenting, for example a balloon angioplasty procedure, a balloon-expandable stenting procedure, an atherectomy procedure, a lysis.

A stent delivery catheter 635 is used to deliver a stent, such as a self expanding stent 636, through the vasculature 621, the stent 636 being held in a collapsed configuration by a restraining sheath 637 of the stent delivery catheter 635.

When the stent delivery catheter 635 has been advanced to the treatment location 622, the sheath 637 is moved proximally relative to an inner body 638 of the catheter 635 to facilitate deployment of the stent 636 at the treatment location 622.

After complete deployment of the stent 636, the stent delivery catheter 635 is withdrawn from the vasculature 621, leaving the deployed filter 1 and the deployed stent 636 in the vasculature 621.

Any embolic material generated during delivery or deployment of the stent 636, or during withdrawal of the stent delivery catheter 639 is captured and safely retained in the deployed filter 1.

After completion of the interventional procedure, the retrieval catheter 620 is introduced into the vasculature 621, and advanced through the vasculature 621 until the stent 636 and the treatment location 622 have been crossed.

The filter 1 is simultaneously collapsed and retrieved into the catheter body 623 of the retrieval catheter 620 and with it the captured embolic material, by engaging the tip 625 with the filter 1, and then advancing the catheter body 623 distally over the coupling member 624 and the engaged filter 1.

Upon collapse of the filter 1, the apposition of the filter 1 with the vasculature 621 is released.

When the filter 1 has been fully collapsed and retrieved into the retrieval catheter 620, the retrieval catheter 620 with the collapsed filter 1 and retained emboli therein are withdrawn from the vasculature 621, leaving the deployed stent 636 in place at the treatment location 622 in the vasculature 621.

In this way, the filter 1 may be used to capture and safely remove any embolic material which has been generated during the interventional procedure.

An expandable balloon may be provided on the filter to enhance the outward radial force on the vasculature wall to retain the filter in position against substantial longitudinal movement. In use, the balloon may be inflated after deployment at the desired site in the vasculature to effectively anchor the filter in position. The balloon may be subsequently deflated before retrieval of the filter.

Figure 164:
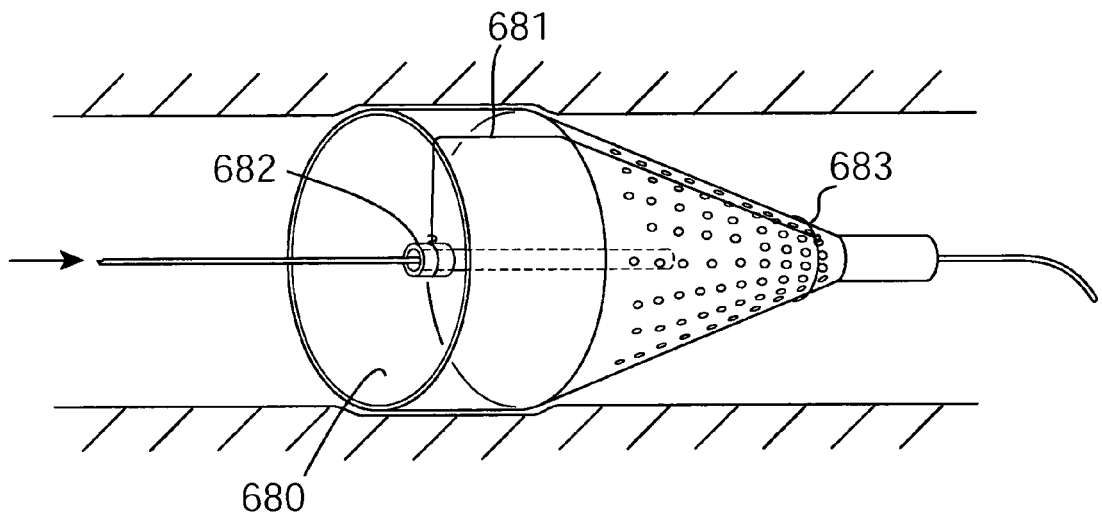
FIGS. 164 to 165 are partially cross-sectional, side views illustrating retrieval of another embolic protection filter according to the invention.
Figure 165:
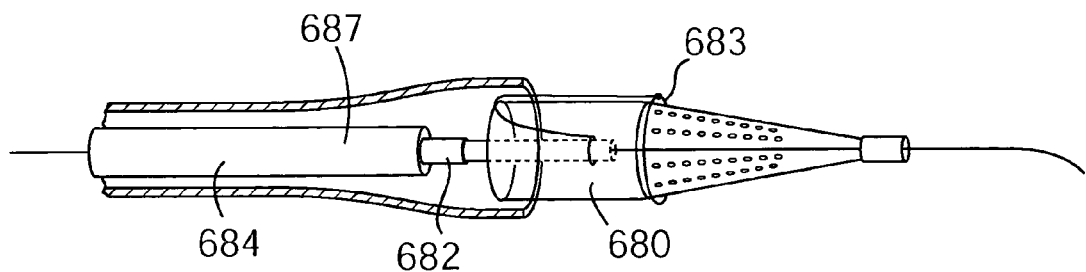

FIGS. 164 and 165 illustrate another embolic protection filter 680 according to the invention. The filter 680 comprises a capture tether 681 which extends externally of the filter body from a proximal ring 682, to which the tether 681 is fixed, to a distal capture hoop 683. The capture hoop 683 is located around the distal core at the outlet end of the filter 680 when the filter 680 is in the outwardly extended configuration, as illustrated in FIG. 164. The capture hoop 683 is slidable over the filter body. To collapse and retrieve the filter 680 into the retrieval catheter, the coupling member 684 engages the capture tether 681 and causes the capture hoop 683 to move proximally. The coupling member 684 may be engaged with the capture tether 681 using a hook, or loop, or any other suitable coupling means, as described previously. In this manner the filter 680 is compressed for retrieval into the catheter body 681, as illustrated in FIG. 165.

Figure 166:
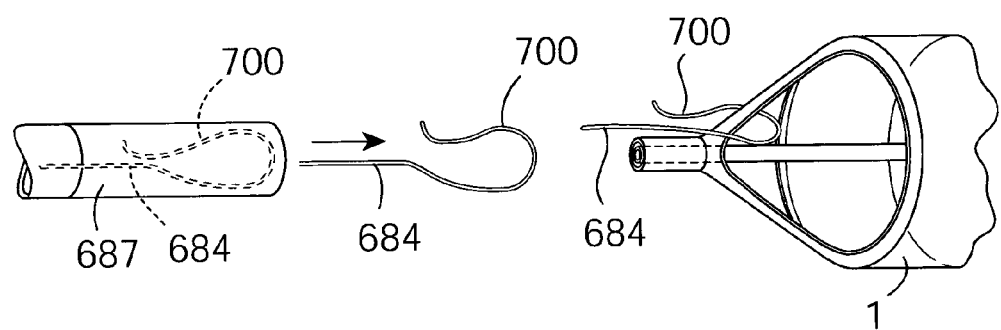
FIGS. 166 and 167 are schematic side views illustrating retrieval of an embolic protection filter using other retrieval catheters according to the invention.

The coupling means may alternatively be provided by a male member in the form of a hook 700, as illustrated in FIG. 166 for hooking around a receiver on the filter 1. The hook 700 may be used to couple the coupling member 684 to any suitably configured embolic protection filter.

Figure 168:
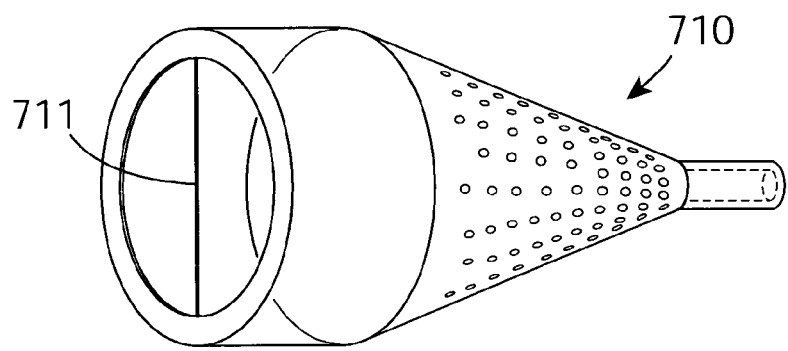
FIG. 168 is a perspective view of another embolic protection filter according to the invention.
Figure 169:
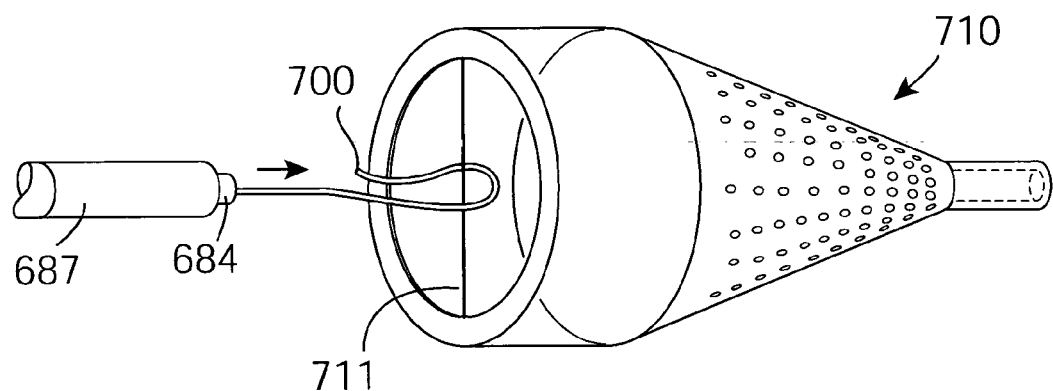
FIG. 169 is a perspective view illustrating retrieval of the filter of FIG. 168.

For example, an embolic protection filter 710, illustrated in FIGS. 168 and 169, has a tether arm 711 at a proximal end of the filter 710 around which the hook 700 may be extended to couple the deployed filter 710 with the coupling member 684 and thereby facilitate retrieval of the filter 710 into the catheter body 687.

FIGS. 170 to 173 illustrate further embolic protection devices 720, 725, 730 according to the invention.

Figure 170:
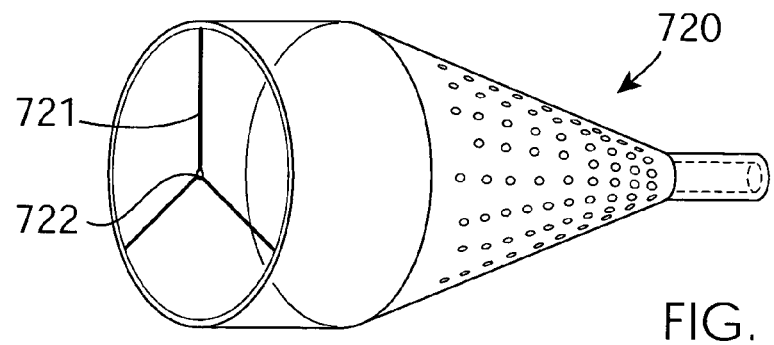
FIG. 170 is a perspective view of another embolic protection filter according to the invention.
Figure 171:
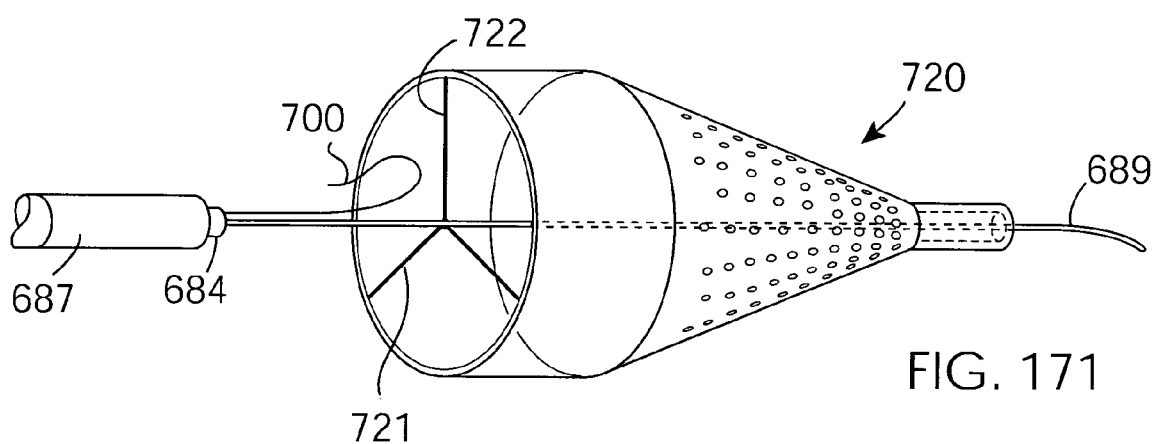
FIG. 171 is a perspective view illustrating retrieval of the filter of FIG. 170.

The filter 720 of FIG. 170 has three tether arms 721 which extend radially inwardly from the filter body to meet at a central point 722. The hook 700 may be extended around any one of the tether arms 721 to couple the coupling member 684 to the filter 720. This tether arrangement enables the filter 720 to be retrieved with a central, axial pull force.

Figure 172:
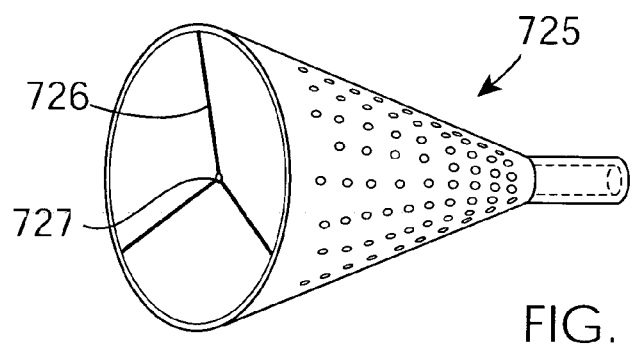
FIGS. 172 and 173 are perspective views of further embolic protection filters according to the invention.

In the filter 725 of FIG. 172, the three tether arms 726 extend radially inwardly and distally to the central point 727. In this manner the central point 727 is stepped back distally from the single, large inlet opening to minimise the possibility of embolic material becoming caught or hung up on the tether arms 726.

Figure 173:
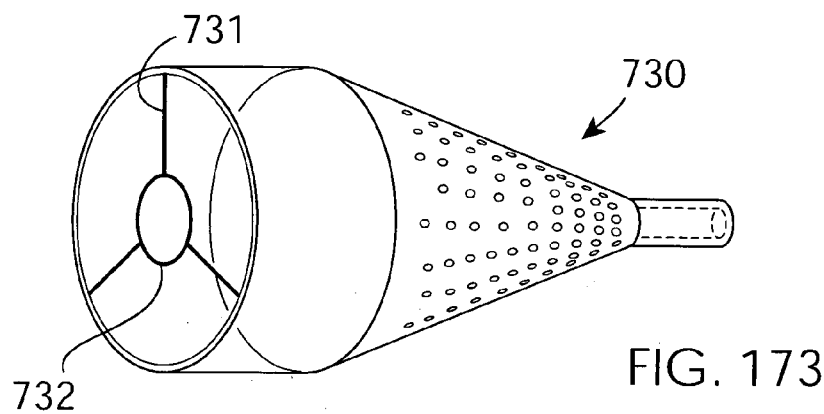
Figure 174:
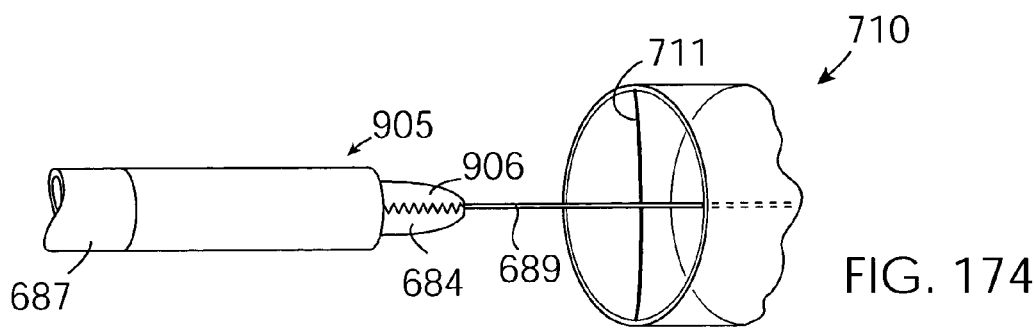
FIGS. 174 to 178 are schematic views illustrating retrieval of the embolic protection filter of FIG. 168.
Figure 175:
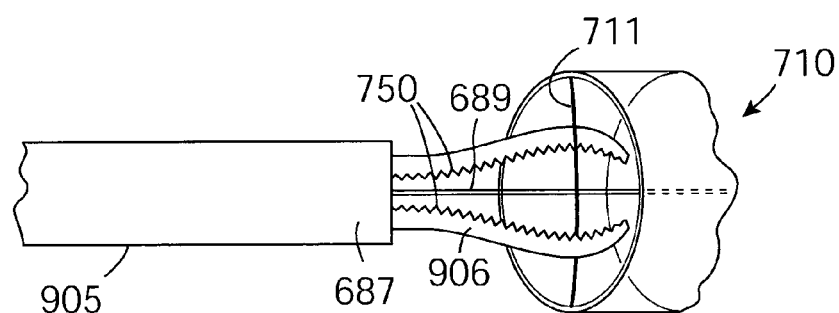
Figure 176:
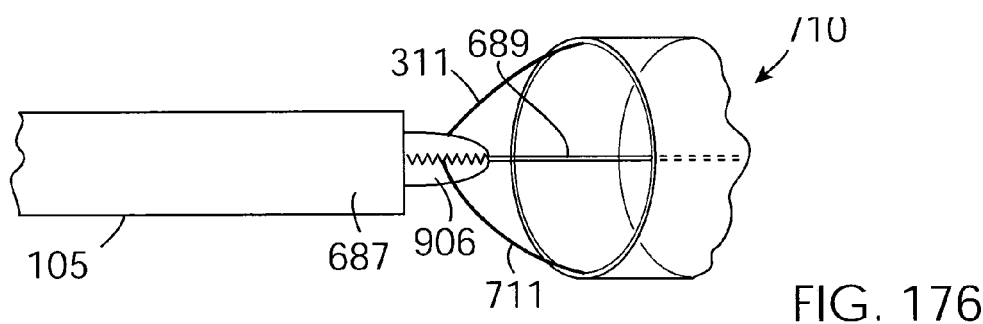
Figure 177:
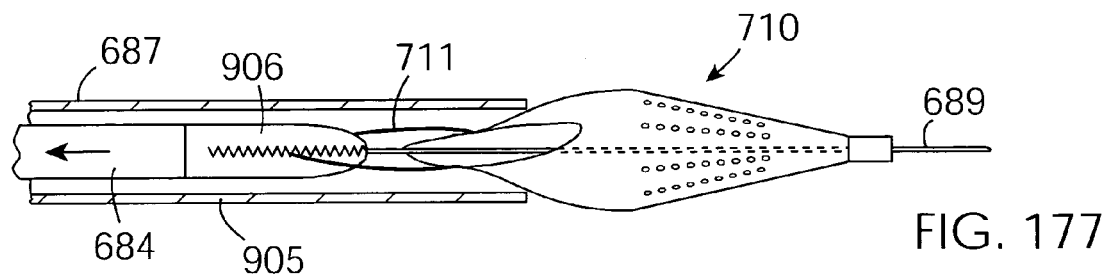
Figure 178:

The filter 730 of FIG. 173 has a central ring 332 to which the tether arms 331 are fixed.

FIGS. 174 to 178 illustrate the embolic protection filter 710, being retrieved into the catheter body 684 using grasping jaws 906. In this case, the jaws 906 comprise serrated edges 750 to achieve a secure grasping of the tether arm 711. In this manner, the filter 710 may be coupled to the coupling member 684 and retrieved into the catheter body 687. The retrieval catheter 905 is withdrawn from the vasculature after retrieving the filter 710 leaving the guidewire 689 remaining in the vasculature.

The tether arms of any of the above described embodiments may be mechanically attached at the central point, and/or at the central ring, and/or to the filter body, for example by bonding, or welding, or brazing. Alternatively the tether arms may be provided integral with the mesh/membrane of the filter body. The tether arms could also be provided as a fibre from such a mesh.

Figure 179:
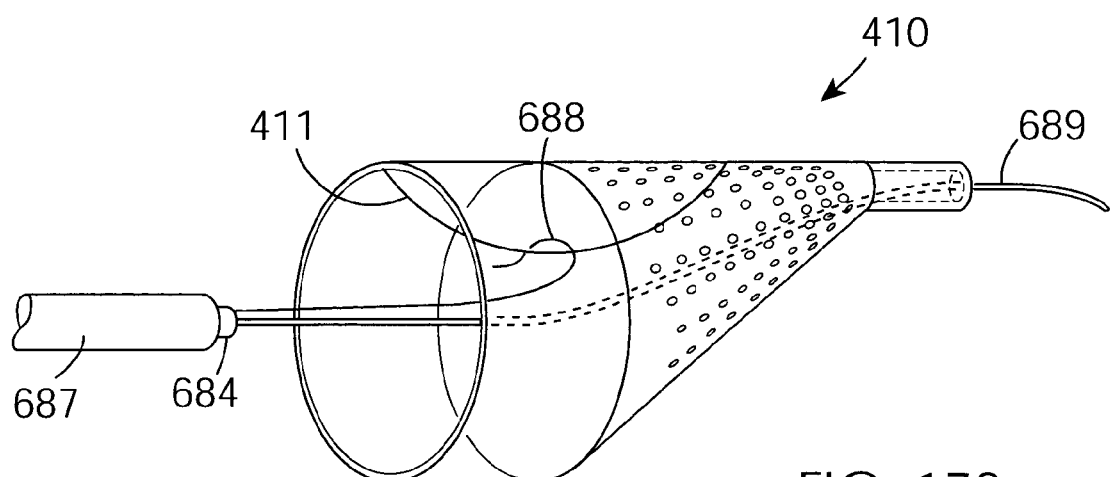
FIGS. 179 and 180 are perspective views of further embolic protection filters according to the invention.

In the embolic protection filter 410 of FIG. 179 the tether arm 411 is located within the filter 410. To couple the coupling member 684 to the filter 410, the hook 688 is extended into the filter 410 and hooked around the tether arm 411.

Figure 180:
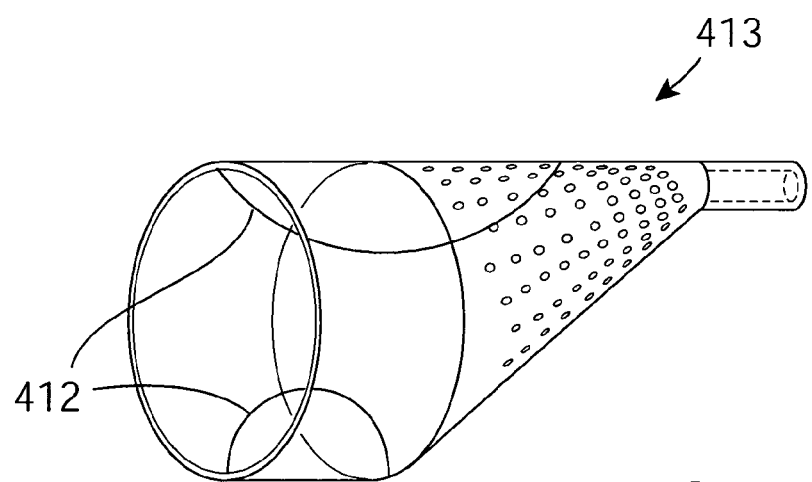

In the filter 413 of FIG. 180, two tether arms 412 are provided. It will be appreciated that any suitable number of tether arms may be provided at either end of an embolic protection filter, and/or within the filter.

Figure 181:
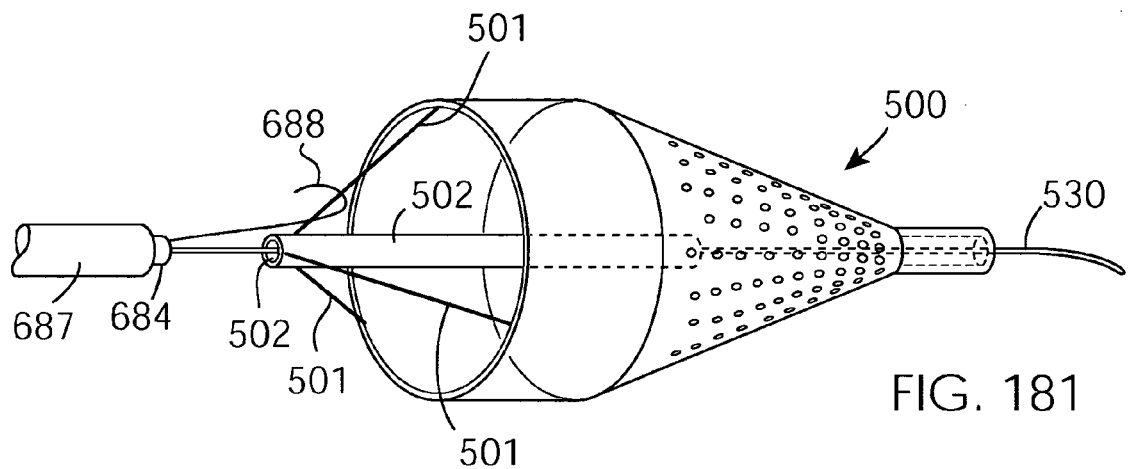
FIGS. 181 and 182 are perspective views illustrating retrieval of another embolic protection filter according to the invention.
Figure 182:
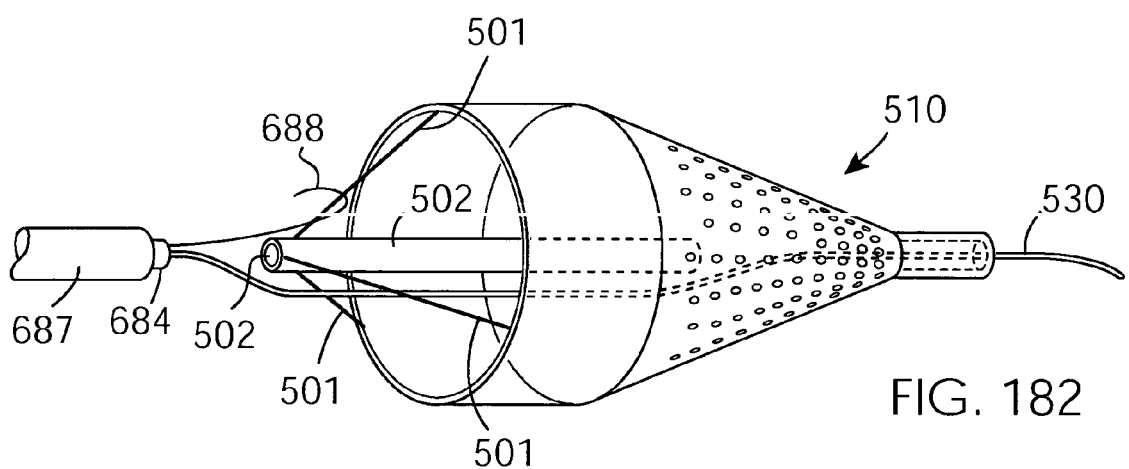

Referring to FIGS. 181 and 182, there is illustrated another embolic protection filter 500 according to the invention.

In this case, the filter 500 comprises an inner tubular member 502 to which the three tether arms 501 are fixed. The tubular member 502 defines a guidewire lumen 503 therethrough for passing a guidewire 530 through the tubular member 502 (FIG. 181).

The tubular member 502 extends through only part of the filter 500. As illustrated in FIG. 182, this enables the guidewire 530 to cross the filter 500 without having to thread the guidewire 530 through the relatively small diameter guidewire lumen 503.

This configuration may be particularly advantageous when it is desired to cross the filter 500 with a guidewire while the filter 500 remains deployed in a vasculature. In this circumstance, the distal end cone of the filter body may act as a guide to guide the guidewire 530 through the guidewire aperture 112.

Figure 183:
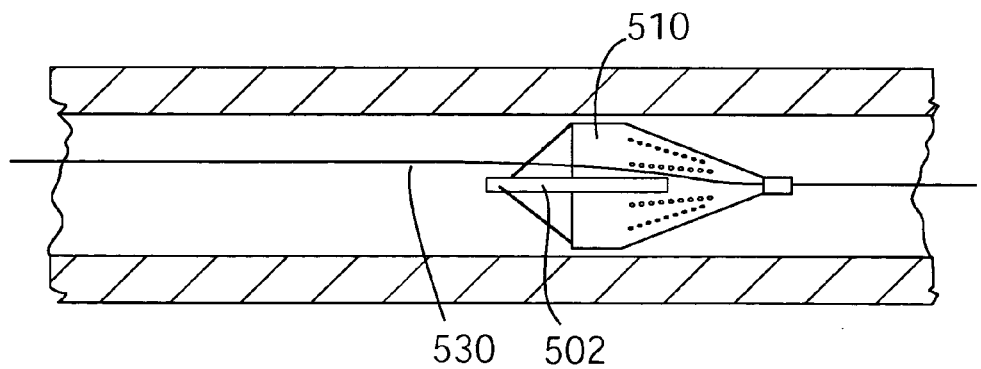
FIG. 183 is a perspective view of another embolic protection filter deployed in a vasculature.
Figure 184:
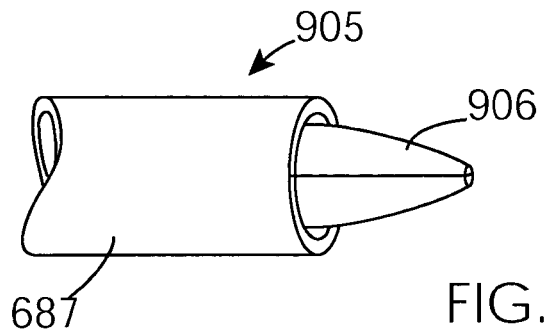
FIG. 184 is a side view of part of another retrieval catheter according to the invention.
Figure 185:
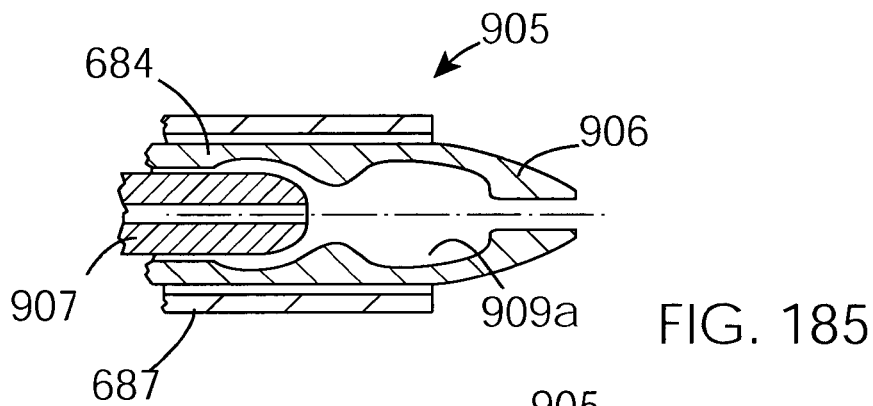
FIG. 185 is a cross-sectional, side view of the retrieval catheter of FIG. 184.

The tubular member 502 of the embolic protection filter 510 illustrated in FIG. 183 also extends only partially through the filter 510 to facilitate crossing of the filter 510 with the guidewire 530 without requiring threading of the guidewire 530 through the tubular member 502.

It will be appreciated that any other suitable means for coupling the deployed filter 1 with the coupling member 684 of the retrieval catheter may be employed to facilitate retrieval of the filter 1 into the catheter body 687, for example the coupling member 684 may be provided with one or more female recesses for engagement with one or more corresponding male protrusions on the filter 500.

Figure 167:
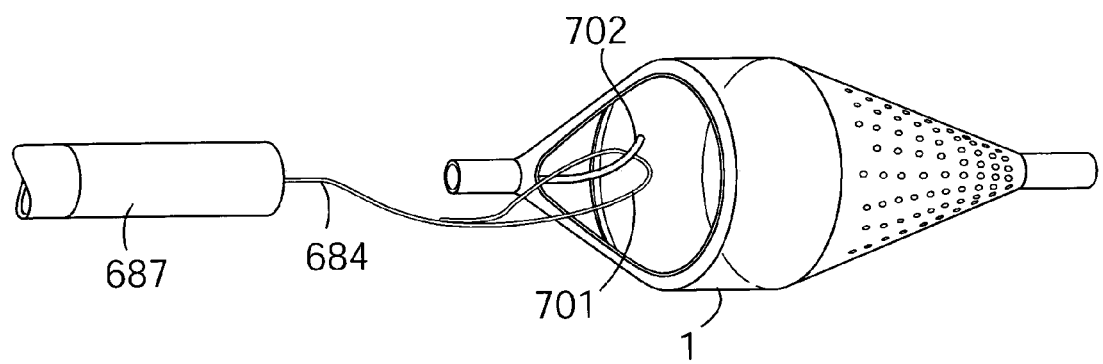

Alternatively a female member on the coupling member 684 may be provided in the form of a loop 701, as illustrated in FIG. 167, for looping around a male stub 702 protruding from the filter 1.

Referring to FIGS. 184 to 189 there is illustrated another retrieval catheter 905 according to the invention. In this case, the coupling member 684 comprises a pair of jaws 906 at the distal end of the coupling member 684. The jaws 906 are movable between an outwardly protruding configuration (FIG. 186) and a low-profile configuration (FIG. 187) to grasp the filter 1.

Figure 186:
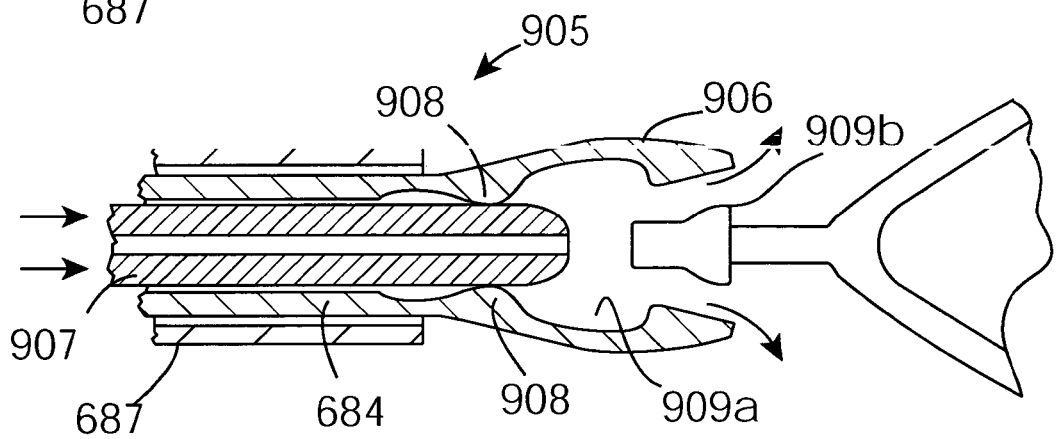
FIGS. 186 to 188 are schematic side views illustrating retrieval of an embolic protection filter using the retrieval catheter of FIG. 184.

The jaws 906 are biased towards the low-profile configuration and may be moved outwardly by moving an inner elongate actuator 907 longitudinally distally relative to the jaws 906 to engage elbows 908 on the jaws 906 and thereby move the jaws 906 outwardly in a camming arrangement (FIG. 186).

Figure 187:
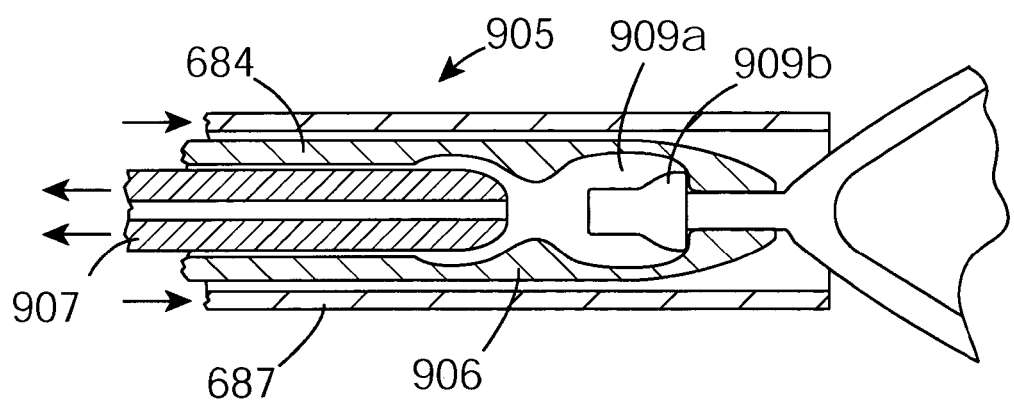

The jaws 906 define a recessed portion 909a for co-operation with a protruding neck 909b on the proximal end of the filter during grasping of the filter, as illustrated in FIG. 187.

In use, the retrieval catheter 905 is advanced through the vasculature in the low-profile configuration until the jaws 906 are proximally adjacent to the deployed filter 1. The actuator 907 is then moved distally relative to the jaws 906 to cam the jaws 906 open, and the opened jaws 906 are advanced until the recessed portion 909a of the jaws 906 are around the protruding neck 909b of the filter. By moving the actuator 907 proximally relative to the coupling member 684 the jaws 906 are released to move inwardly to grasp the filter 1 around the neck 909b. The grasped filter may then be retrieved into the catheter body 687 by moving the catheter body 687 distally relative to the coupling member 684.

Figure 188:
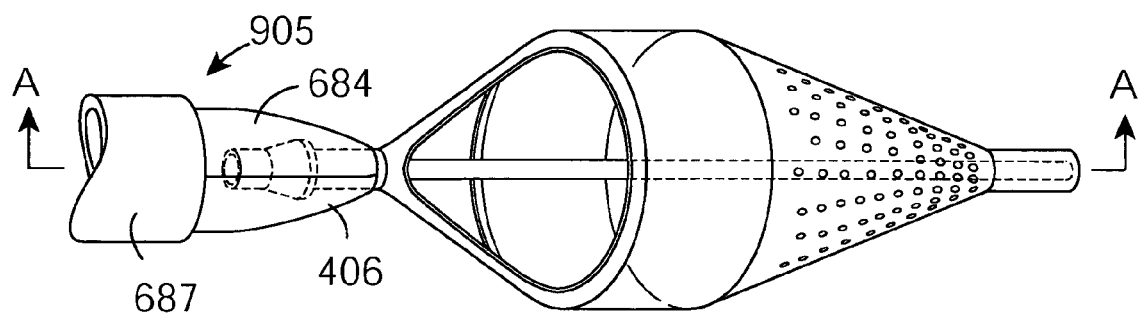
Figure 189:
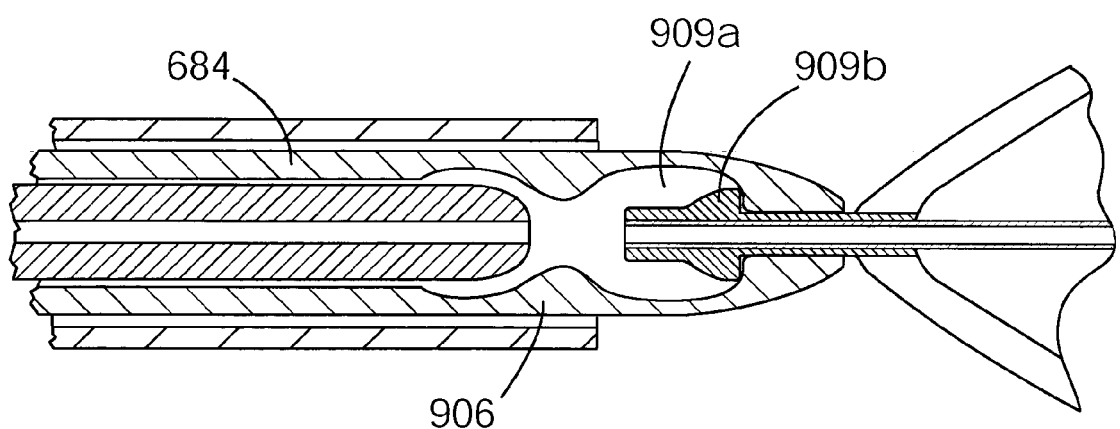
FIG. 189 is a side view along line A—A in FIG. 188.

It will be appreciated that the jaws 906 may grasp any suitable part of the filter to facilitate retrieval. For example, the jaws 906 may grasp the filter at the inlet openings, as illustrated in FIGS. 188 and 189.

As illustrated in FIGS. 190 to 191, the jaws 906 may alternatively be biased outwardly. During advancement of the retrieval catheter 905 through the vasculature, the jaws 906 are restrained in the low-profile configuration by the catheter body 687 (FIG. 190). To move the jaws 906 outwardly, the coupling member 684 is moved distally relative to the catheter body 687 to release the jaws 906 to spring outwardly (FIG. 191).

To subsequently move the jaws 906 inwardly when the recessed portion 909a of the jaws 906 are around the protruding neck 909b of the filter 1, the catheter body 687 is moved distally relative to the coupling member 684 to engage the jaws 906 and move the jaws 906 inwardly to grasp the filter around the neck 909b. The filter is then retrieved into the catheter body 687 by advancing the catheter body 687 further distally relative to the coupling member 684 and the grasped filter (FIG. 192).

Alternatively, the coupling member 684 may have a magnetic tip 686 for magnetic coupling to an oppositely charged magnetic portion of the filter 1.

Figure 193:
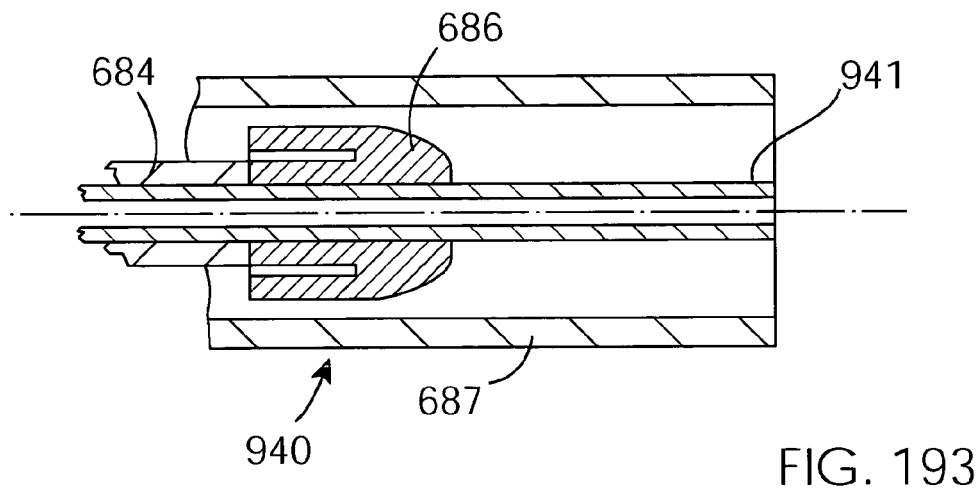
FIG. 193 is a cross-sectional, side view of part of another retrieval catheter according to the invention.
Figure 194:
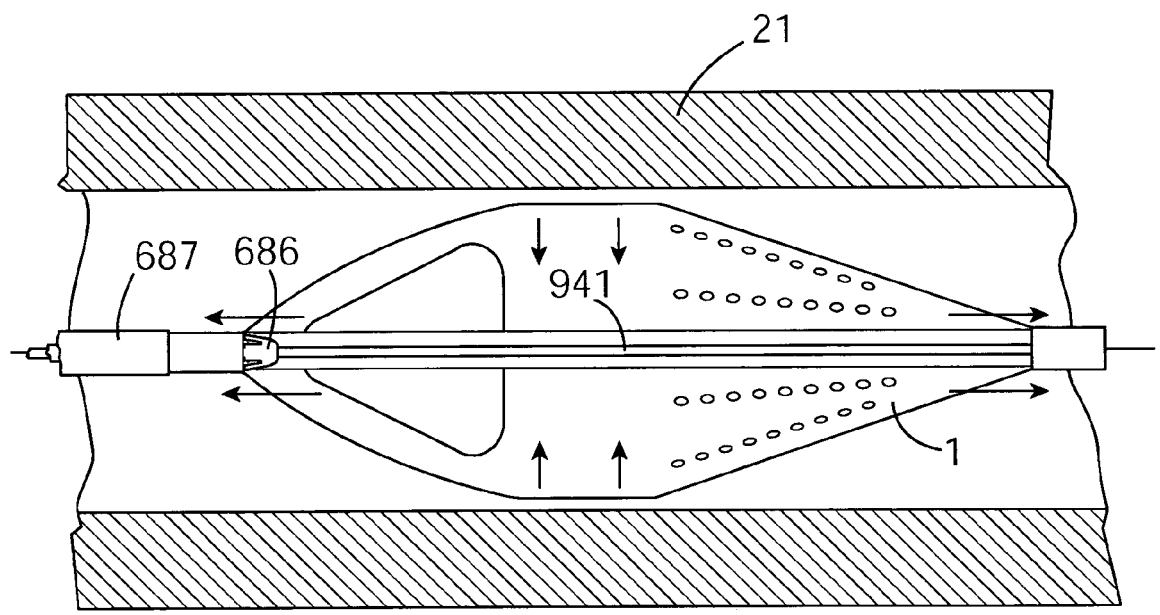
FIG. 194 is a partially cross-sectional, side view illustrating collapse of an embolic protection filter using the retrieval catheter of FIG. 193.
Figure 195:
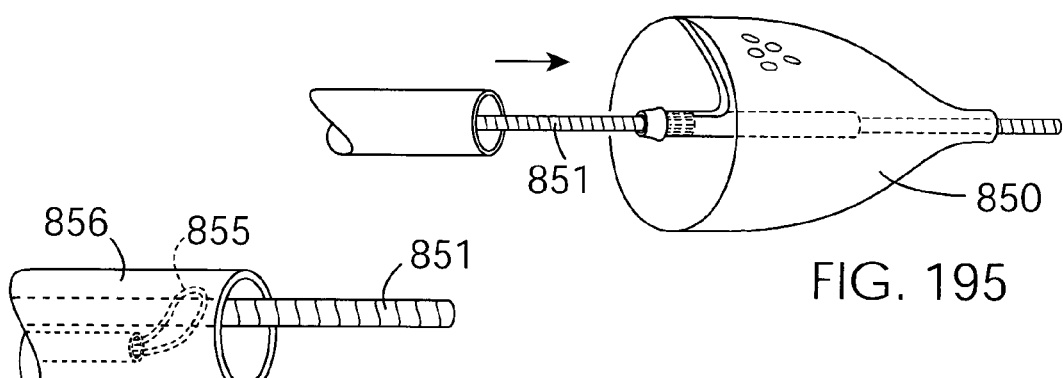
FIGS. 195 to 201 are various views illustrating the snaring of an embolic protection device of the invention.
Figures 196, 197:
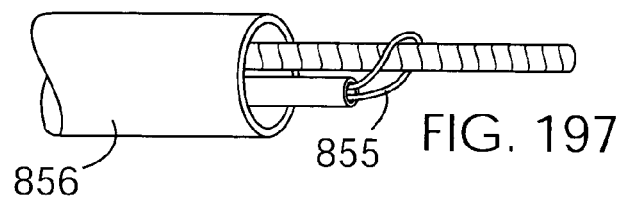
Figure 198:
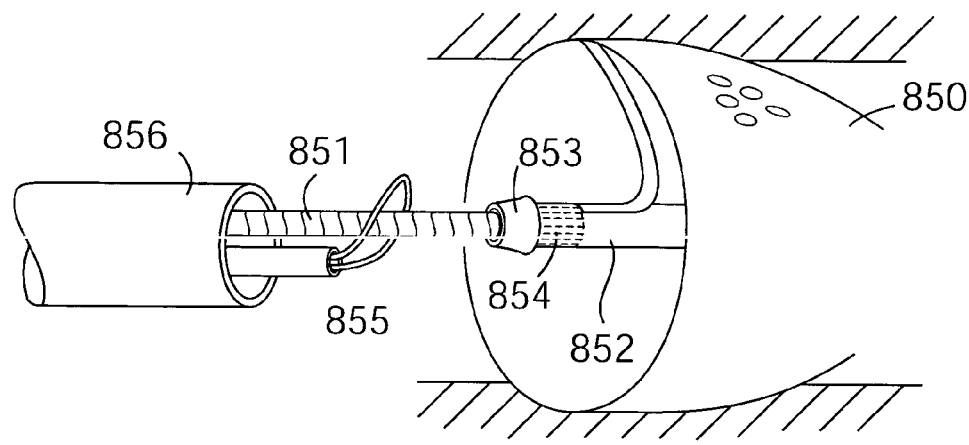
Figure 199:
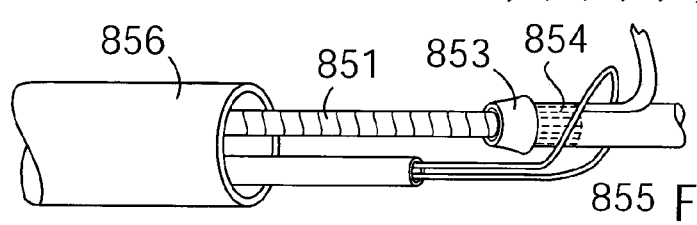
Figure 200:
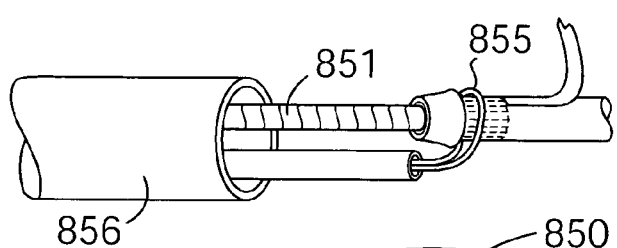
Figure 201:
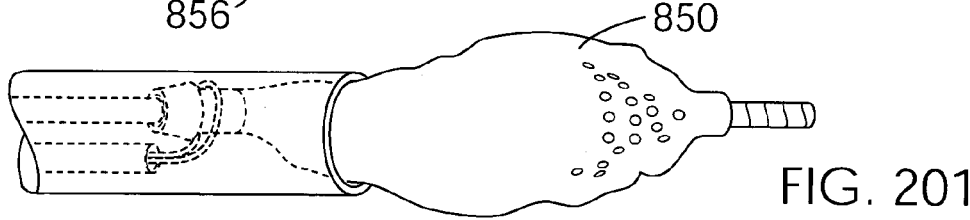
Figures 202, 203, 204, 205, 206:
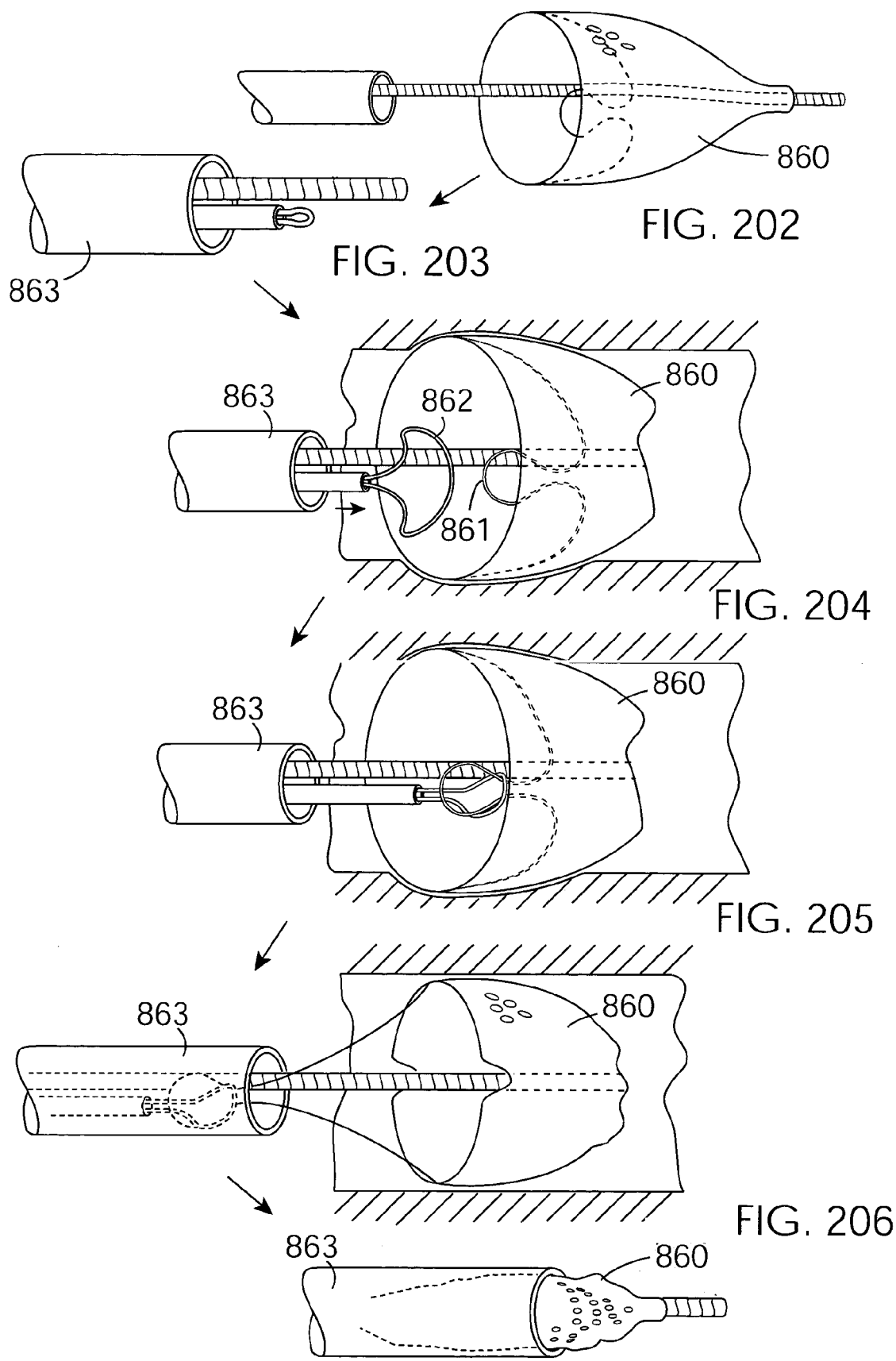
Figure 207:
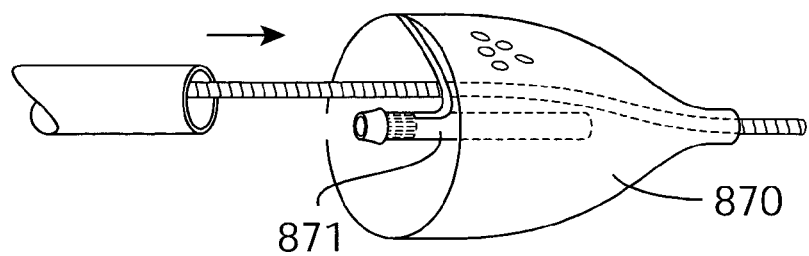
FIGS. 207 to 212 are various views illustrating snaring of a further filter.
Figure 208:
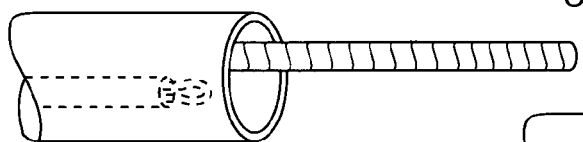
Figure 209:
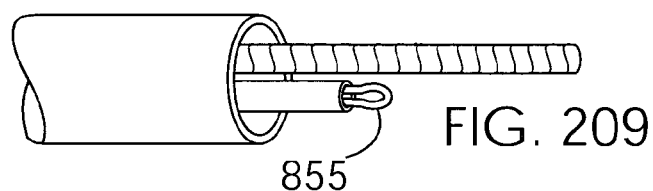
Figure 210:
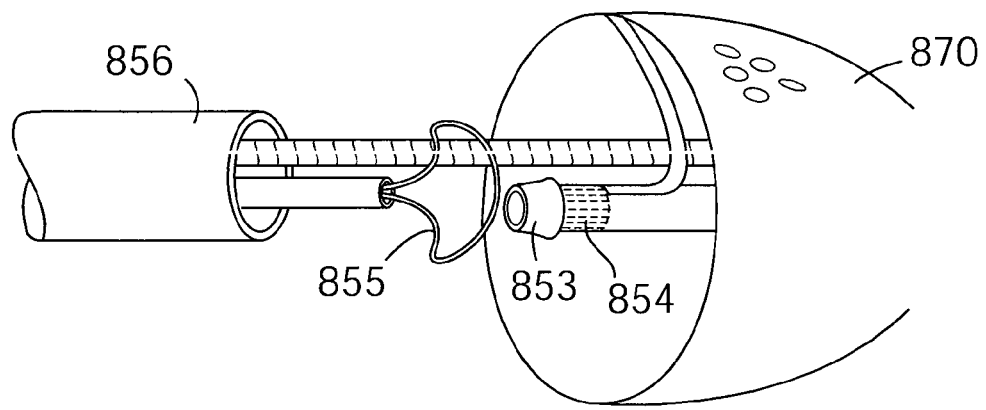
Figure 211:
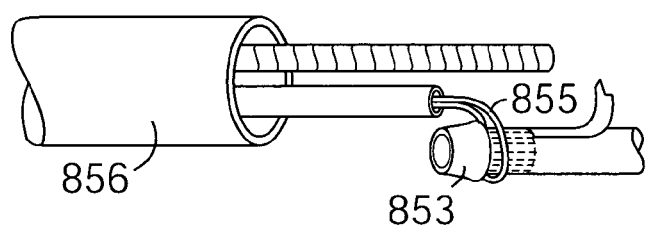
Figure 212:
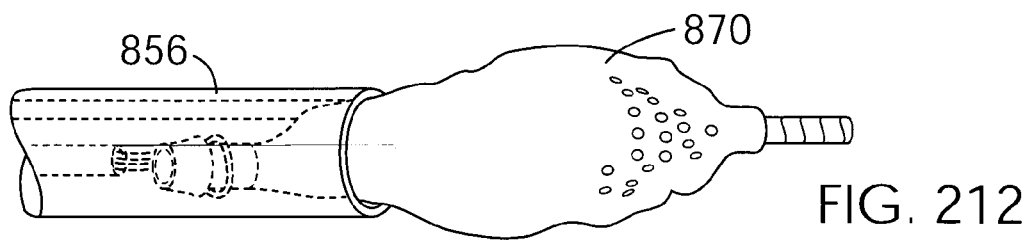
Figures 219, 220:
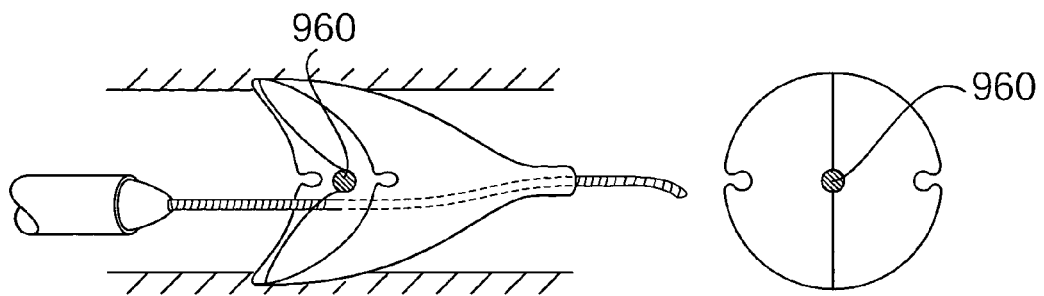
FIGS. 219 to 224 are views of the snaring of a filter of the invention.
Figure 221:
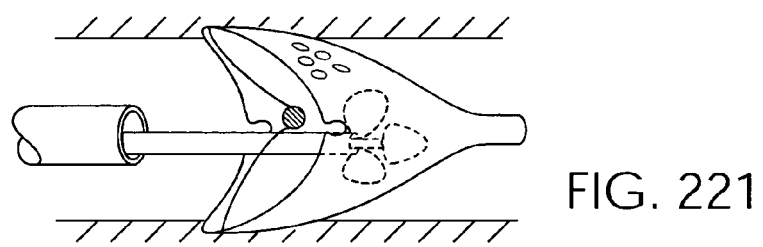
Figure 222:
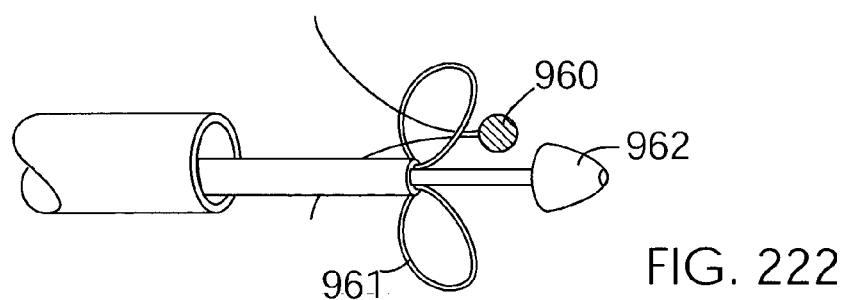
Figure 223:
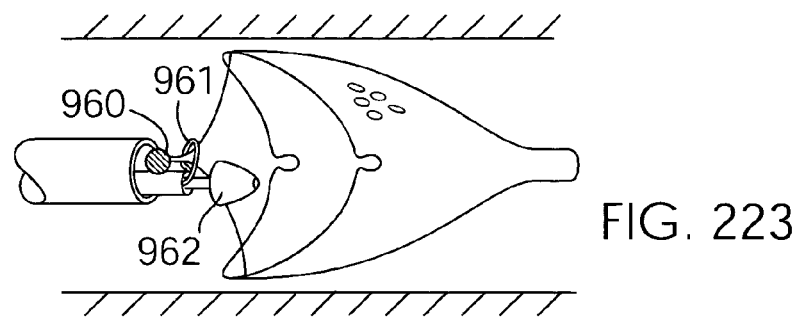
Figure 224:
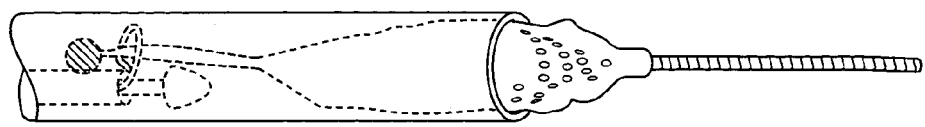
Figure 233:
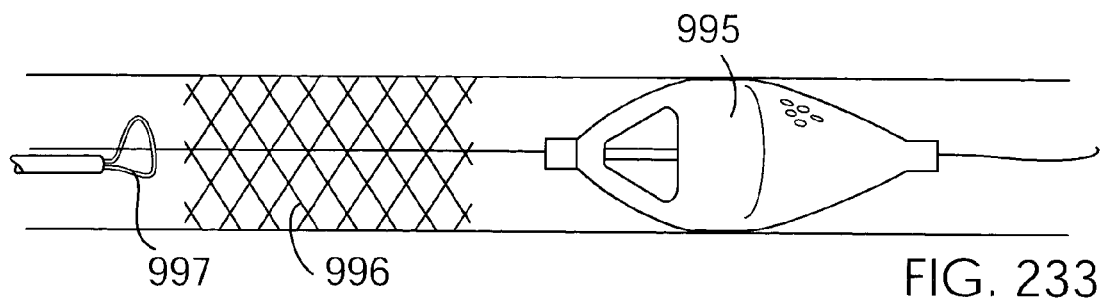
FIGS. 233 to 237 are side, partially cross-sectional views of the snaring of any filter.
Figure 234:
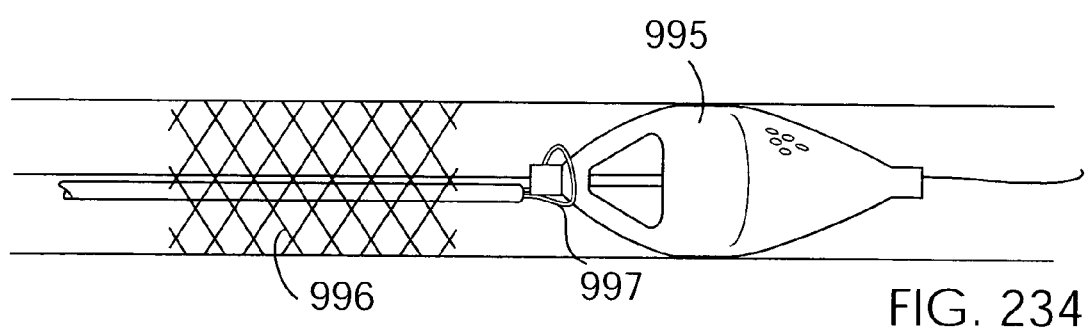
Figure 235:
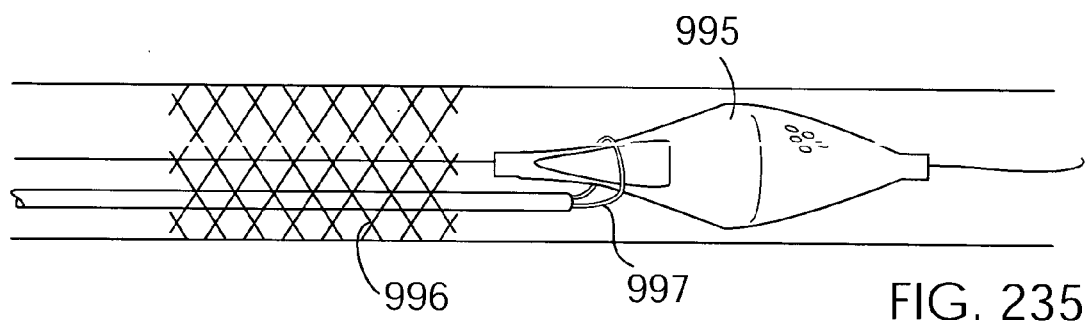
Figure 236:
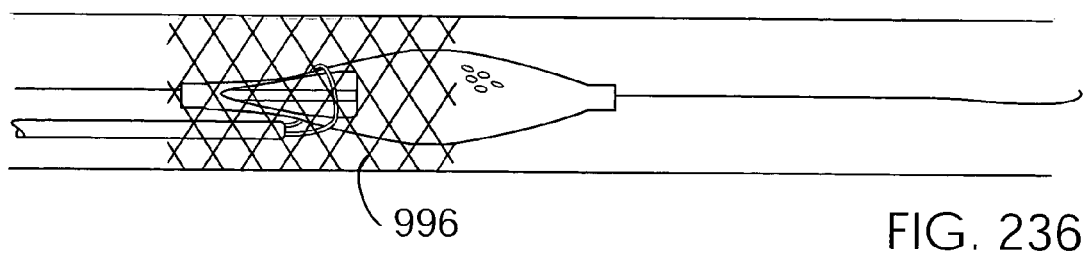
Figure 237:
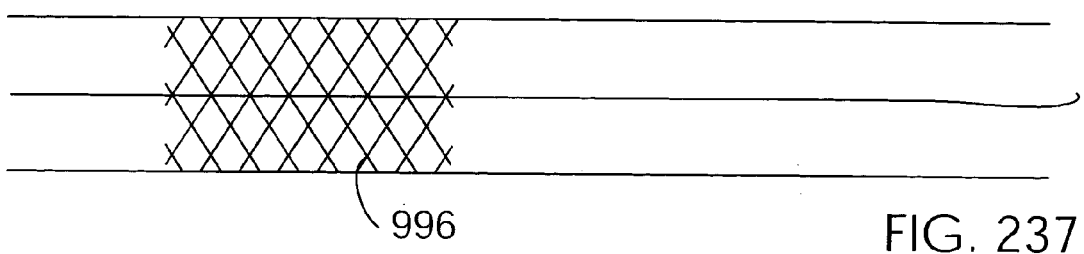

FIGS. 193 and 194 illustrate another retrieval catheter 940 according to the invention. In this case, the retrieval catheter 940 comprises a second coupling member 941, which is movable relative to the first coupling member 684. In this way, the second coupling member 941 may be used to axially elongate an element of the deployed filter, such as the filter support frame, to collapse the filter to the low-profile configuration for retrieval into the catheter body 687. In this case, the second coupling member 941 acts as a pusher and is movable distally relative to the tip 686. By engaging the tip 686 with the filter support and then moving the second coupling member 941 distally to engage a distal end of the filter support, the filter support is axially elongated and the filter is collapsed from the outwardly extended configuration of FIG. 194 to the collapsed configuration.

The collapsed filter may then be retrieved by moving the catheter body 687 distally relative to the tip 689 and the engaged filter.

Referring to FIGS. 195 to 201 there is illustrated another filter retrieval system of the invention. In this case a snare type retrieval is used for a filter 850 with a guidewire 851 extending through a tubular member 852. The tubular member 852 has a projecting head portion 853 with an associated marker band 854 for engagement by a lasso or loop 855 delivered through a retrieval catheter 856 into which the filter is retrieved as illustrated.

Another embodiment is illustrated in FIGS. 202 to 206 which is used for retrieval of a filter 860 which does not have a tubular member. In this case the filter frame has a snare receiving projection 861 which is engaged by a snare lasso/loop 862 and the filter 860 is retrieved into a retrieval catheter 863, as illustrated.

FIGS. 207 to 212 illustrate an embodiment in which a filter 870 is used which has a partial tubular member 871 but the guidewire does not extend through the tubular member. This arrangement is similar to that of FIGS. 195 to 201 above and like parts are assigned the same reference numerals. The snare loop is in this case free of the guidewire and may be more easily manipulated. In both cases the snare loop may be rendered radiopaque to facilitate snaring with the filter for retrieval.

Further retrieval devices are illustrated in FIGS. 213 to 218 in which the retrieval devices have arms 950 which open out when an outer sheath 951 is retracted and thus create a large inlet mouth which can readily trap the filter frame, particularly if radiopaque features such as marker bonds are used. When the arms 950 are in position distal to the snare feature of the frame/filter the arms are closed again, for example by re-advancing a sheath 951 which collapses the arms 950 and traps tether feature 952 of the filter, for example behind a step or tooth on the arm(s).

Referring to FIGS. 219 to 224 the filter frame may have a retrieval feature such as a nodule 960 which may be engaged by a suitable snare such as a snare loop or lasso 961 which is then tightened or simply pulled back to collapse the frame and retrieve the filter. The centering tip 962 may be used to assist guiding of the snare loop.

Various alternative filter designs with an integral snare feature are possible. For example, in FIGS. 225 and 226 the filter frame has a projecting arm 970 which may be engaged by a snare.

An expandable engagement member 971 may be used to catch a drawstring type arrangement 972 (FIGS. 227, 228) or to catch internal wires/tethers/fibers/strings of the filter (FIGS. 229, 230).

Referring to FIGS. 231 and 232 there is illustrated the size of a snare 990 to snare a filter 991. The snare engagable features of the filter in this case are provided by indents 992 in the support arms over which the snare loop 990 is engaged.

The snaring of a filter of any type is illustrated in FIGS. 233 to 237. In this case the filter 995 is positioned distal to a stent 996 and a snare loop 997 is advanced through the stent to engage the filter as illustrated, allowing the filter to be at least partially collapsed for retrieval.

Figure 238:
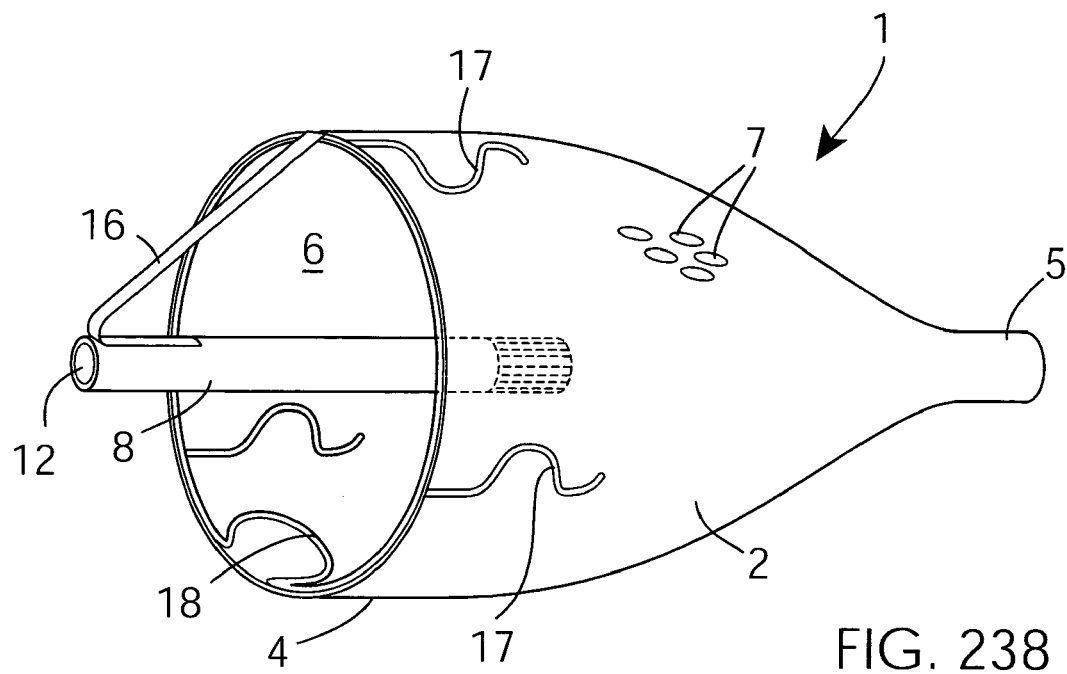
FIGS. 238 and 239 illustrate the snaring of another filter.
Figure 239:
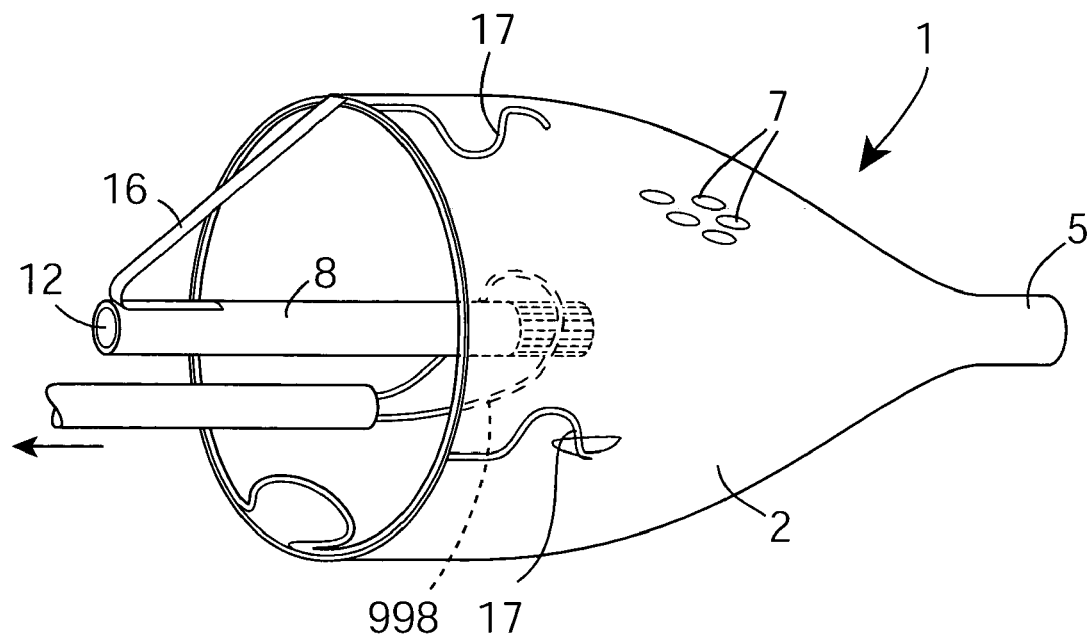

In FIGS. 238 and 239 there is illustrated the snaring of a filter 1 as illustrated in FIG. 1 using a snare loop 998.

A further embolic protection filter 750 according to the invention is illustrated in FIGS. 240 and 241. The filter 750 comprises a collapsible filter support structure 751 and a collapsible filter body 752.

In the expanded, deployed configuration of FIG. 240, the support structure 751 does not have an inner tubular member to define a guidewire lumen for passing a guidewire 753 through. When the filter 750 is collapsed, the support structure collapses down into a smaller diameter tubular structure, as illustrated in FIG. 241. In this collapsed configuration, the support structure 751 defines the guidewire lumen for the guidewire 753. In this manner the support structure 751 isolates the filter body 752 from the guidewire 753, and thus prevents the filter body 752 from becoming fixed to the guidewire 753 during delivery or retrieval of the filter 750.

The filter 750 may be retrieved using any suitable means, such as a retrieval catheter 765 and a hook 766 (FIG. 242), in a manner similar to that described previously or a retrieval catheter 767 with a hoop 768 (FIG. 243), in a manner similar to that described previously.

If it is desired to remove the guidewire 753 from the filter 750 and recross the filter 750 with a second guidewire 754, the guidewire 754 may be threaded through one of the relatively large inlet openings 755 instead of through the relatively small proximal collar 756 of the support structure 751, as illustrated in FIG. 244. This enables a faster and more convenient means of recrossing the filter 750.

In addition, the distal collar 757 of the filter support structure 751 is spaced proximally of the distal end of the filter 750 to facilitate crossing of the filter 750 with the second guidewire 754 without requiring the guidewire 754 to be threaded through the distal collar 757 (FIG. 244).

The filter 750 can be retrieved after crossing the filter 750 with the second guidewire 754 using any suitable means (FIGS. 245 and 246).

Figure 247:
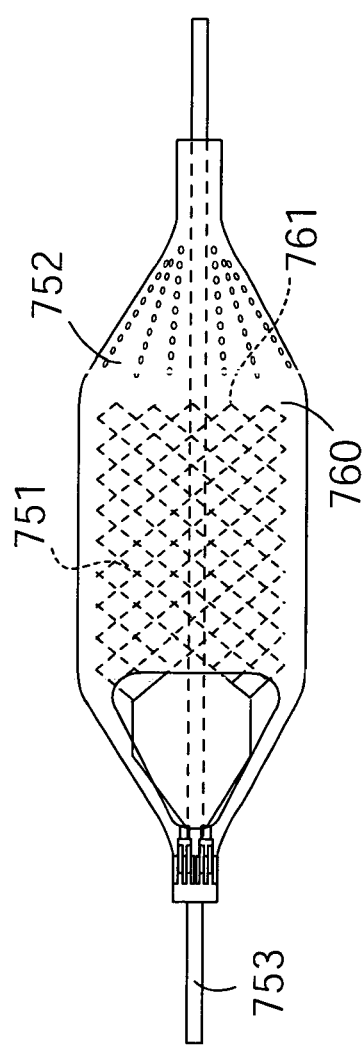
Figure 248:
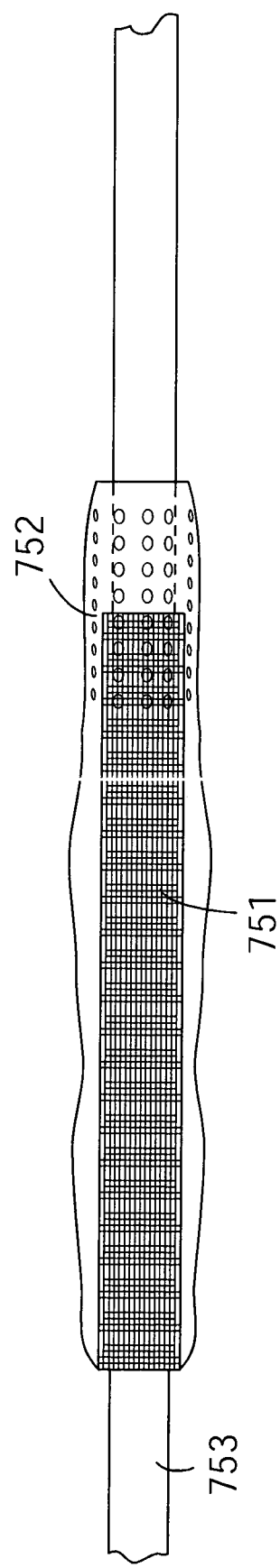

Referring to FIGS. 247 and 248, there is illustrated another embolic protection filter 760 according to the invention, which is similar to the embolic protection filter 750 of FIGS. 240 and 241, and similar elements in FIGS. 247 and 248 are assigned the same reference numerals.

The filter 760 is longitudinally shorter than the filter 750. In addition the filter support structure 751 ends in an open distal mouth 761 in the filter 760 and no distal collar is provided in the filter 760, as illustrated in FIG. 247.

In the filter 760, the filter body 752 is isolated from the guidewire 753 by the collapsed filter support structure 751 (FIG. 248), in a manner similar to that described previously with reference to FIG. 241.

The filter 760 may be recrossed by the second guidewire 754 by threading the guidewire 754 through one of the relatively large inlet openings 755 (FIG. 249), in a manner similar to that described previously with reference to FIG. 244.

Figure 252:
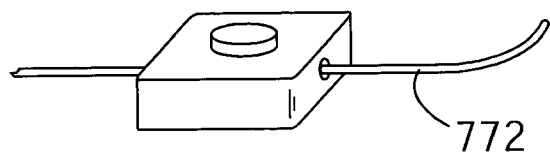
FIG. 252 is a schematic view illustrating fixing of an abutment to a guidewire.
Figure 253:
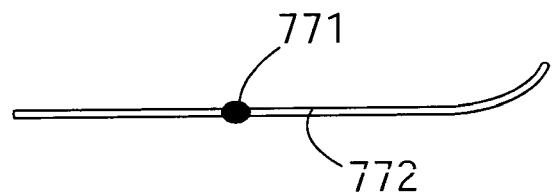
FIG. 253 is a schematic view of the guidewire and the abutment.

Referring to FIGS. 252 to 253 the position of the filter 1 in the vasculature may be controlled by an abutment 771 on a guidewire 772. By engaging the abutment 771 with an abutment surface on the filter, the filter is prevented from moving distally of the guidewire abutment 771. In this manner, the position of the filter 1 in the vasculature may be controlled, if necessary.

The abutment 771 may be fixedly attached to the guidewire 772 by a suitable means, such as by crimping, before introducing the guidewire 772 into the vasculature. Alternatively the abutment 771 may be fixed to the guidewire 772 during deployment of the filter.

Figure 254:
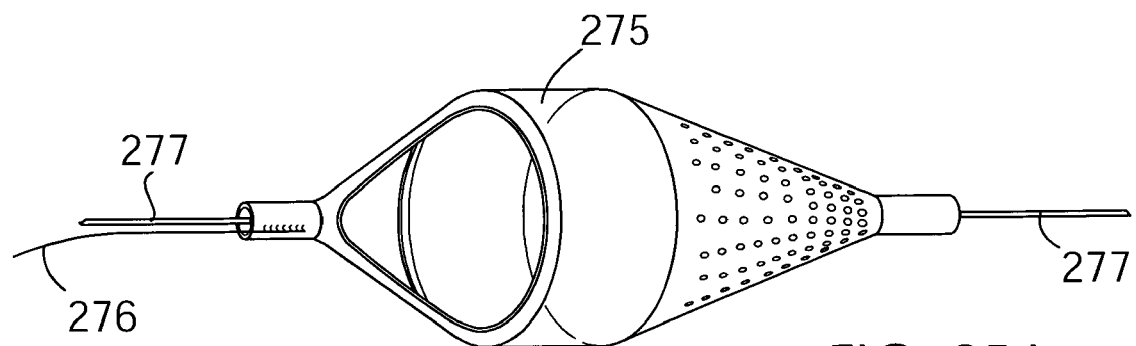
FIG. 254 is a perspective view of another embolic protection filter according to the invention passing over a guidewire.

As illustrated in FIG. 254 the filter 275 according to the invention may have a tether 276 fixed to the filter 275, extending proximally of the filter 275. The tether 276 may be used by a clinician to control the position of the filter 275 in the vasculature from a location externally of the vasculature. The tether 276 may be in the form of a wire, and may be of any suitable material.

In use, the filter 275 may be deployed over a guidewire 277. If appropriate or necessary, the guidewire 277 may then be withdrawn from the filter 275 and the vasculature. The tether wire 276 may then be used as a platform for advancing further devices through the vasculature, for example the retrieval catheter.

Figure 258:
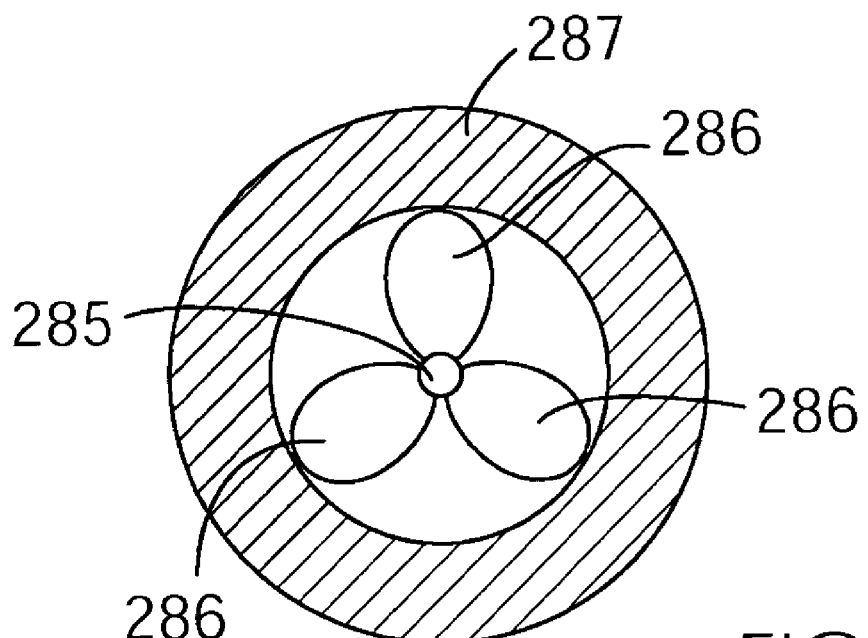
FIG. 258 is a cross-sectional, end view of a catheter according to the invention.
Figure 259:
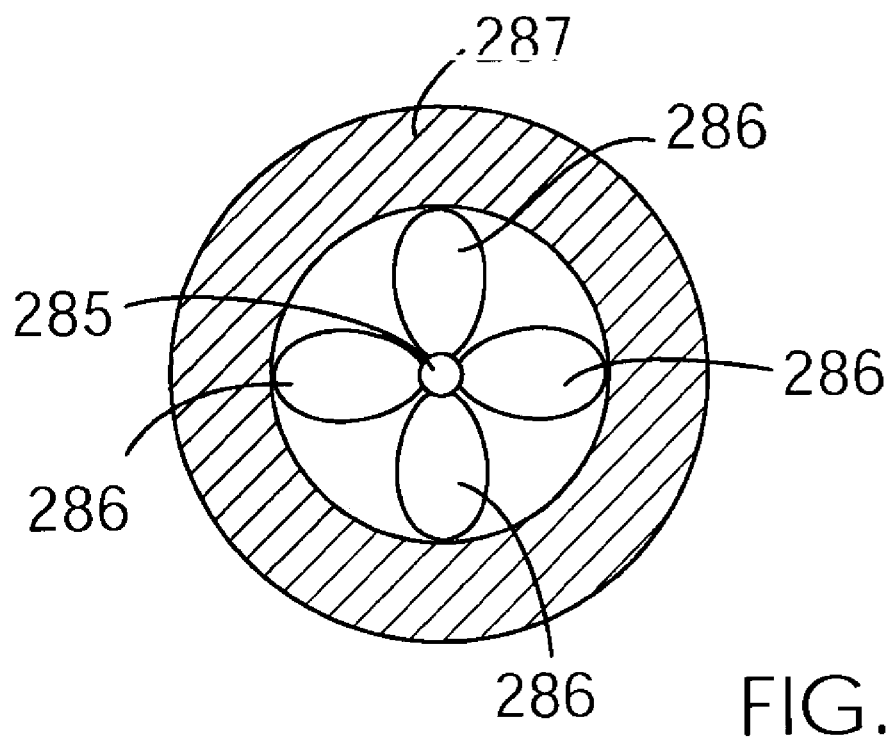
FIG. 259 is a cross-sectional, end view of a catheter according to the invention.

Referring to FIGS. 255 to 259, there is illustrated another embolic protection filter assembly 280 according to the invention. The assembly 280 comprises a filter 281 and a receiver to guide a guidewire 283 into the guidewire lumen 282. The receiver is provided, in this case, by an approach channel 284 for the guidewire 283 in the form of a lumen in a separate catheter 285. The catheter 285 has one or more inflatable balloons 286 at the distal end of the catheter 285. The shape and/or position of the balloons 286 is configured to ensure that the blood flow through the vasculature 287 will not be occluded upon inflation of the balloon(s) 286. In one case, the catheter 285 has three balloons 286 spaced circumferentially around the catheter 285, as illustrated in FIG. 258. In another case, the catheter 285 has four circumferentially spaced balloons 286 (FIG. 259).

Figure 255:
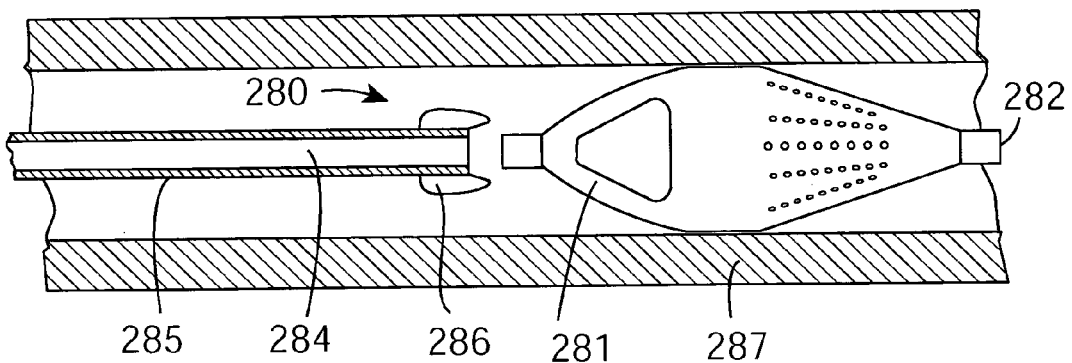
FIGS. 255 to 257 are partially cross-sectional side views illustrating guiding of a guidewire through an embolic protection filter.
Figure 256:
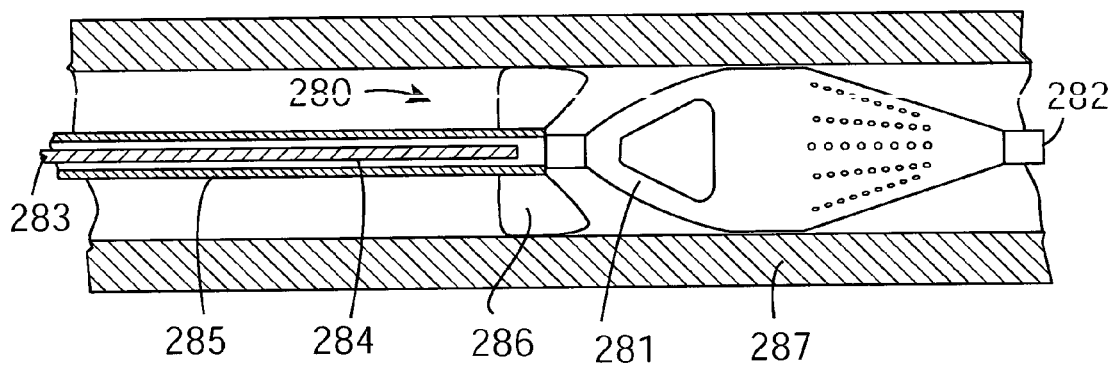
Figure 257:
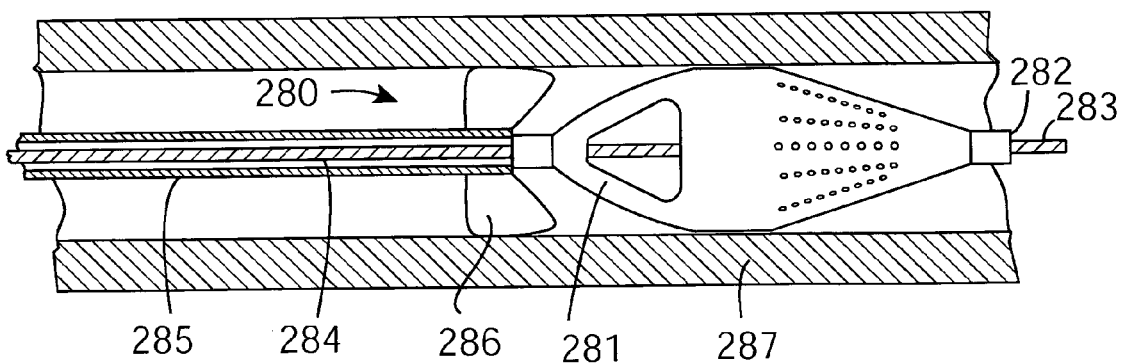

In use, the catheter 285 is introduced into the vasculature 287 and advanced through the vasculature 287 until the catheter distal end is proximally adjacent the filter 281 (FIG. 255). The balloon 286 is then inflated until the balloon 286 engages the wall of the vasculature 287. By engaging the balloon 286 with the wall of the vasculature 287, the catheter 285 is spaced from the wall of the vasculature 287 to assist in locating the catheter approach channel 284 centrally in the vasculature 287. The guidewire 283 may then be introduced into the channel 284 and advanced through the catheter 285. Because the channel 284 is located centrally in the vasculature 287, the guidewire 283 is guided into the guidewire lumen 282 of the filter 281 as it passes out of the distal end of the channel 284. The balloon 286 may be deflated to a low profile configuration during introduction and withdrawal of the catheter 285 from the vasculature 287.

It will be appreciated that any number of seals may be provided to prevent embolic material passing through the guidewire lumen or the guidewire aperture, and the seals may be positioned at any suitable point along the guidewire lumen or the guidewire aperture.

It will further be appreciated that the receiver may be configured to guide a docking device in the form of a coupling member, such as those described previously, towards the filter for coupling to the filter. In such a manner, the receiver may be used to assist retrieval of the filter. The coupling means may be achieved by numerous alternatives, for example male-female inter-engagement, or magnetic coupling, or hook and eyelet means.

Figure 260:
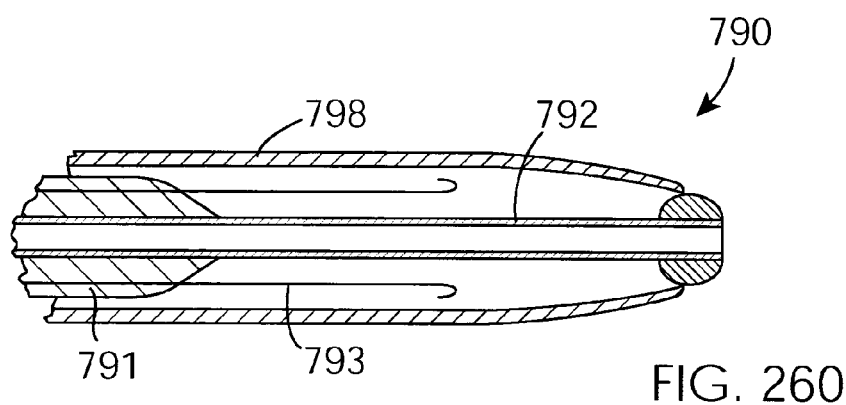
FIG. 260 is a cross-sectional, side view of another retrieval catheter according to the invention.
Figure 261:
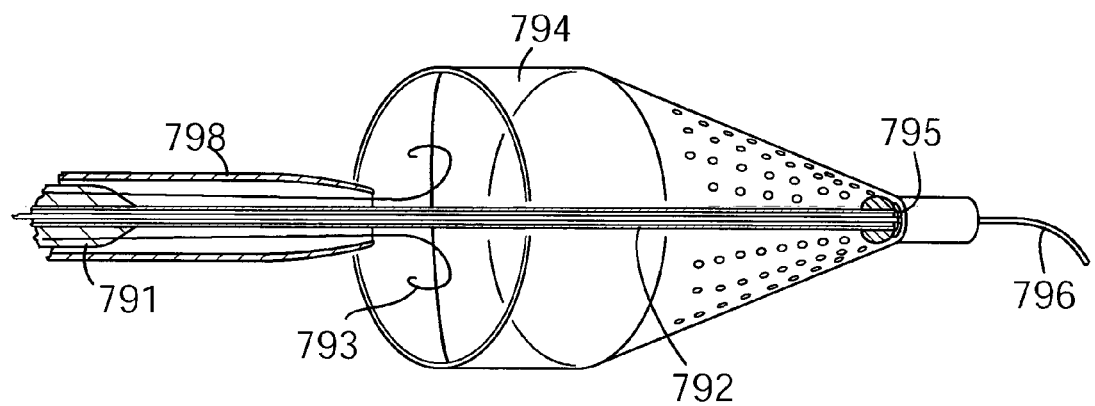
FIG. 261 is a partially cross-sectional, side view illustrating retrieval of an embolic protection filter using the retrieval catheter of FIG. 260.

FIG. 260 illustrates another retrieval catheter 790 according to the invention. A coupling member 791, in this case, has a tubular extension part 792 which extends distally of hooks 793. In use, the tubular extension 792 may be extended through an embolic protection filter 794 to be retrieved, as illustrated in FIG. 261. The tubular extension 792 in this way defines the guidewire lumen 795 through the filter 794 through which a guidewire 796 may be passed.

The retrieval catheter 790 is particularly suitable for retrieving filters, such as the filter 794 which do not have an inner tubular member to define a guidewire lumen through the filter 794. Filters which do not have an inner tubular member are liable to becoming fixed against the guidewire 796 when the filter is collapsed down. When this occurs it is no longer possible to retrieve the filter while the guidewire remains in situ in the vasculature.

By defining the guidewire lumen 795 using the tubular extension 792 of the retrieval catheter 790, this serves to isolate the collapsing filter 794 from the guidewire 796, and thus prevents the filter 794 from becoming fixed to the guidewire 796.

The tubular extension 792 may be advanced to the distal end of the filter 794 before retrieving the filter 794 into a catheter body 798, as illustrated in FIG. 261.

Alternatively the tubular extension 792 may be advanced until the tubular extension 792 is distally of the distal end of the filter 794 before retrieving the filter 794 into the catheter body 798.

The invention is not limited to the embodiments hereinbefore described, with reference to the accompanying drawings, which may be varied in construction and detail.

The invention claimed is:

1. An embolic protection system comprising:

a filter for deployment in a vasculature, the filter having an inlet end and an outlet end, the inlet end having one or more inlet openings sized to allow blood and embolic material enter the filter, and the outlet end of the filter having a plurality of outlet openings sized to allow through passage of blood but to retain undesired embolic material within the filter, the filter being movable between a collapsed configuration for movement through a vasculature, and an outwardly extended configuration for deployment in a vasculature; and a lumen-defining member defining, at least in the collapsed configuration, a guidewire lumen at least partially through the filter for passing the filter over a guidewire, the lumen-defining member being movable or removable relative to the filter, wherein the lumen-defining member is a substantially tubular member and wherein the tubular member has a slit extending the entire length thereof for removal of the member from a guidewire and wherein the tubular member extends at least partially through the filter.

2. A system as claimed in claim 1 wherein the lumen-defining member comprises a gripable portion for gripping the lumen-defining member to move or remove the lumen-defining member relative to the filter.

3. A system as claimed in claim 2 wherein the gripable portion is provided at a distal end of the lumen-defining member.

* * * * *